United States Patent
Hinman et al.

(10) Patent No.: US 10,189,830 B2
(45) Date of Patent: Jan. 29, 2019

(54) ALKYL-HETEROARYL SUBSTITUTED QUINONE DERIVATIVES FOR TREATMENT OF OXIDATIVE STRESS DISORDERS

(71) Applicant: BioElectron Technology Corporation, Mountain View, CA (US)

(72) Inventors: Andrew W. Hinman, San Francisco, CA (US); Kieron E. Wesson, Burlingame, CA (US); Christopher R. Cornell, Mountain View, CA (US)

(73) Assignee: BIOELECTRON TECHNOLOGY CORPORATION, Mountain View, CA (US)

( * ) Notice: Subject to any disclaimer, the term of this patent is extended or adjusted under 35 U.S.C. 154(b) by 0 days.

(21) Appl. No.: 14/776,678

(22) PCT Filed: Mar. 14, 2014

(86) PCT No.: PCT/US2014/029806
§ 371 (c)(1),
(2) Date: Sep. 14, 2015

(87) PCT Pub. No.: WO2014/145116
PCT Pub. Date: Sep. 18, 2014

(65) Prior Publication Data
US 2016/0024085 A1 Jan. 28, 2016

Related U.S. Application Data

(60) Provisional application No. 61/798,937, filed on Mar. 15, 2013.

(51) Int. Cl.
| | | |
|---|---|---|
| *C07D 471/04* | (2006.01) |
| *C07D 263/56* | (2006.01) |
| *C07D 233/60* | (2006.01) |
| *C07D 233/64* | (2006.01) |
| *C07D 235/06* | (2006.01) |
| *C07D 235/12* | (2006.01) |
| *C07D 403/10* | (2006.01) |
| *C07D 249/08* | (2006.01) |
| *C07D 263/32* | (2006.01) |
| *C07D 277/24* | (2006.01) |
| *C07D 277/64* | (2006.01) |
| *C07D 263/57* | (2006.01) |

(52) U.S. Cl.
CPC ......... *C07D 471/04* (2013.01); *C07D 233/60* (2013.01); *C07D 233/64* (2013.01); *C07D 235/06* (2013.01); *C07D 235/12* (2013.01); *C07D 249/08* (2013.01); *C07D 263/32* (2013.01); *C07D 263/56* (2013.01); *C07D 263/57* (2013.01); *C07D 277/24* (2013.01); *C07D 277/64* (2013.01); *C07D 403/10* (2013.01)

(58) Field of Classification Search
USPC .................................... 514/252.06, 677, 688
See application file for complete search history.

(56) References Cited

U.S. PATENT DOCUMENTS

| | | | |
|---|---|---|---|
| 5,229,385 A * | 7/1993 | Terao ................... | C07D 213/50 514/235.5 |
| 6,133,278 A | 10/2000 | Terao et al. | |
| 6,136,839 A | 10/2000 | Isakson et al. | |
| 7,034,054 B2 | 4/2006 | Miller et al. | |
| 7,179,928 B2 | 2/2007 | Smith et al. | |
| 7,432,305 B2 | 10/2008 | Miller et al. | |
| 7,470,798 B2 | 12/2008 | Wang et al. | |

(Continued)

FOREIGN PATENT DOCUMENTS

| DE | 10121252 A1 | 11/2002 |
|---|---|---|
| EP | 0234729 A2 | 9/1987 |

(Continued)

OTHER PUBLICATIONS

STN database; RN 747411-22-9, supplier: Enamine; Sep. 19, 2004.*

(Continued)

*Primary Examiner* — Pancham Bakshi
(74) *Attorney, Agent, or Firm* — Squire Patton Boggs (US) LLP

(57) ABSTRACT

Disclosed herein are alkyl-heteroaryl substituted quinone derivative compounds and methods of using such compounds for treating or suppressing oxidative stress disorders, including mitochondrial disorders, impaired energy processing disorders, neurodegenerative diseases and diseases of aging.

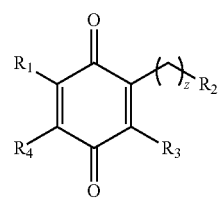

Formula I

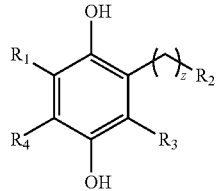

Formula II

14 Claims, No Drawings

(56) References Cited

U.S. PATENT DOCUMENTS

| | | |
|---|---|---|
| 7,491,312 B2 | 2/2009 | Gilat et al. |
| 7,514,461 B2 | 4/2009 | Wang et al. |
| 7,968,746 B2 | 6/2011 | Jankowski et al. |
| 8,106,223 B2 | 1/2012 | Wesson et al. |
| 8,314,153 B2 | 11/2012 | Miller et al. |
| 8,716,486 B2 | 5/2014 | Hinman et al. |
| 8,716,527 B2 | 5/2014 | Hinman et al. |
| 8,952,071 B2 | 2/2015 | Hinman et al. |
| 9,162,957 B2 | 10/2015 | Mollard |
| 9,278,085 B2 | 3/2016 | Miller et al. |
| 9,296,712 B2 | 3/2016 | Hinman et al. |
| 9,370,496 B2 | 6/2016 | Miller |
| 9,540,322 B2 | 1/2017 | Jorgensen et al. |
| 2005/0239807 A1 | 10/2005 | Stamler et al. |
| 2006/0281809 A1 | 12/2006 | Miller et al. |
| 2008/0280826 A1 | 11/2008 | O'Connor |
| 2009/0111837 A1 | 4/2009 | Cox et al. |
| 2011/0105959 A1 | 5/2011 | O'Connor |
| 2011/0207828 A1 | 8/2011 | Miller et al. |
| 2011/0269776 A1 | 11/2011 | Miller |
| 2012/0076795 A1 | 3/2012 | Debs |
| 2013/0109759 A1 | 5/2013 | Miller |
| 2013/0267538 A1 | 10/2013 | Walkinshaw et al. |
| 2013/0345312 A1 | 12/2013 | Jankowski et al. |
| 2014/0031433 A1 | 1/2014 | Miller et al. |
| 2014/0243424 A1 | 8/2014 | Mollard et al. |
| 2014/0249160 A1 | 9/2014 | Miller |
| 2014/0275045 A1 | 9/2014 | Hinman et al. |
| 2014/0343166 A1 | 11/2014 | Miller et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2015/0297551 A1 | 10/2015 | Hinman et al. |
| 2016/0039775 A1 | 2/2016 | Hinman et al. |
| 2016/0039776 A1 | 2/2016 | Hinman et al. |
| 2016/0115141 A1 | 4/2016 | Hinman et al. |

FOREIGN PATENT DOCUMENTS

| | | |
|---|---|---|
| EP | 560568 A2 | 9/1993 |
| JP | 62223150 A | 10/1987 |
| JP | 4225972 A | 8/1992 |
| JP | 9-59258 A | 3/1997 |
| JP | 9221471 A | 8/1997 |
| WO | WO-96/41626 A1 | 12/1996 |
| WO | WO-97/29776 A1 | 8/1997 |
| WO | WO-2012022467 A2 | 2/2012 |
| WO | WO-2013/136078 | 9/2013 |
| WO | WO-2014/031586 | 2/2014 |

OTHER PUBLICATIONS

International Search Report and Written Opinion dated Dec. 4, 2014 for PCT/US2014/029806 filed on Mar. 14, 2014, 17 pages.

International Preliminary Report on Patentability dated Sep. 24, 2015 for PCT/US2014/029806 filed on Mar. 14, 2014, 12 pages.

Ferry et al. "A Phase II study of the 5-lipoxygenase Inhibitor, CV6504, in Advanced Pancreatic Cancer: Correlation of Clinical Data with Pharmacokinetic and Pharmacodynamic Endpoints", *Annals of Oncology*, 2000, vol. 11, pp. 1165-1170.

Hussey et al., Mechanism of the anti-tumour effect of 2,3,5-trimethyl-6-(3-pyridylmethyl) 1,4-benzoquinone (CV-6504), *British Journal of Cancer*, 1997, vol. 75, No. 6, pp. 845-849.

Hussey et al., Metabolism and pharmacokinetics of the anti-tumour agent 2,3,5-trimethyl-6-(3-pyridylmethyl) 1,4-benzoquinone (CV-6504), *British Journal of Cancer*, 1996, vol. 74, pp. 1349-1353.

Hussey et al., "Novel anti-tumour activity of 2,3,5-trimethyl-6-(3-pyridylnnethyl)-1,4-benzoquinone (CV-6504) against establishedmurine adenocarcinomas (MAC)", *Britsh Journal of Cancer*, 1996, vol. 73, pp.

Hwang et al. "A Theoretical Study on 5-Lipoxygenase Inhibitors with a transition State Analog Approach", *Korean Journal of Medicinal Chemistry*, 1993, vol. 3, No. 2, pp. 93-101.

Ohkawa et al. "Dual Inhibitors of Thromboxane A2 Synthase and 5-Lipoxygenase with Scavenging Activity of Active Oxygen Species. Synthesis of a Novel Series of (3-Pyridylmethyl)benzoquinone Derivatives", *J. Med. Chem.*, 1991, vol. 34, pp. 267-276.

Ohkawa et al. "Reduction of 2,3,5-Trimethyl-6-(3-pyridylmethyl)-1,4-benzoquinone by PB-3c Cells and Biological Activity of Its Hydroquinone", *Chem. Pharm. Bull.*, 1991, vol. 39, No. 4, pp. 917-921.

Shibouta et al. "Involvement of Thromboxane A2, Leukotrienes and Free Radicals in Puromycin Nephrosis in Rats", *Kidney International*, 1991, vol. 39, pp. 920-929.

Terao et al, "Synthesis and Biological Evaluation of 2,3,5-Trimethyl-6-(3-Pyridylmethyl)-1,4-Benzoquinone (CV-6504), a Dual Inhibitor of TXA2 Synthase and 5-Lipdxygenase With Scavenging Activity of Active Oxygen Species (AOS)", *Advances in Prostaglandin, Throinboxane, and Leukotriene Research*, 1990, vol. 21, pp. 173-176.

Veres et al. "Modeling Biological Activity of (3-Pyridylmethyl)Benzoquinone Derivatives", *Studia Universitatis Babes-Bolyai, Chemia*, 2003, vol. 48, No. 2, pp. 46-54.

Whitehouse et al. "Downregulation of Ubiquitin-Dependent Proteolysis by Eicosapentaenoic Acid in Acute Starvation", *Biochemical and Biophysical Research Communications*, 2001, vol. 285, No. 3, pp. 598-602.

Office Action of Japanese patent application No. 2016-503224 dated Jan. 25, 2018 togethr with Englsih translation, 18 pages.

Andreani, A. et al., "Effects of new ubiquinone-imidazo[2,1-b]thiazoles on mitochondrial complex I (NADH-ubiquinone reductase) and on mitochondrial permeability transition pore", Bioorganic & Medicinal Chemistry, 2004, vol. 12, No. 21, pp. 5525-5532.

Registry (STN) [online], Entered STN: Jun. 8, 2008, retrieved date: Dec. 18, 2017, CAS Registry Number: 1026415-54-2; 1 page.

Registry (STN) [online], Entered STN: Sep. 19, 2004, retrieved date: Dec. 18, 2017, CAS Registry Number: 747411-24-1; 1 page.

Registry (STN) [online], Entered STN: Sep. 19, 2004, retrieved date: Dec. 18, 2017, CAS Registry Number: 747411-21-8; 1 page.

Suzuki, K. et al., "2-Arylmethy1-1,4-benzoquinones. II. Novel Inhibitors of Platelet Aggregation: Synthesis and Pharmacological Evaluation", Chemical & Pharmaceutical Bulletin, 1997, vol. 45, No. 4, pp. 668-674.

\* cited by examiner

ALKYL-HETEROARYL SUBSTITUTED QUINONE DERIVATIVES FOR TREATMENT OF OXIDATIVE STRESS DISORDERS

CROSS-REFERENCE TO RELATED APPLICATIONS

This application claims priority benefit of U.S. Provisional Patent Application No. 61/798,937, filed Mar. 15, 2013. The entire contents of that patent application are hereby incorporated by reference herein.

TECHNICAL FIELD

The application discloses compositions and methods useful for treatment or suppression of diseases, developmental delays and symptoms related to oxidative stress disorders. Examples of such disorders include mitochondrial disorders, impaired energy processing disorders, neurodegenerative diseases and diseases of aging.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery. The most important source of reactive oxygen species under normal conditions in aerobic organisms is probably the leakage of activated oxygen from mitochondria during normal oxidative respiration. Impairments associated with this process are suspected to contribute to mitochondrial disease, neurodegenerative disease, and diseases of aging.

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide (NADH+H+) from oxidized nicotinamide adenine dinucleotide (NAD+), and oxidative phosphorylation, during which NADH+H+ is oxidized back to NAD+. (The citric acid cycle also reduces flavin adenine dinucleotide, or FAD, to FADH2; FADH2 also participates in oxidative phosphorylation.)

The electrons released by oxidation of NADH+H+ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as haemoglobinopathies. Haemoglobinopathy is a kind of genetic defect that results in abnormal structure of one of the globin chains of the hemoglobin molecule. Common haemoglobinopathies include thalassemia and sickle-cell disease. Thalassemia is an inherited autosomal recessive blood disease. In thalassemia, the genetic defect results in reduced rate of synthesis of one of the globin chains that make up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. Some examples of mitochondrial diseases are Friedreich's ataxia (FRDA), Leber's Hereditary Optic Neuropathy (LHON), mitochondrial myopathy, encephalopathy, lactacidosis, and stroke (MELAS), Myoclonus Epilepsy Associated with Ragged-Red Fibers (MERRF) syndrome, Leigh's disease, and respiratory chain disorders. Most mitochondrial diseases involve children who manifest the signs and symptoms of accelerated aging, including neurodegenerative diseases, stroke, blindness, hearing impairment, vision impairment, diabetes, and heart failure.

Friedreich's ataxia is an autosomal recessive neurodegenerative and cardiodegenerative disorder caused by decreased levels of the protein Frataxin. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Leber's Hereditary Optic Neuropathy (LHON) is a disease characterized by blindness which occurs on average between 27 and 34 years of age. Other symptoms may also occur, such as cardiac abnormalities and neurological complications.

Mitochondrial myopathy, encephalopathy, lactacidosis, and stroke (MELAS) can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke.

Myoclonus Epilepsy Associated with Ragged-Red Fibers (MERRF) syndrome is one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body, difficulty speaking (dysarthria), optic atrophy, short stature, hearing loss, dementia, and involuntary jerking of the eyes (nystagmus) may also occur.

Leigh's disease is a rare inherited neurometabolic disorder characterized by degeneration of the central nervous system where the symptoms usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur.

Co-Enzyme Q10 Deficiency is a respiratory chain disorder, with syndromes such as myopathy with exercise intolerance and recurrent myoglobin in the urine manifested by ataxia, seizures or mental retardation and leading to renal failure (Di Mauro et al., (2005) Neuromusc. Disord., 15:311-315), childhood-onset cerebellar ataxia and cerebellar atrophy (Masumeci et al., (2001) Neurology 56:849-855 and Lamperti et al., (2003) 60:1206:1208); and infantile encephalomyopathy associated with nephrosis. Biochemical measurement of muscle homogenates of patients with CoQ10 deficiency showed severely decreased activities of respiratory chain complexes I and II+III, while complex IV (COX) was moderately decreased (Gempel et al., (2007) Brain, 130(8):2037-2044).

Complex I Deficiency or NADH dehydrogenase NADH-CoQ reductase deficiency is a respiratory chain disorder, with symptoms classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Complex II Deficiency or Succinate dehydrogenase deficiency is a respiratory chain disorder with symptoms including encephalomyopathy and various manifestations, including failure to thrive, developmental delay, hypotonia, lethargy, respiratory failure, ataxia, myoclonus and lactic acidosis.

Complex III Deficiency or Ubiquinone-cytochrome C oxidoreductase deficiency is a respiratory chain disorder with symptoms categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Complex IV Deficiency or Cytochrome C oxidase deficiency is a respiratory chain disorder with symptoms categorized in two major forms: (1) encephalomyopathy, where patients typically are normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy with two main variants: (a) Fatal infantile myopathy—may begin soon after birth and accompanied by hypotonia, weakness, lactic acidosis, ragged-red fibers, respiratory failure, and kidney problems: and (b) Benign infantile myopathy—may begin soon after birth and accompanied by hypotonia, weakness, lactic acidosis, ragged-red fibers, respiratory problems, but (if the child survives) followed by spontaneous improvement.

Complex V Deficiency or ATP synthase deficiency is a respiratory chain disorder including symptoms such as slow, progressive myopathy.

CPEO or Chronic Progressive External Ophthalmoplegia Syndrome is a respiratory chain disorder including symptoms such as visual myopathy, retinitis pigmentosa, or dysfunction of the central nervous system.

Kearns-Sayre Syndrome (KSS) is a mitochondrial disease characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis.

Maternally inherited diabetes and deafness (MIDD) is a mitochondrial disorder characterized by maternally transmitted diabetes and sensorineural deafness. In most cases, MIDD is caused by a point mutation in the mitochondrial gene MT-TL1, encoding the mitochondrial tRNA for leucine, and in rare cases in MT-TE and MT-TK genes, encoding the mitochondrial tRNAs for glutamic acid, and lysine, respectively.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitoxic, neuronal injury, such as that associated with cerebrovascular accidents, seizures and ischemia.

Some of the above diseases appear to be caused by defects in Complex I of the respiratory chain. Electron transfer from Complex I to the remainder of the respiratory chain is mediated by the compound coenzyme Q (also known as Ubiquinone). Oxidized coenzyme Q (CoQox or Ubiquinone) is reduced by Complex I to reduced coenzyme Q (CoQred or Ubiquinol). The reduced coenzyme Q then transfers its electrons to Complex III of the respiratory chain, where it is re-oxidized to CoQox (Ubiquinone). CoQox can then participate in further iterations of electron transfer.

Very few treatments are available for patients suffering from these mitochondrial diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. Administration of coenzyme Q10 (CoQ10) and vitamin supplements has shown only transient beneficial effects in individual cases of KSS. CoQ10 supplementation has also been used for the treatment of CoQ10 deficiency with mixed results.

Oxidative stress is suspected to be important in neurodegenerative diseases such as Motor Neuron Disease, Amyotrophic Lateral Sclerosis (ALS), Creutzfeldt-Jakob disease, Machado-Joseph disease, Spino-cerebellar ataxia, Multiple sclerosis (MS), Parkinson's disease, Alzheimer's disease, and Huntington's disease. Oxidative stress is thought to be linked to certain cardiovascular disease and also plays a role in the ischemic cascade due to oxygen reperfusion injury following hypoxia. This cascade includes both strokes and heart attacks.

Damage accumulation theory, also known as the free radical theory of aging, invokes random effects of free radicals produced during aerobic metabolism that cause damage to DNA, lipids and proteins and accumulate over time. The concept of free radicals playing a role in the aging process was first introduced by Himan D (1956), Aging—A theory based on free-radical and radiation chemistry J. Gerontol. 11, 298-300.

According to the free radical theory of aging, the process of aging begins with oxygen metabolism (Valko et al, (2004) Role of oxygen radicals in DNA damage and cancer incidence, Mol. Cell. Biochem., 266, 37-56). Even under ideal conditions some electrons "leak" from the electron transport chain. These leaking electrons interact with oxygen to produce superoxide radicals, so that under physiological conditions, about 1-3% of the oxygen molecules in the mitochondria are converted into superoxide. The primary site of radical oxygen damage from superoxide radical is mitochondrial DNA (mtDNA) (Cadenas et al., (2000) Mitochondrial free radical generation, oxidative stress and aging, Free Radic. Res, 28, 601-609). The cell repairs much of the damage done to nuclear DNA (nDNA) but mtDNA repair seems to be less efficient. Therefore, extensive mtDNA damage accumulates over time and shuts down mitochondria causing cells to die and the organism to age.

Some of the diseases associated with increasing age are cancer, diabetes mellitus, hypertension, atherosclerosis, ischemia/reperfusion injury, rheumatoid arthritis, neurodegenerative disorders such as dementia, Alzheimer's and Parkinson's. Diseases resulting from the process of aging as a physiological decline include decreases in muscle strength, cardiopulmonary function, vision and hearing as well as wrinkled skin and graying hair.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

BRIEF SUMMARY OF THE INVENTION

In one aspect of the invention is a compound of Formula I or Formula II:

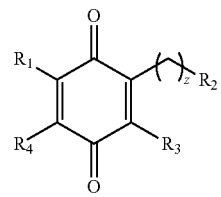

Formula I

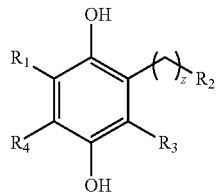

Formula II wherein: $R_1$, $R_3$ and $R_4$ are independently $C_1$-$C_6$ alkyl or —O—$C_1$-$C_6$ alkyl; $R_2$ is heteroaryl optionally substituted with one or two substituents independently selected from the group consisting of —$CH_3$, —$CF_3$, halo, —$OCH_3$, and —C(O)—N($R_5$)($R_6$), wherein the substituents are independently linked to the heteroaryl by either a —C— or —N— within the heteroaryl; $R_5$ and $R_6$ are independently selected from the group consisting of —H, —$C_1$-$C_6$ alkyl, and —$C_1$-$C_6$ alkyl-hydroxy, or wherein $R_5$ and $R_6$ together with the N to which they are attached form a saturated or unsaturated 3-8 membered ring, optionally incorporating one, two, or three additional heteroatoms each independently selected from the group consisting of N, O, and S, and wherein the ring is optionally substituted with —$C_1$-$C_6$ alkyl; and z is 1, 2, 3, 4, 5, or 6; or a stereoisomer, mixture of stereoisomers, solvate, hydrate, pharmaceutically acceptable salt or prodrug ester thereof; with the proviso that the compound is not:

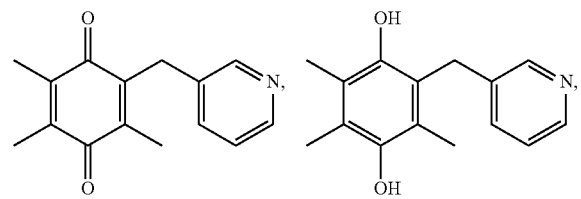

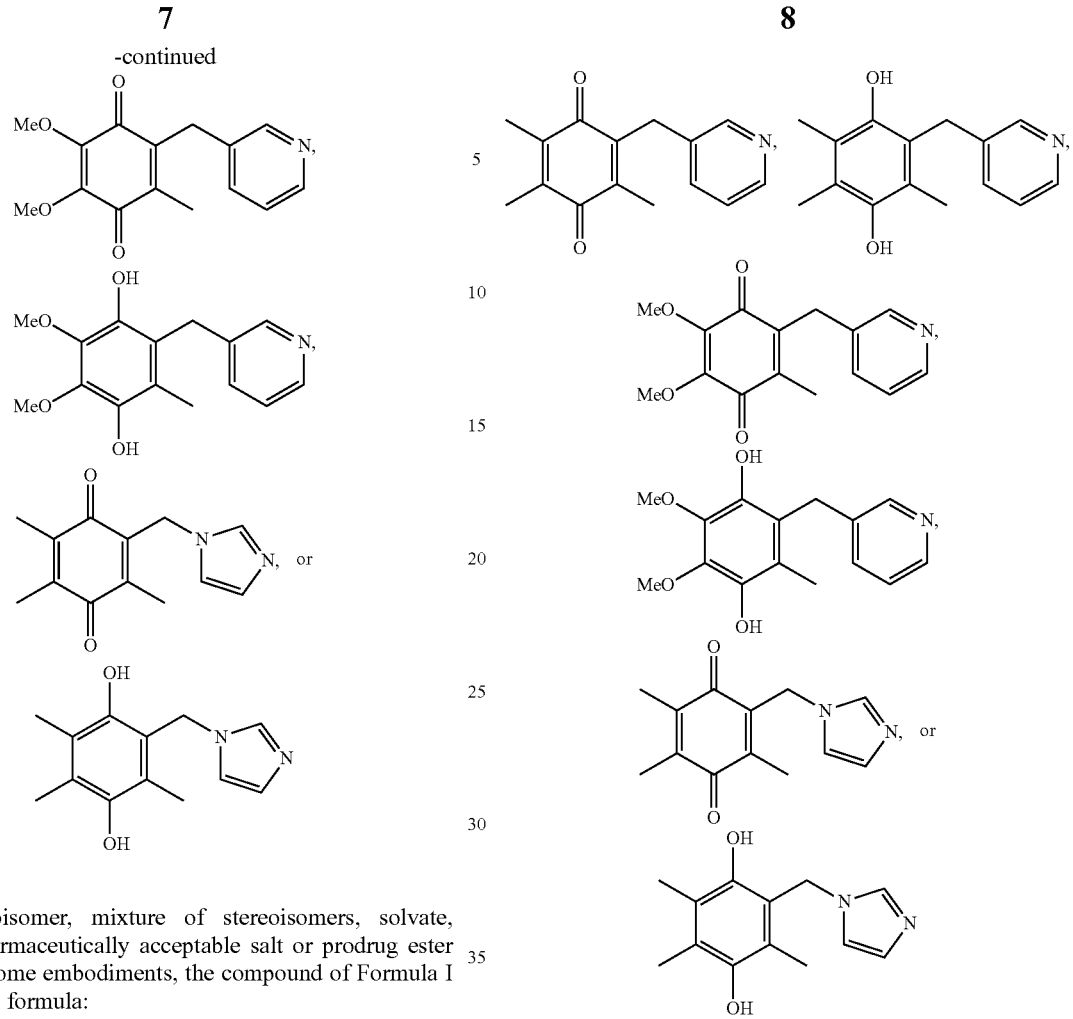

or a stereoisomer, mixture of stereoisomers, solvate, hydrate, pharmaceutically acceptable salt or prodrug ester thereof. In some embodiments, the compound of Formula I or II has the formula:

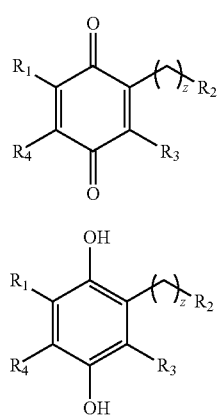

Formula I

Formula II wherein: $R_1$, $R_3$ and $R_4$ are independently $C_1$-$C_6$ alkyl or —O—$C_1$-$C_6$ alkyl; $R_2$ is heteroaryl optionally substituted with one or two substituents independently selected from the group consisting of —$CH_3$, —$CF_3$, halo, and —$OCH_3$, wherein the substituents are independently linked to the heteroaryl by either a —C— or —N— within the heteroaryl; and z is 1, 2, 3, 4, 5, or 6; or a stereoisomer, mixture of stereoisomers, solvate, hydrate, pharmaceutically acceptable salt or prodrug ester thereof; with the proviso that the compound is not:

or a stereoisomer, mixture of stereoisomers, solvate, hydrate, pharmaceutically acceptable salt or prodrug ester thereof. In some embodiments, including any of the foregoing embodiments, z is 2, 3, 4, 5, or 6. In some embodiments, including any of the foregoing embodiments, z is 1, 2, or 3. In some embodiments, including any of the foregoing embodiments, z is 2 or 3. In some embodiments, including any of the foregoing embodiments, z is 1. In some embodiments, including any of the foregoing embodiments, z is 2. In some embodiments, including any of the foregoing embodiments, z is 3. In some embodiments, including any of the foregoing embodiments, z is 4. In some embodiments, including any of the foregoing embodiments, z is 5. In some embodiments, including any of the foregoing embodiments, z is 6. In some embodiments, including any of the foregoing embodiments, $R_1$, $R_3$ and $R_4$ are independently $C_1$-$C_6$ alkyl. In some embodiments, including any of the foregoing embodiments, $R_1$, $R_3$ and $R_4$ are independently $C_1$-$C_4$ alkyl. In some embodiments, including any of the foregoing embodiments, $R_1$, $R_3$ and $R_4$ are independently $C_1$-$C_2$ alkyl. In some embodiments, including any of the foregoing embodiments, $R_1$, $R_3$ and $R_4$ are —$CH_3$. In some embodiments, including any of the foregoing embodiments, $R_1$ and $R_4$ are independently —O—$C_1$-$C_4$ alkyl, and $R_3$ is $C_1$-$C_4$ alkyl. In some embodiments, including any of the foregoing embodiments, $R_1$ and $R_4$ are independently —O—$C_1$-$C_2$ alkyl, and $R_3$ is $C_1$-$C_4$ alkyl. In some embodiments, including any of the foregoing embodiments, $R_1$, $R_3$ and $R_4$ are —OCH₃. In some embodiments, including any of the foregoing embodiments, $R_1$ and $R_4$ are —OCH₃, and $R_3$ is —CH₃. In some embodiments, $R_1$, $R_3$ and $R_4$ are —CH₃; and z is 1, 2, or 3. In some embodiments, including any of the foregoing embodiments, $R_1$, $R_3$ and $R_4$ are —CH₃; and z is 2 or 3. In some embodiments, including any of the foregoing embodiments, the heteroaryl is selected from the group consisting of: benzoimidazole, benzothiazole, benzoxazole, thiazole, oxazole, imidazole, and triazole. In some embodiments, including any of the foregoing embodiments, the heteroaryl is selected from the group consisting of: benzoimidazole, benzothiazole, benzoxazole, thiazole, oxazole, imidazole, and triazole. In some embodiments, including any of the foregoing embodiments, the heteroaryl is not pyridine. In some embodiments, including any of the foregoing embodiments, the heteroaryl is not imidazole. In some embodiments, including any of the foregoing embodiments, $R_2$ is unsubstituted. In some embodiments, including any of the foregoing embodiments, $R_2$ is substituted with a single substituent. In some embodiments, including any of the foregoing embodiments, $R_2$ is substituted with two substituents. In some embodiments, including any of the foregoing embodiments, $R_2$ is selected from the group consisting of:

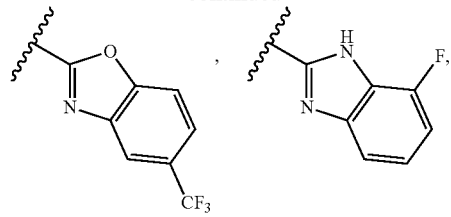

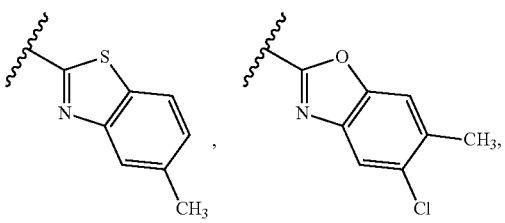

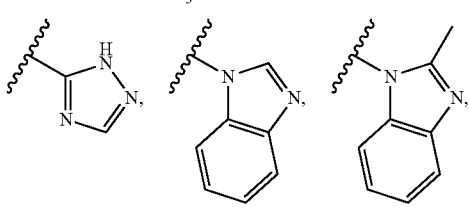

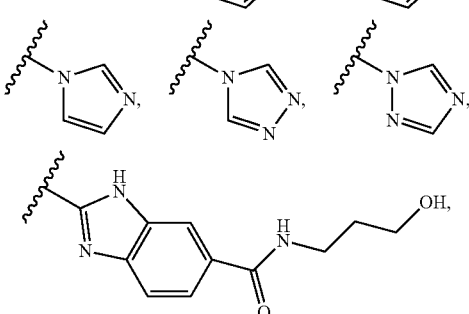

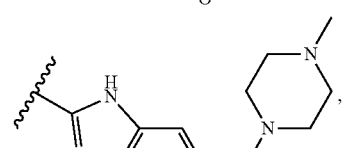

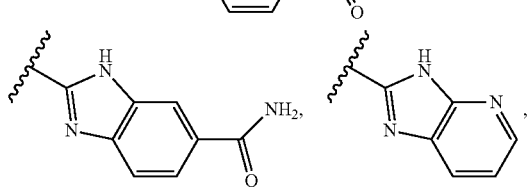

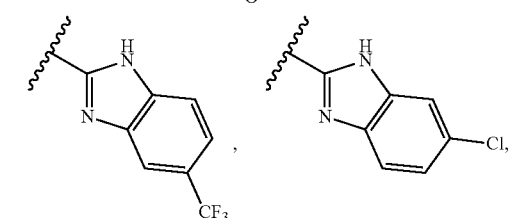

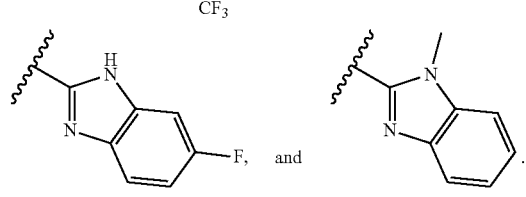

In some embodiments, including any of the foregoing embodiments, $R_2$ is selected from the group consisting of:
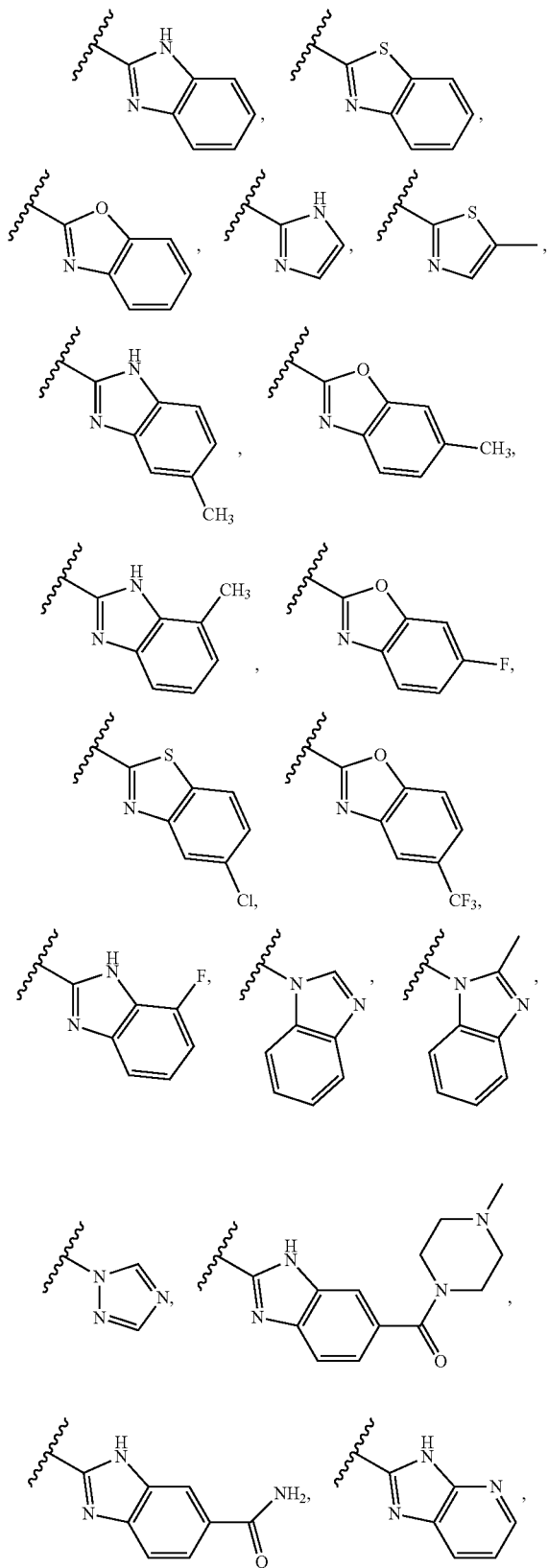
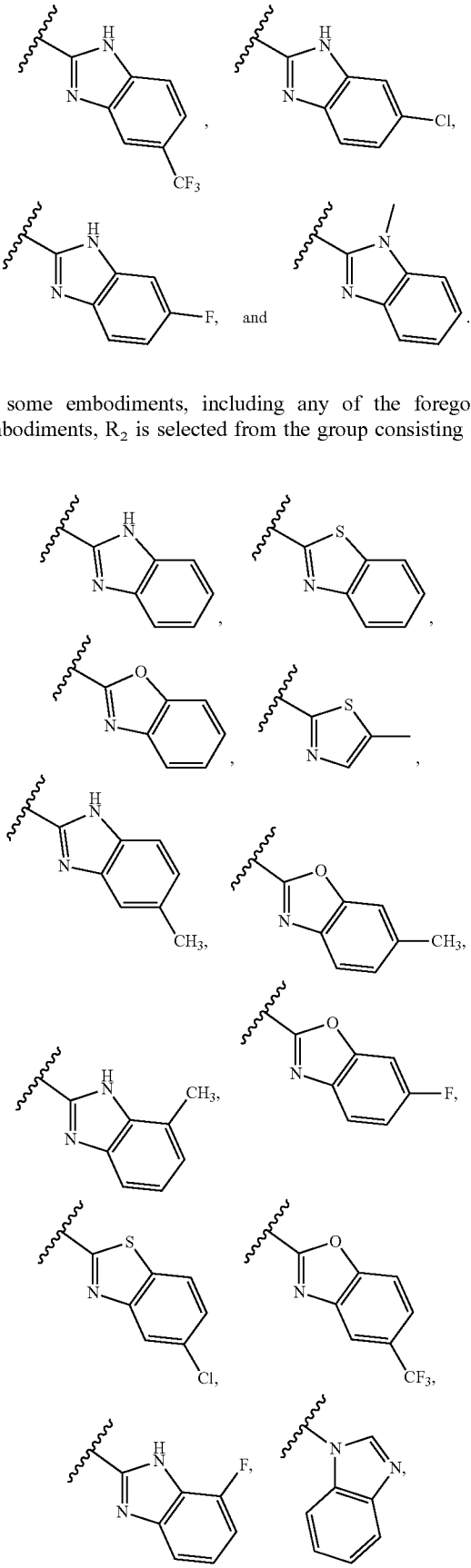
In some embodiments, including any of the foregoing embodiments, $R_2$ is selected from the group consisting of:

-continued
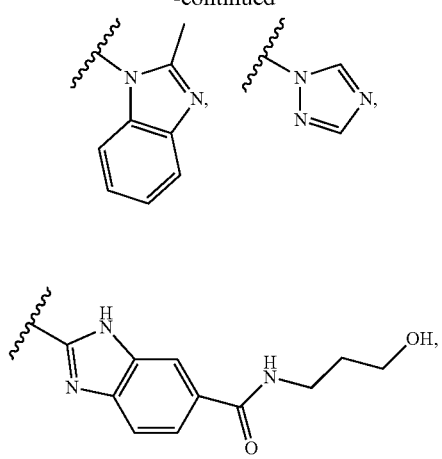
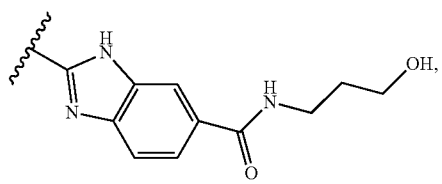
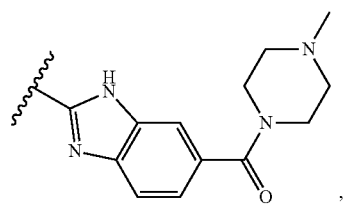
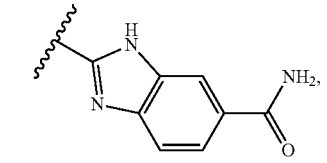
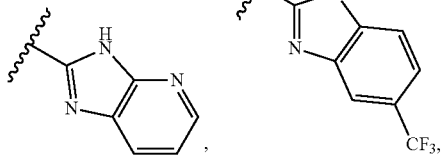, and
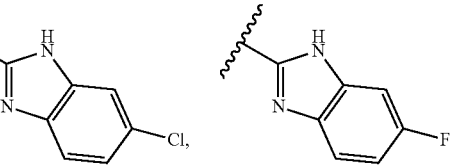.
In some embodiments, including any of the foregoing embodiments, R₂ is selected from the group consisting of:
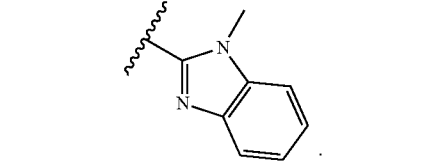
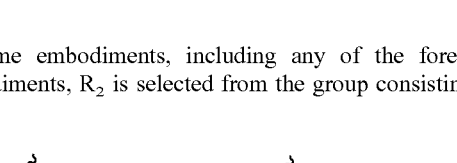
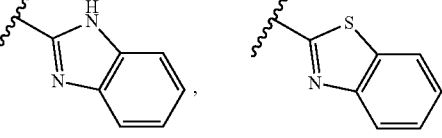

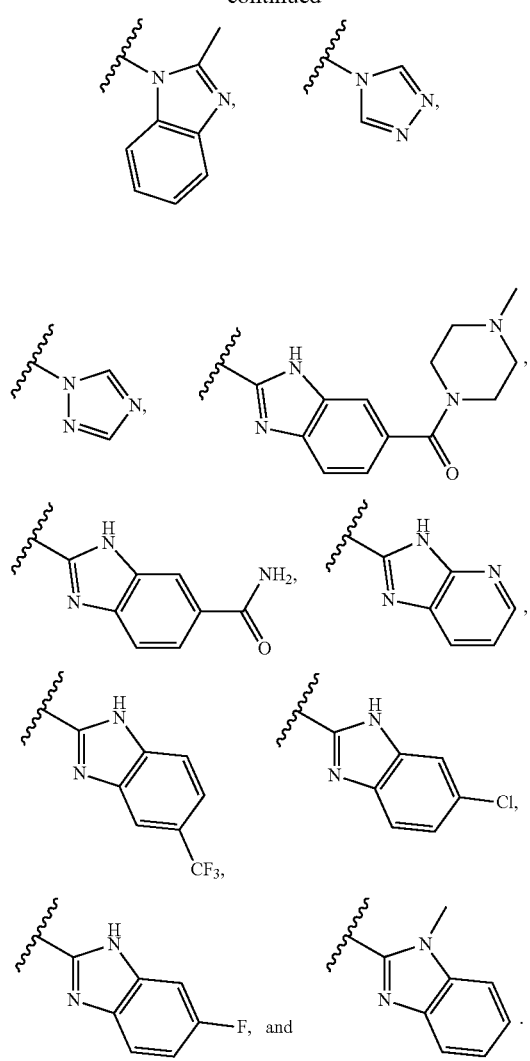
In some embodiments, including any of the foregoing embodiments, $R_2$ is selected from the group consisting of:
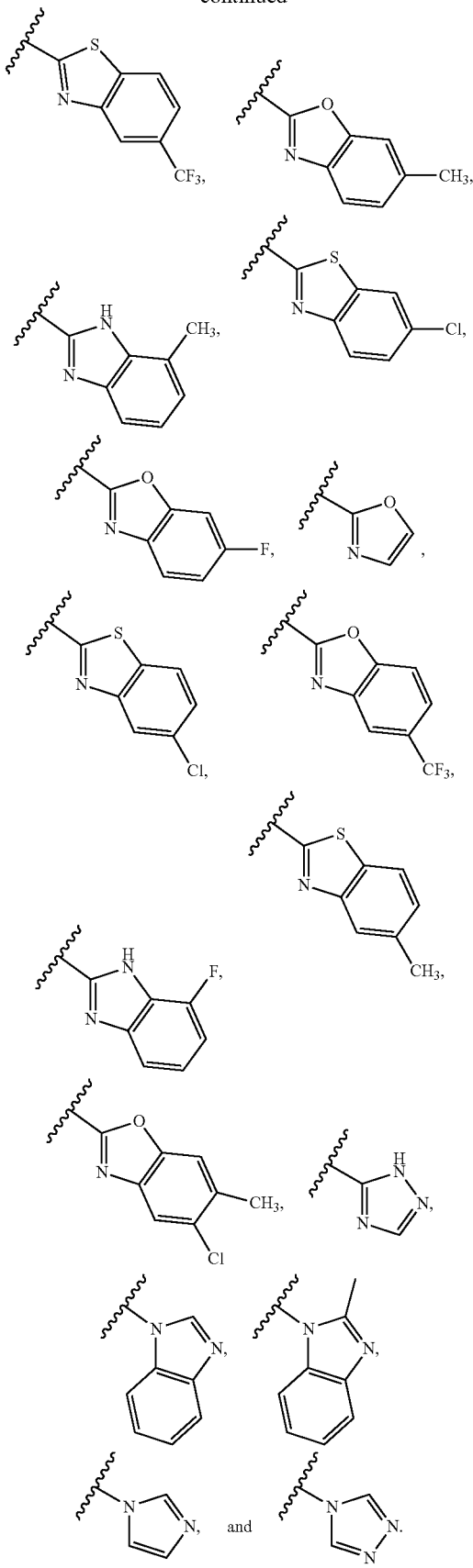

In some embodiments, including any of the foregoing embodiments, $R_2$ is selected from the group consisting of:

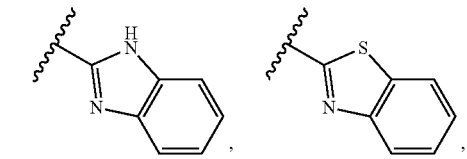

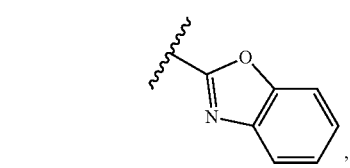

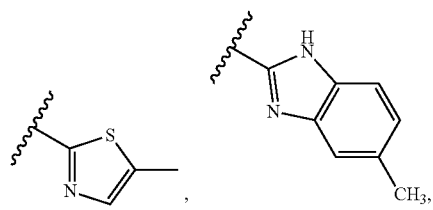

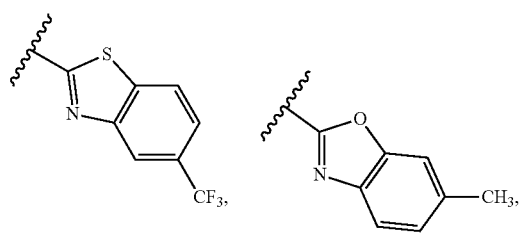

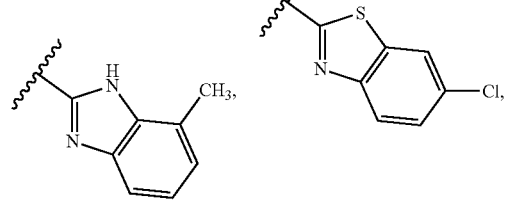

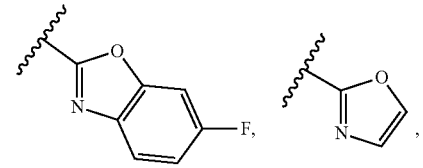

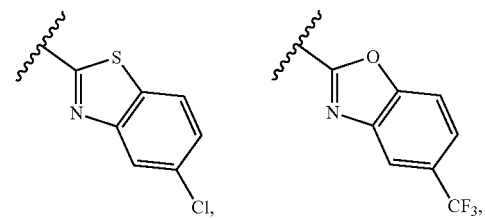

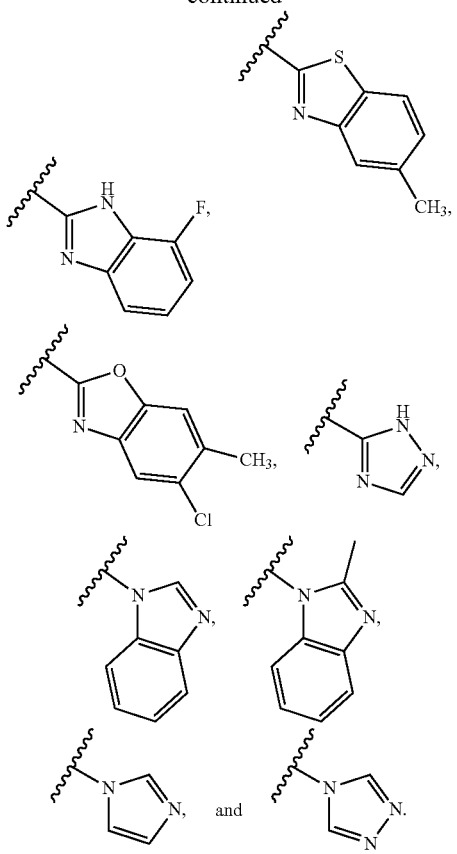

In some embodiments, including any of the foregoing embodiments, the compound is a compound of Formula I, or a stereoisomer, mixture of stereoisomers, solvate, hydrate, or pharmaceutically acceptable salt thereof. In some embodiments, including any of the foregoing embodiments, the compound is a compound of Formula II, or a stereoisomer, mixture of stereoisomers, solvate, hydrate, pharmaceutically acceptable salt or prodrug ester thereof. In some embodiments, the compound is selected from the group consisting of:

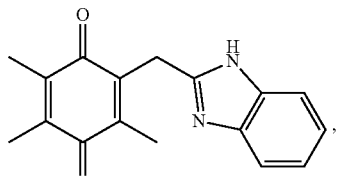

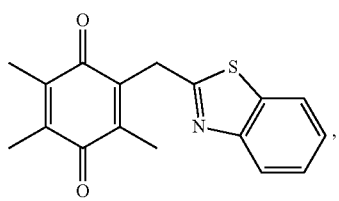

-continued
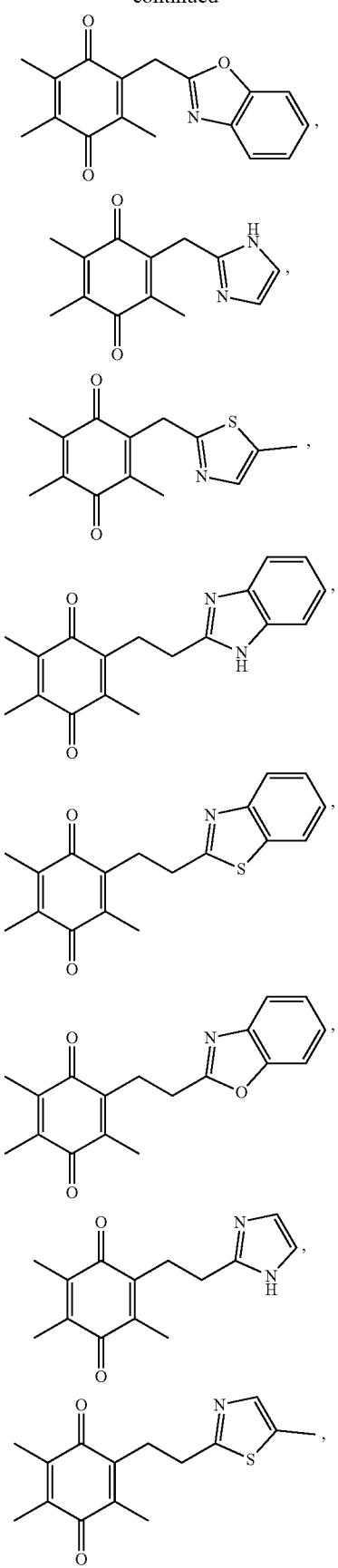
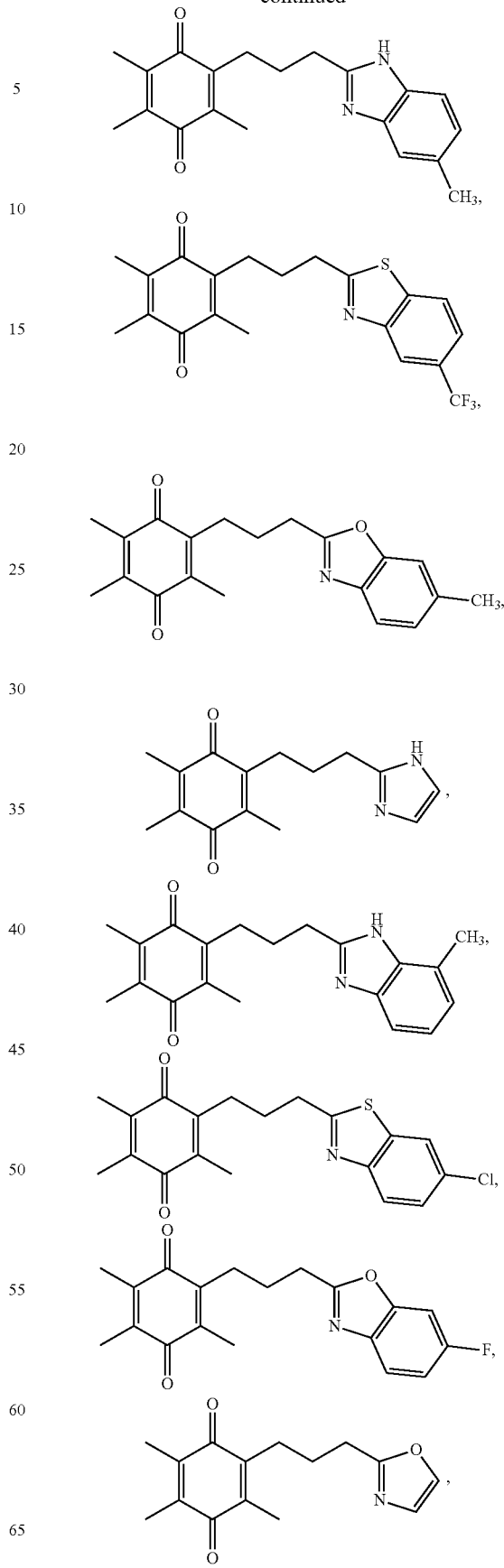

-continued

23
-continued
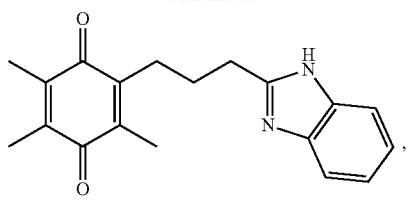
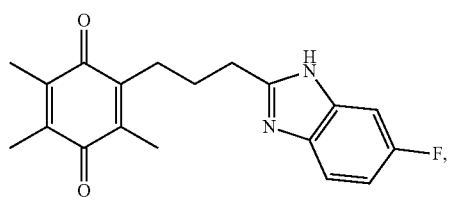
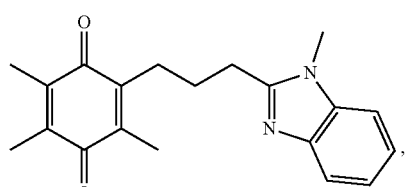
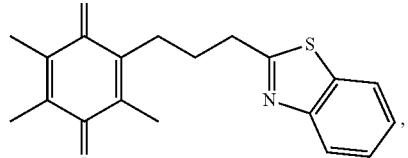
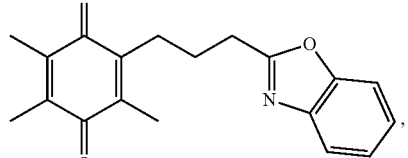
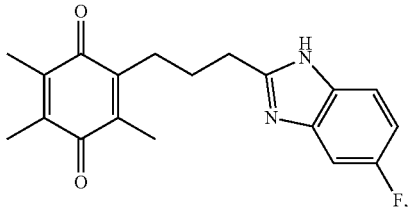
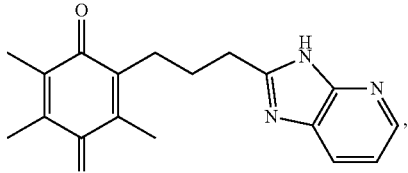
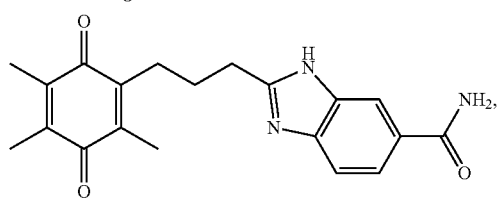
24
-continued
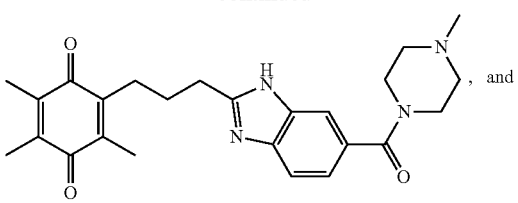, and
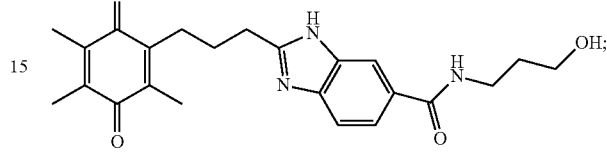
or a stereoisomer, mixture of stereoisomers, solvate, hydrate, pharmaceutically acceptable salt, or prodrug ester thereof. In some embodiments, the compound is selected from the group consisting of:
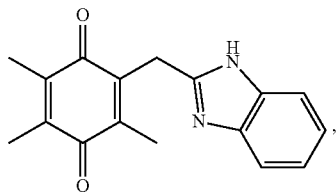
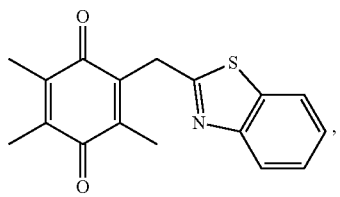
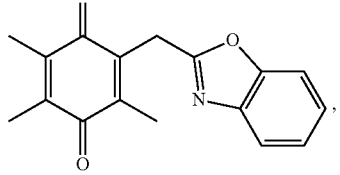
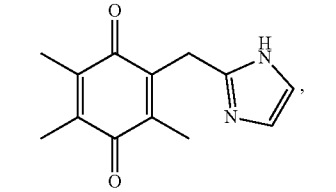
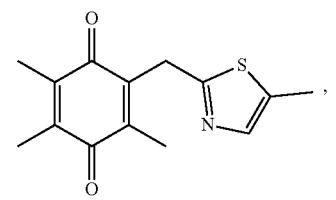

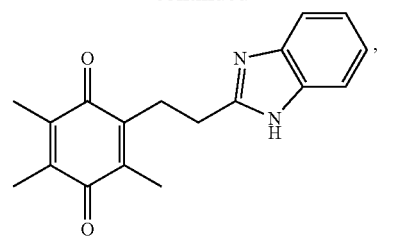
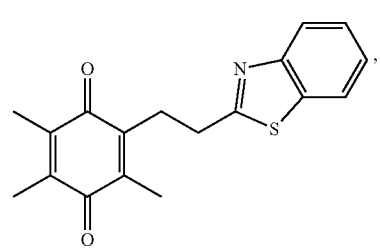
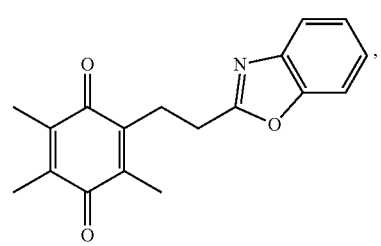
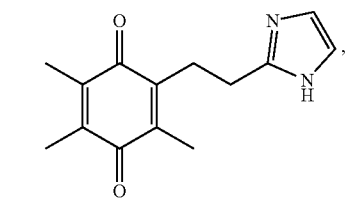
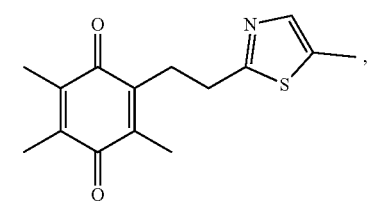
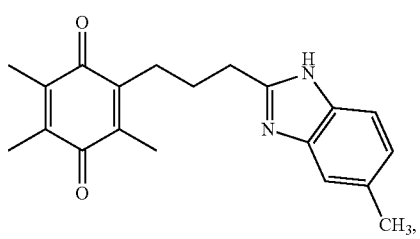
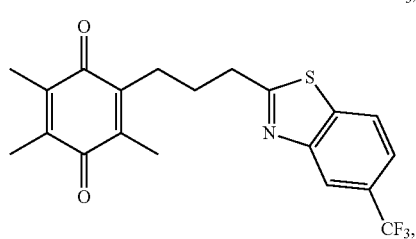
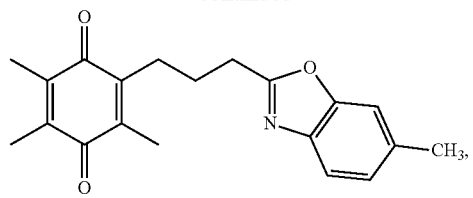
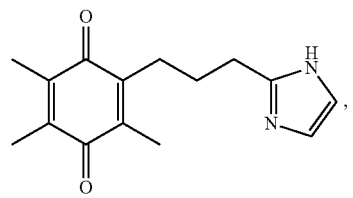
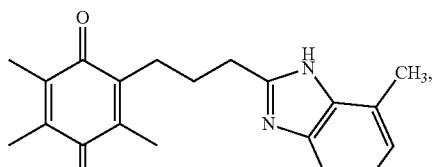
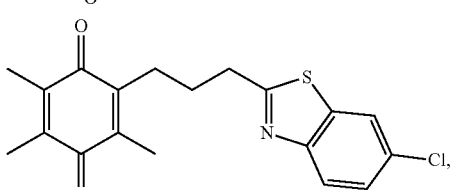
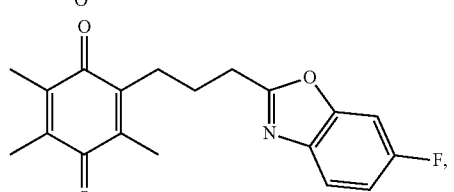
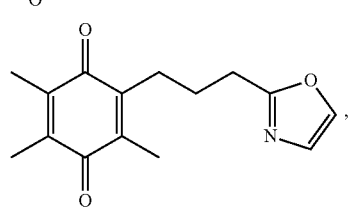
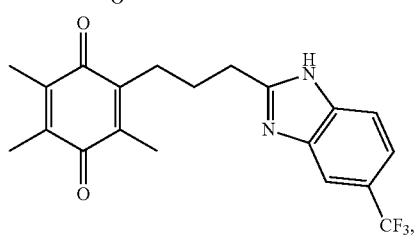
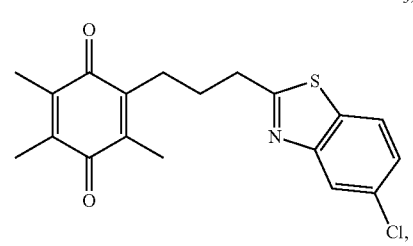

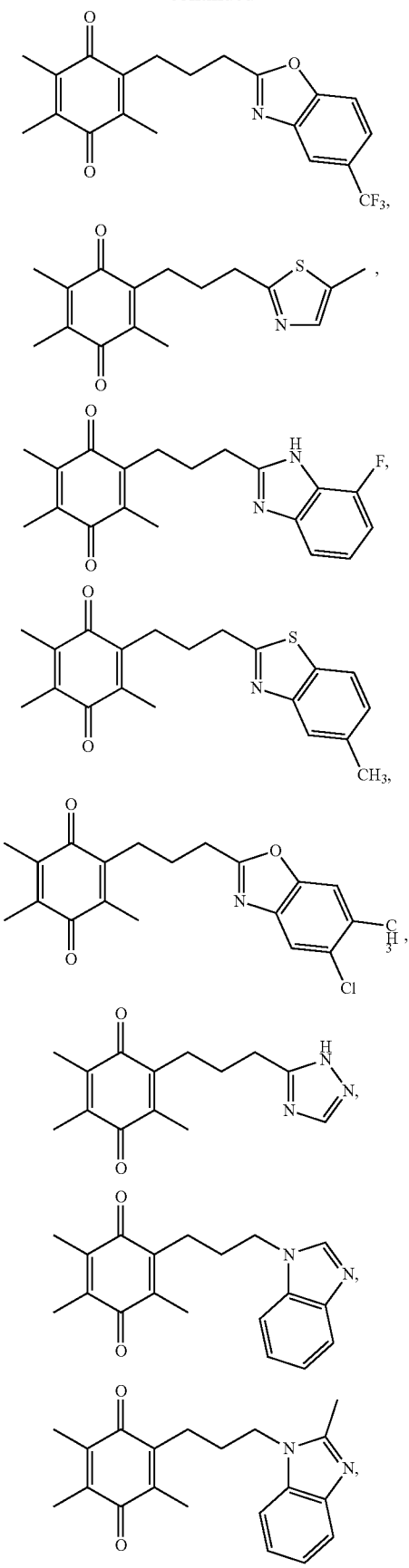
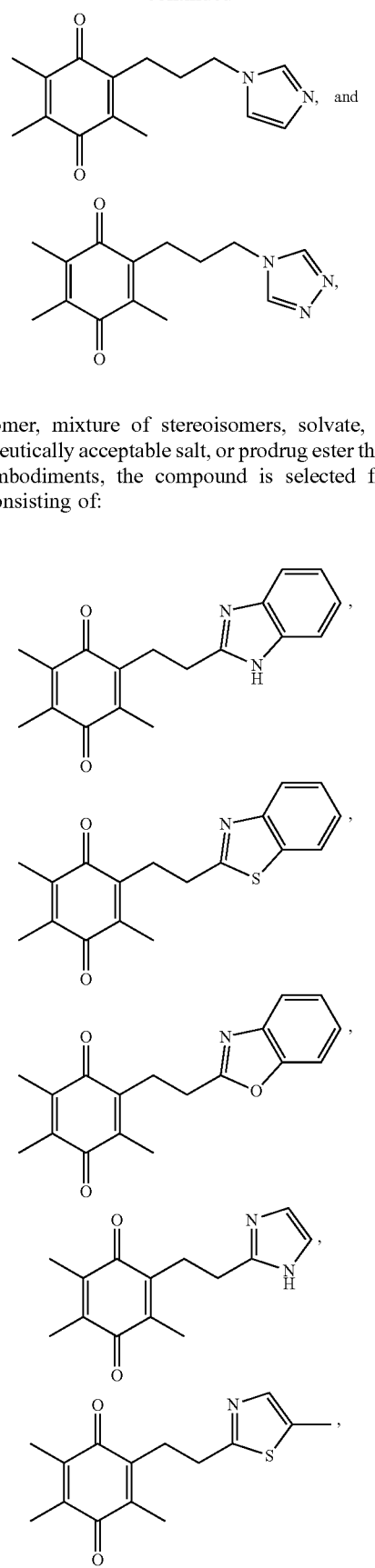
stereoisomer, mixture of stereoisomers, solvate, hydrate, pharmaceutically acceptable salt, or prodrug ester thereof. In some embodiments, the compound is selected from the group consisting of:

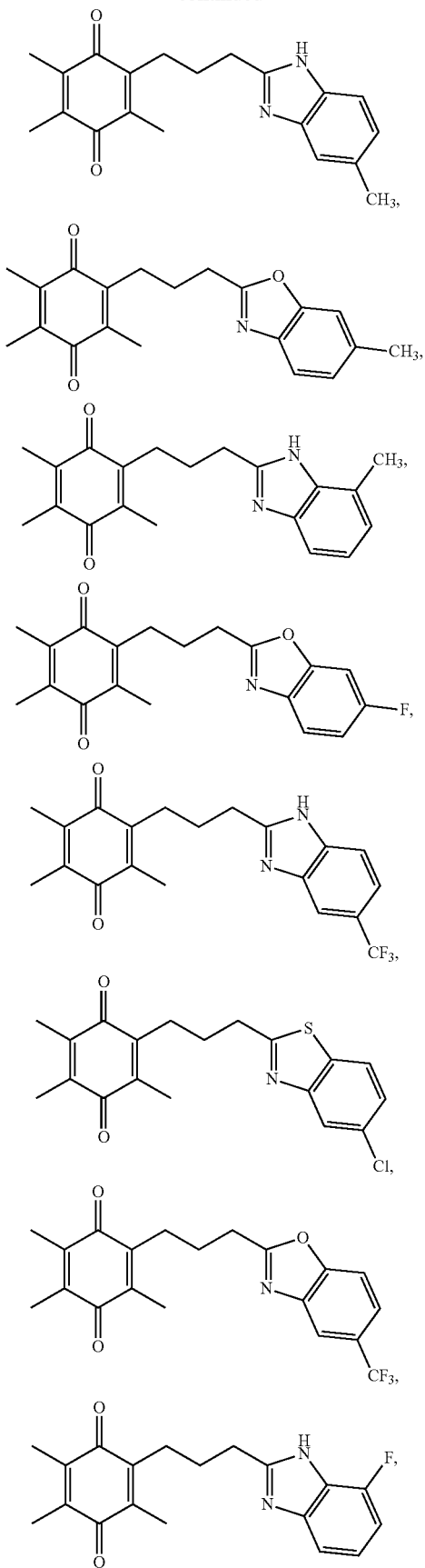
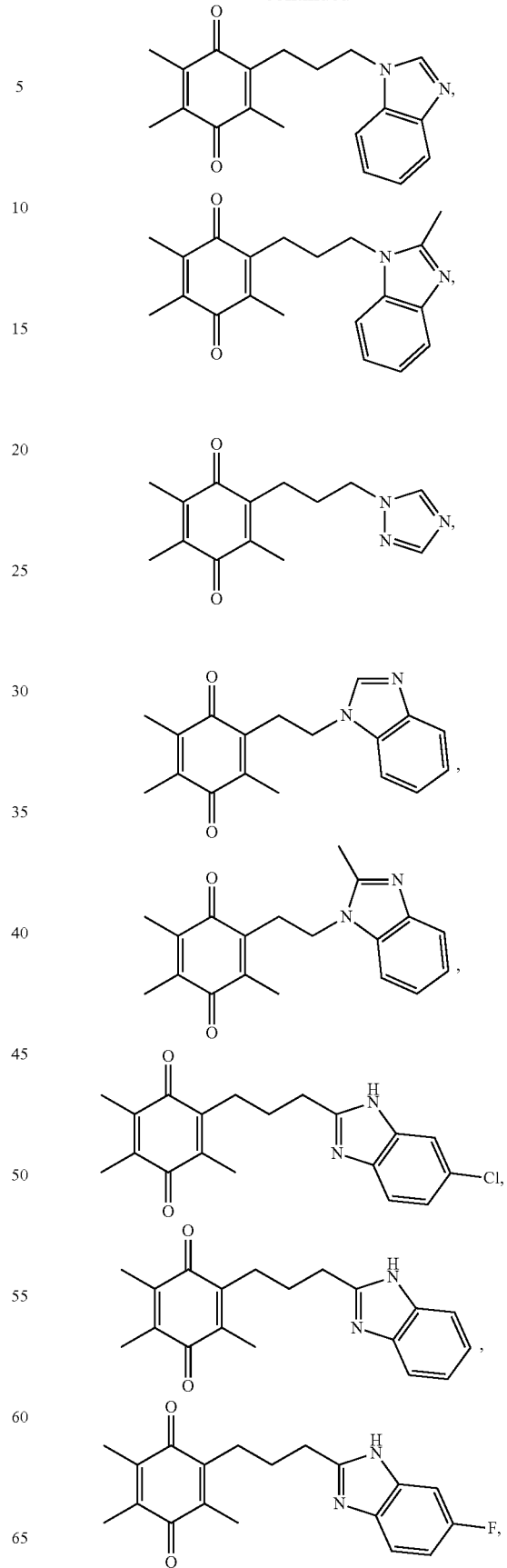

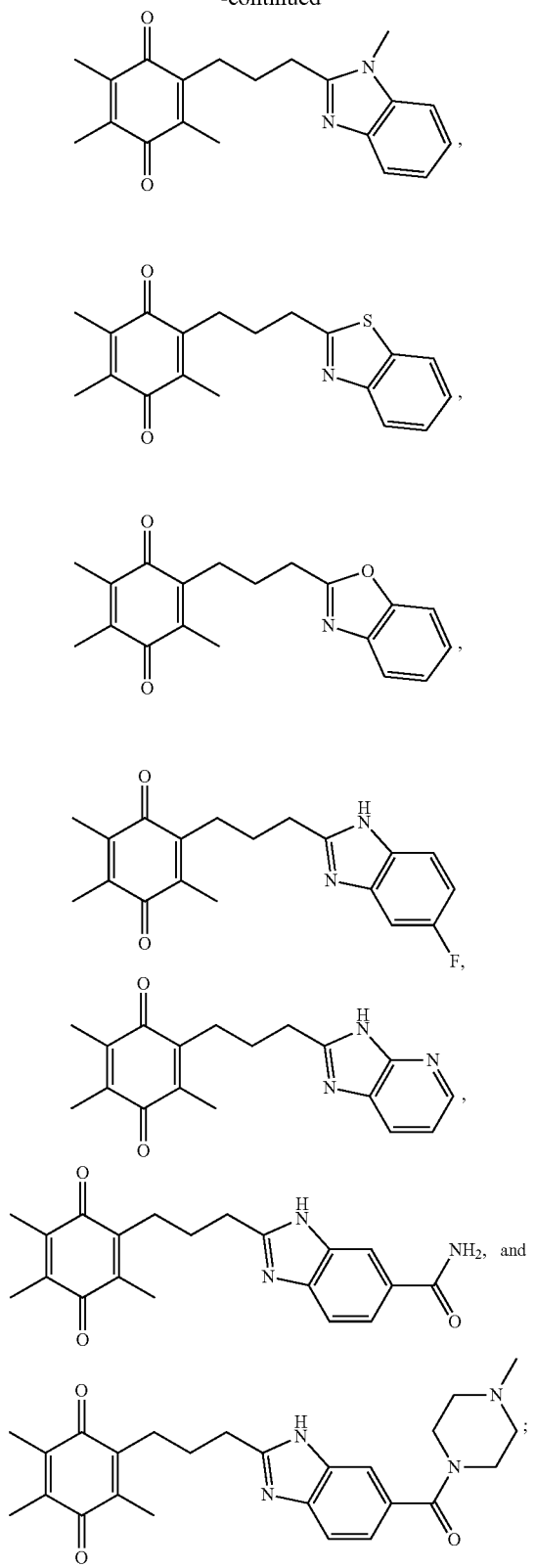

or a stereoisomer, mixture of stereoisomers, solvate, hydrate, pharmaceutically acceptable salt, or prodrug ester thereof. In some embodiments, the compound is selected from the group consisting of:

or a stereoisomer, mixture of stereoisomers, solvate, hydrate, pharmaceutically acceptable salt, or prodrug ester thereof. In some embodiments, including any of the foregoing embodiments, the compound is an ester prodrug:

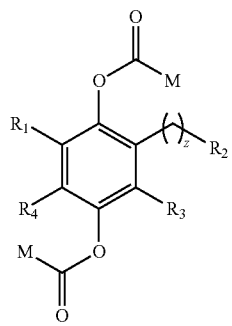

wherein M is $C_1$-$C_6$ alkyl, $C_6$-$C_{20}$ aryl, —O—$C_1$-$C_6$ alkyl, —NH$_2$, —N(H)($C_1$-$C_6$ alkyl), or —N($C_1$-$C_6$ alkyl)($C_1$-$C_6$ alkyl). In some embodiments, including any of the foregoing embodiments, the compound is a compound of Formula I or II, or a stereoisomer, mixture of stereoisomers, solvate, hydrate, or pharmaceutically acceptable salt thereof. In some embodiments, including any of the foregoing embodiments, the compound is a compound of Formula I or II, or a stereoisomer, mixture of stereoisomers, or pharmaceutically acceptable salt thereof. In some embodiments, including any of the foregoing embodiments, the compound is a compound of Formula I or II, or a stereoisomer or mixture of stereoisomers thereof. In some embodiments, including any of the foregoing embodiments, the compound is a compound of Formula I or II, or a pharmaceutically acceptable salt thereof. In some embodiments, including any of the foregoing embodiments, the compound has an $EC_{50}$ of less than about 1 μM, as measured by an assay described in any one of Examples 1-6. In some embodiments, including any of the foregoing embodiments, the compound has an $EC_{50}$ of less than about 500 nM, as measured by an assay described in any one of Examples 1-6. In some embodiments, including any of the foregoing embodiments, the compound has an $EC_{50}$ of less than about 250 nM, as measured by an assay described in any one of Examples 1-6. The compound of the invention can be any individual compound of Formula I or II, or a stereoisomer, mixture of stereoisomers, solvate, hydrate, pharmaceutically acceptable salt or prodrug ester thereof, as described herein. Compositions comprising combinations of compounds of the invention are also contemplated. Non-limiting examples of compounds of the invention are described in Examples A and B.

In another aspect of the invention is a pharmaceutical formulation comprising a compound as described herein and a pharmaceutically acceptable excipient.

In another aspect of the invention is a pharmaceutical formulation comprising an active agent and a pharmaceutically acceptable excipient, wherein the active agent consists of, or consists essentially of, a compound as described herein.

In another aspect of the invention is a method of treating or suppressing an oxidative stress disorder, modulating one or more energy biomarkers, normalizing one or more energy biomarkers, or enhancing one or more energy biomarkers, comprising administering to a subject a therapeutically effective amount or effective amount of a compound of Formula (I) or Formula (II):

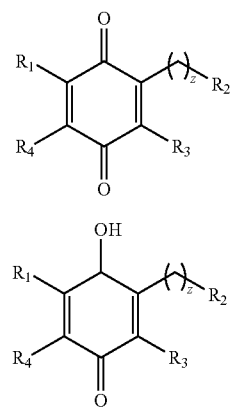

wherein: $R_1$, $R_3$ and $R_4$ are independently $C_1$-$C_6$ alkyl or —O—$C_1$-$C_6$ alkyl; $R_2$ is heteroaryl optionally substituted with one or two substituents independently selected from the group consisting of —CH$_3$, —CF$_3$, halo, —OCH$_3$, and —C(O)—N(R$_5$)(R$_6$), wherein the substituents are independently linked to the heteroaryl by either a —C— or —N— within the heteroaryl; $R_5$ and $R_6$ are independently selected from the group consisting of —H, —$C_1$-$C_6$ alkyl, and —$C_1$-$C_6$ alkyl-hydroxy, or wherein $R_5$ and $R_6$ together with the N to which they are attached form a saturated or unsaturated 3-8 membered ring, optionally incorporating one, two, or three additional heteroatoms each independently selected from the group consisting of N, O, and S, and wherein the ring is optionally substituted with —$C_1$-$C_6$ alkyl; and z is 1, 2, 3, 4, 5, or 6; or a stereoisomer, mixture of stereoisomers, solvate, hydrate, pharmaceutically acceptable salt or prodrug ester thereof; with the proviso that when the compound is:

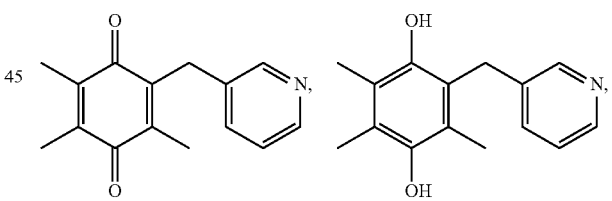

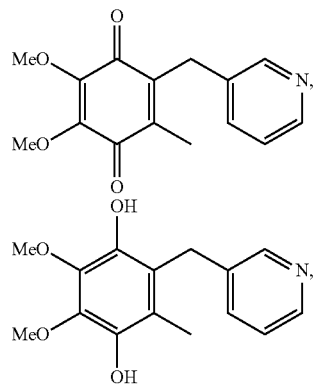

-continued

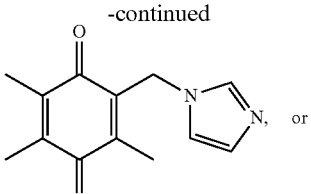, or

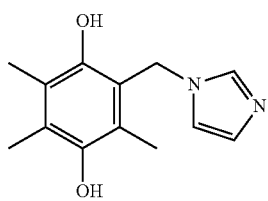

or a stereoisomer, mixture of stereoisomers, solvate, hydrate, pharmaceutically acceptable salt or prodrug ester thereof, then the oxidative stress disorder is not stroke, ischemia, or cancer. In some embodiments, the compound of Formula (I) or Formula (II) has the formula:

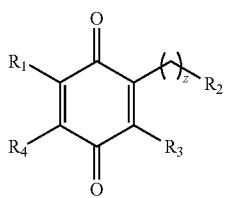

Formula I

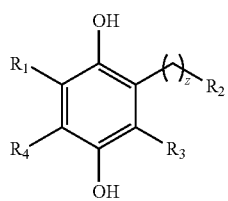

Formula II wherein: $R_1$, $R_3$ and $R_4$ are independently $C_1$-$C_6$ alkyl or —O—$C_1$-$C_6$ alkyl; $R_2$ is heteroaryl optionally substituted with one or two substituents independently selected from the group consisting of —$CH_3$, —$CF_3$, halo, and —$OCH_3$, wherein the substituents are independently linked to the heteroaryl by either a —C— or —N— within the heteroaryl; and z is 1, 2, 3, 4, 5, or 6; or a stereoisomer, mixture of stereoisomers, solvate, hydrate, pharmaceutically acceptable salt or prodrug ester thereof; with the proviso that when the compound is:

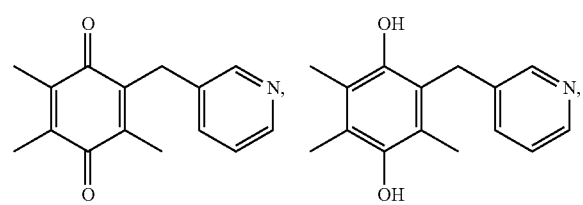

-continued

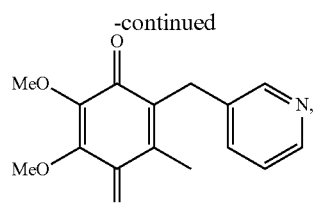

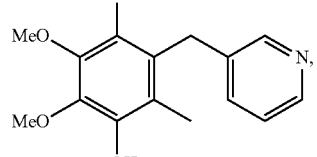

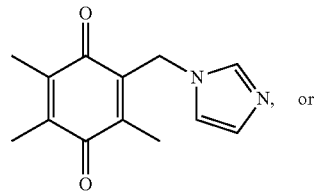, or

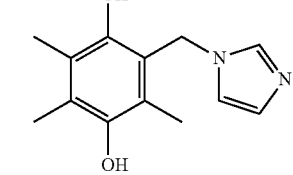

or a stereoisomer, mixture of stereoisomers, solvate, hydrate, pharmaceutically acceptable salt or prodrug ester thereof, then the oxidative stress disorder is not stroke, ischemia, or cancer. In some embodiments, including any of the foregoing embodiments, z is 2, 3, 4, 5, or 6. In some embodiments, including any of the foregoing embodiments, z is 1, 2, or 3. In some embodiments, including any of the foregoing embodiments, z is 2 or 3. In some embodiments, including any of the foregoing embodiments, z is 1. In some embodiments, including any of the foregoing embodiments, z is 2. In some embodiments, including any of the foregoing embodiments, z is 3. In some embodiments, including any of the foregoing embodiments, z is 4. In some embodiments, including any of the foregoing embodiments, z is 5. In some embodiments, including any of the foregoing embodiments, z is 6. In some embodiments, including any of the foregoing embodiments, $R_1$, $R_3$ and $R_4$ are independently $C_1$-$C_6$ alkyl. In some embodiments, including any of the foregoing embodiments, $R_1$, $R_3$ and $R_4$ are independently $C_1$-$C_4$ alkyl. In some embodiments, including any of the foregoing embodiments, $R_1$, $R_3$ and $R_4$ are independently $C_1$-$C_2$ alkyl. In some embodiments, including any of the foregoing embodiments, $R_1$, $R_3$ and $R_4$ are —$CH_3$. In some embodiments, including any of the foregoing embodiments, $R_1$ and $R_4$ are independently —O—$C_1$-$C_4$ alkyl, and $R_3$ is $C_1$-$C_4$ alkyl. In some embodiments, including any of the foregoing embodiments, $R_1$ and $R_4$ are independently —O—$C_1$-$C_2$ alkyl, and $R_3$ is $C_1$-$C_4$ alkyl. In some embodiments, including any of the foregoing embodiments, $R_1$, $R_3$ and $R_4$ are —$OCH_3$. In some embodiments, including any of the foregoing embodiments, $R_1$ and $R_4$ are —$OCH_3$, and $R_3$ is —$CH_3$. In some embodiments, $R_1$, $R_3$ and $R_4$ are —$CH_3$; and z is 1, 2, or 3. In some embodiments, $R_1$, $R_3$ and $R_4$ are —$CH_3$; and z is 2 or 3. In some embodiments, including any of the foregoing embodiments, the heteroaryl is selected from the group consisting of: benzoimidazole, benzothiazole, benzoxazole, thiazole, oxazole, imidazole, and triazole. In some embodiments, including any of the foregoing embodiments, the heteroaryl is selected from the group consisting of: benzoimidazole, benzothiazole, benzoxazole, thiazole, oxazole, and triazole. In some embodiments, including any of the foregoing embodiments, the heteroaryl is not pyridine. In some embodiments, including any of the foregoing embodiments, the heteroaryl is not imidazole. In some embodiments, including any of the foregoing embodiments, $R_2$ is unsubstituted. In some embodiments, including any of the foregoing embodiments, $R_2$ is substituted with a single substituent. In some embodiments, including any of the foregoing embodiments, $R_2$ is substituted with two substituents. In some embodiments, including any of the foregoing embodiments, $R_2$ is selected from the group consisting of:

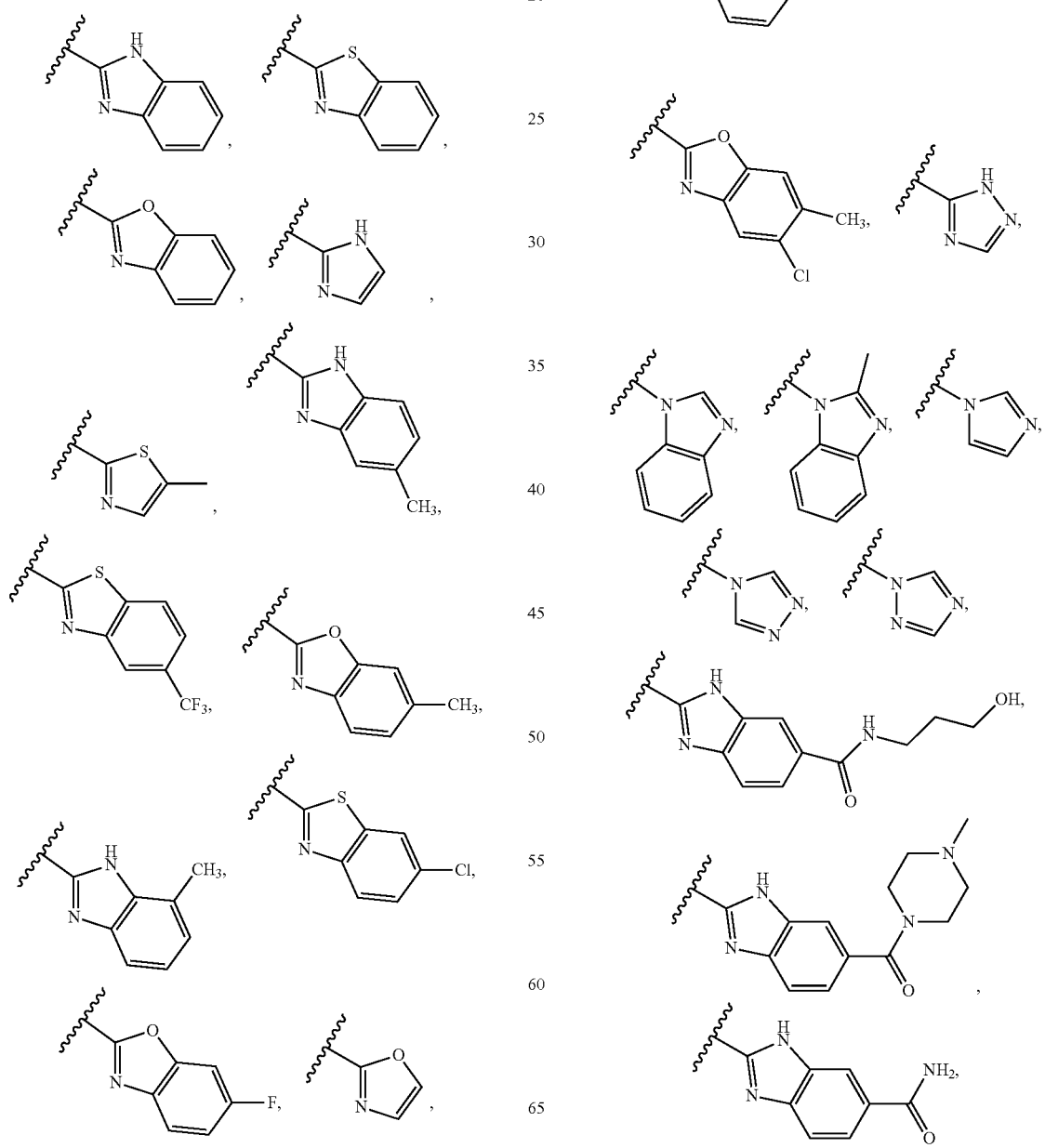

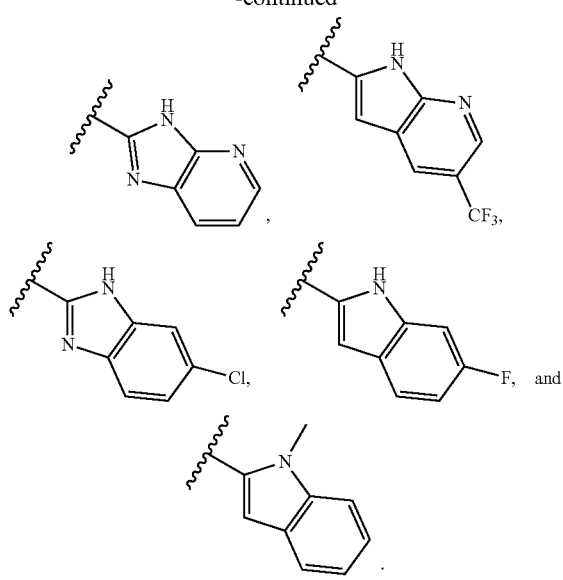
In some embodiments, including any of the foregoing embodiments, R$_2$ is selected from the group consisting of:
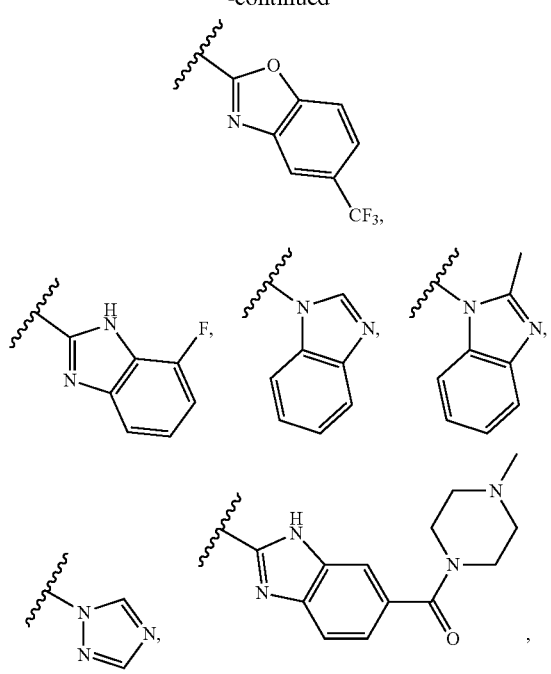
In some embodiments, including any of the foregoing embodiments, R$_2$ is selected from the group consisting of:
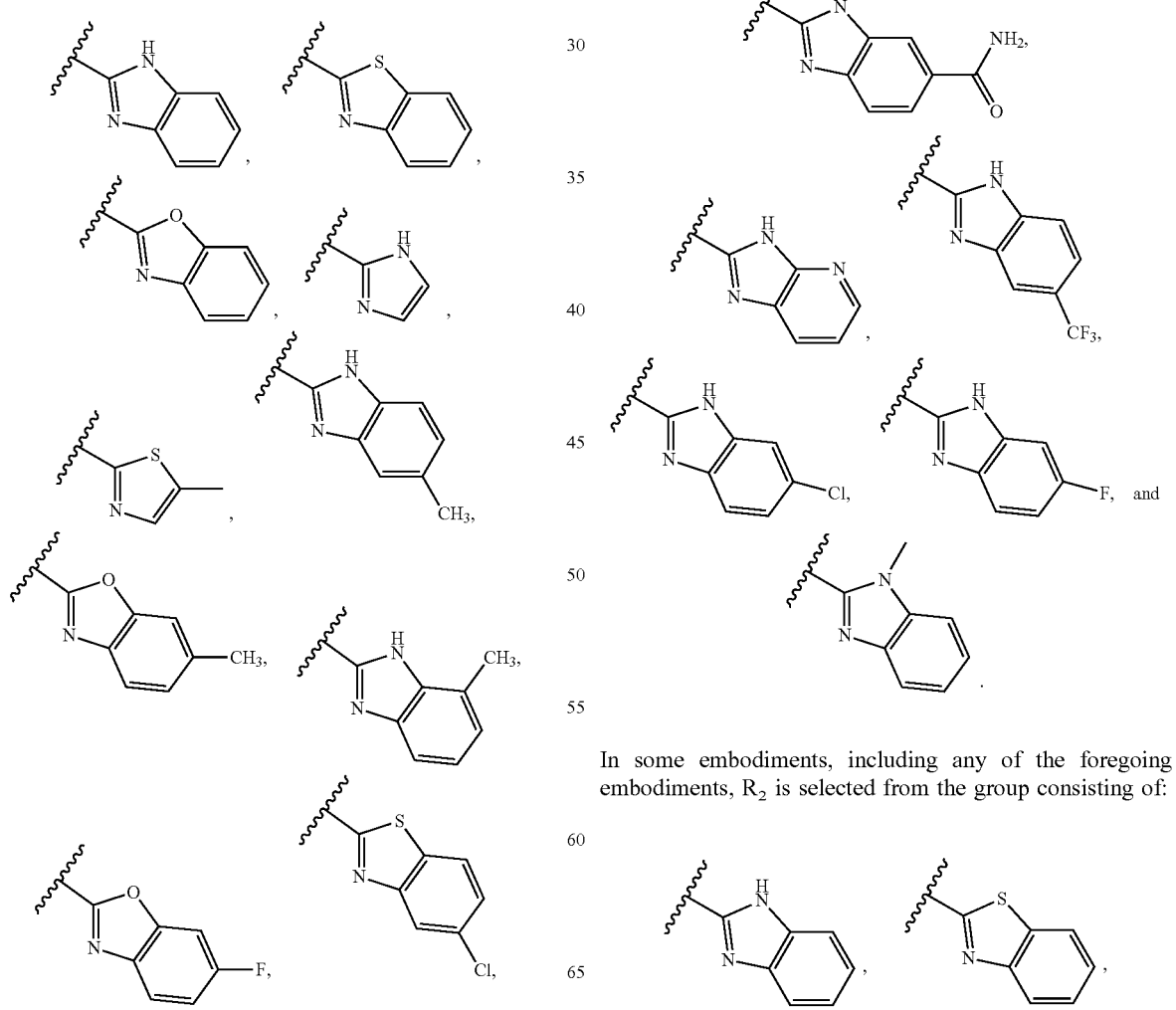

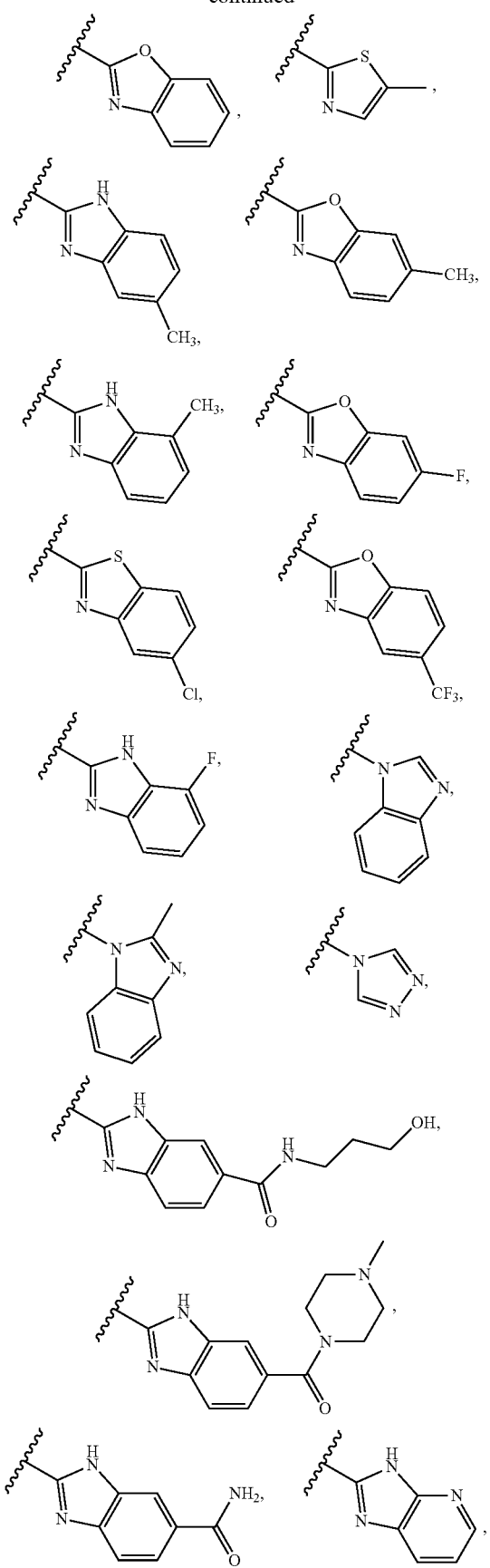
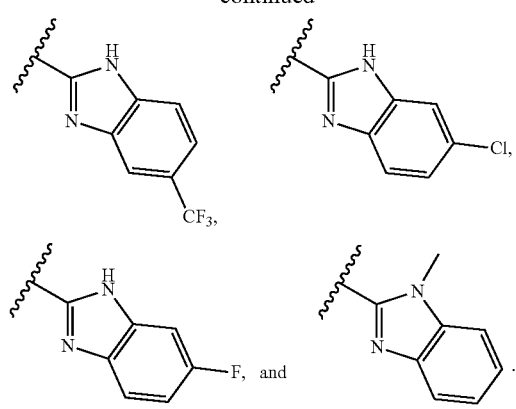
In some embodiments, including any of the foregoing embodiments, R$_2$ is selected from the group consisting of:
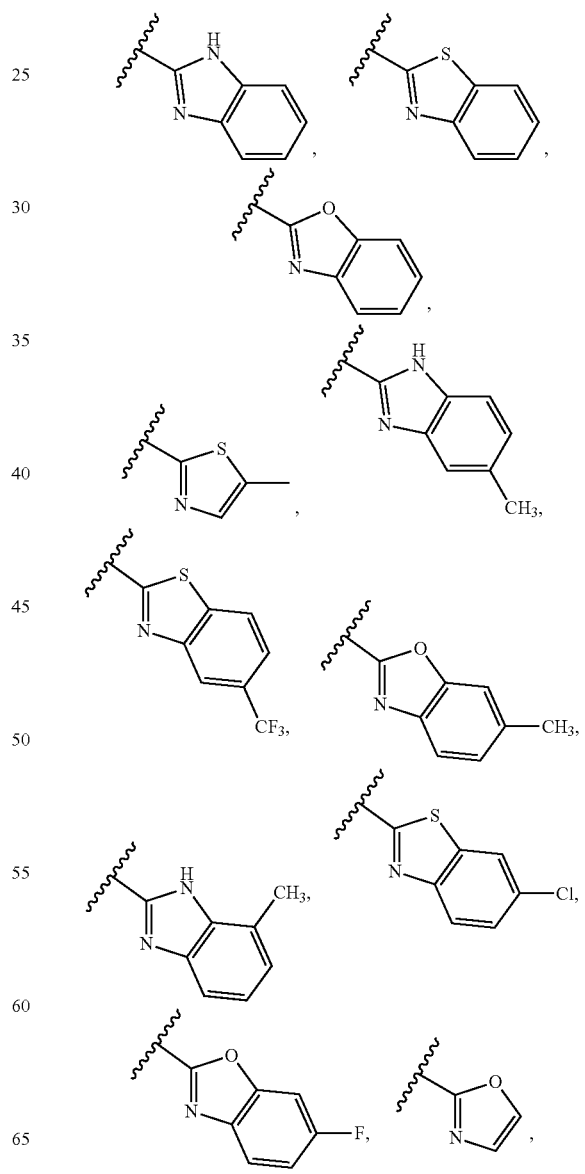

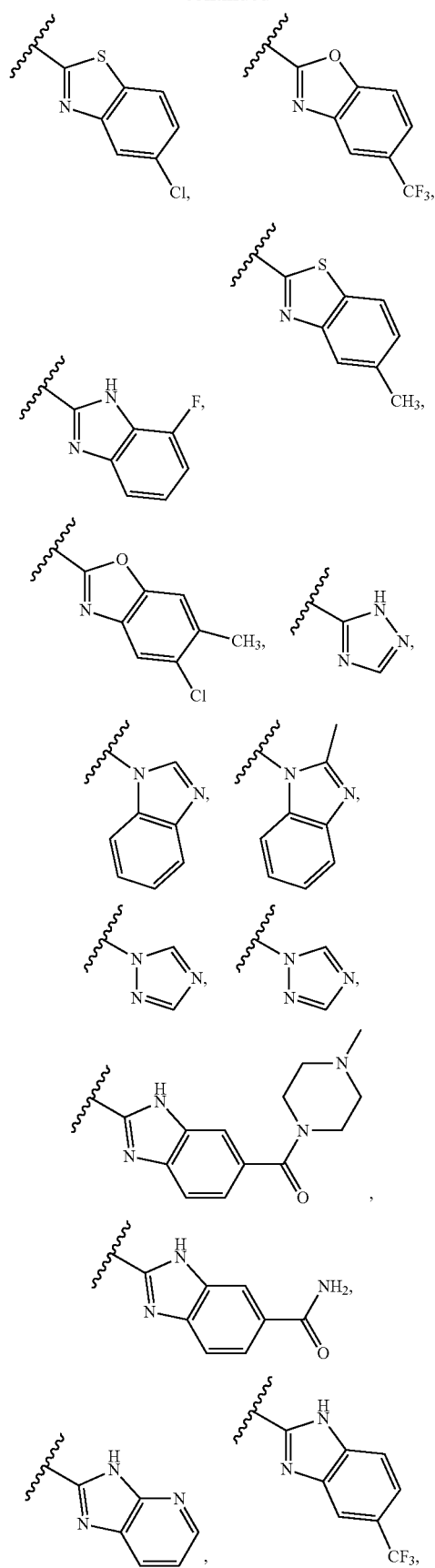
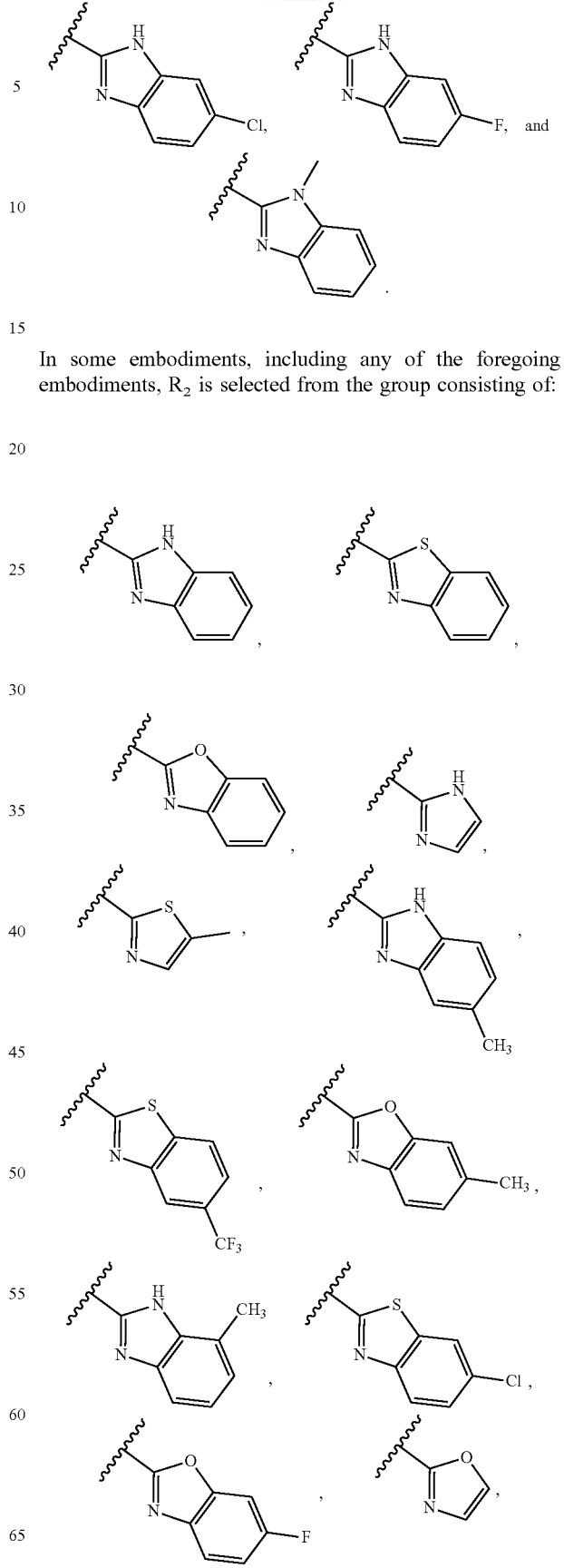
In some embodiments, including any of the foregoing embodiments, R$_2$ is selected from the group consisting of:

-continued
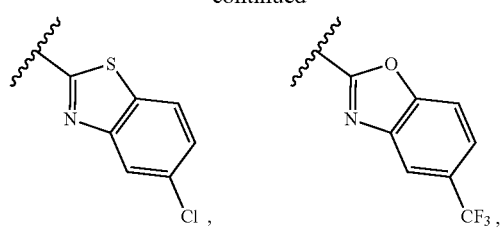
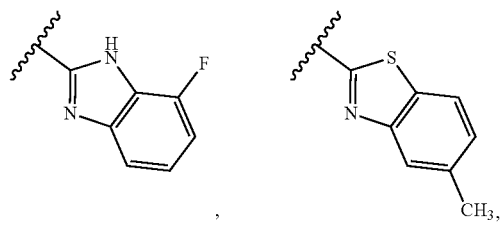
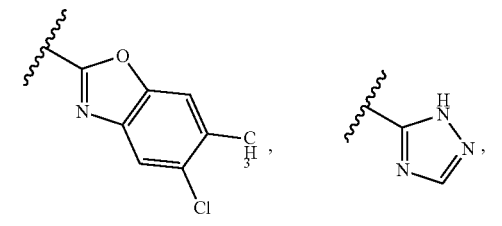
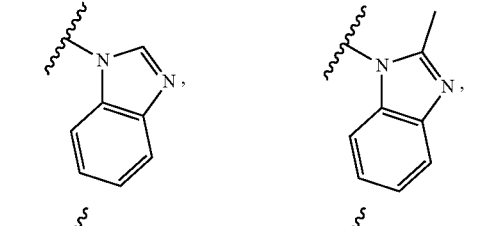
In some embodiments, including any of the foregoing embodiments, R$_2$ is selected from the group consisting of:
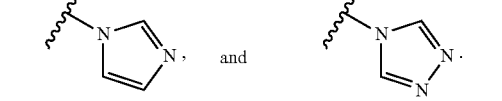
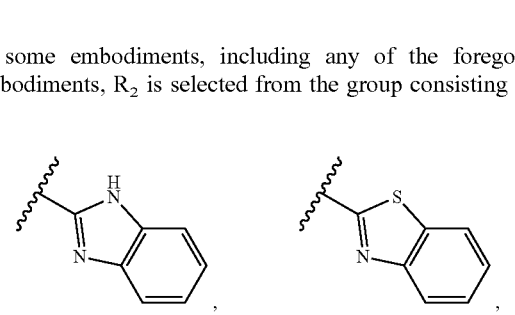
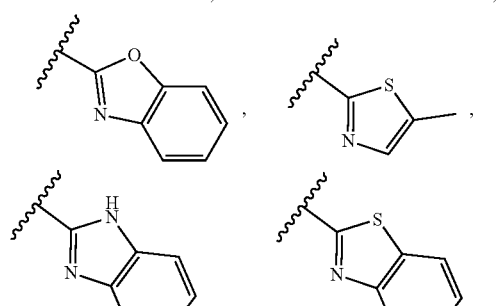
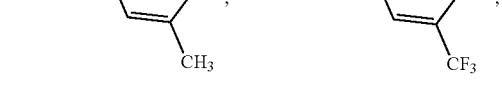
-continued
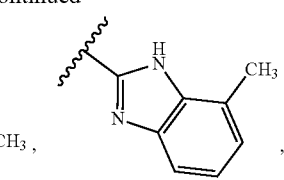
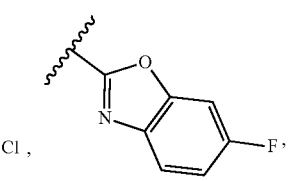
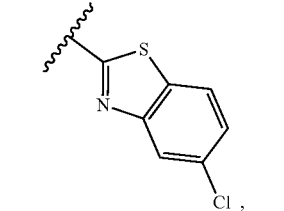
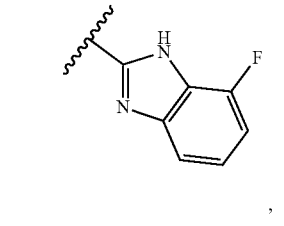
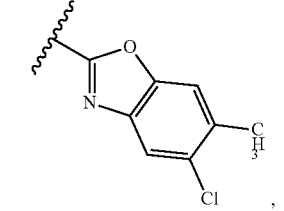
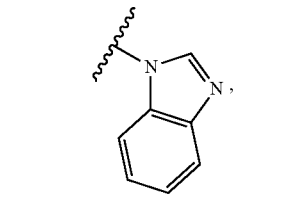
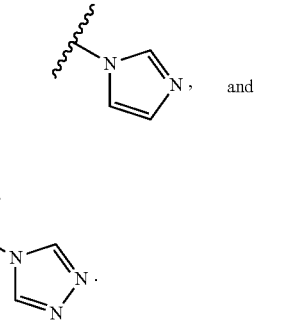
In some embodiments, including any of the foregoing embodiments, the compound is not

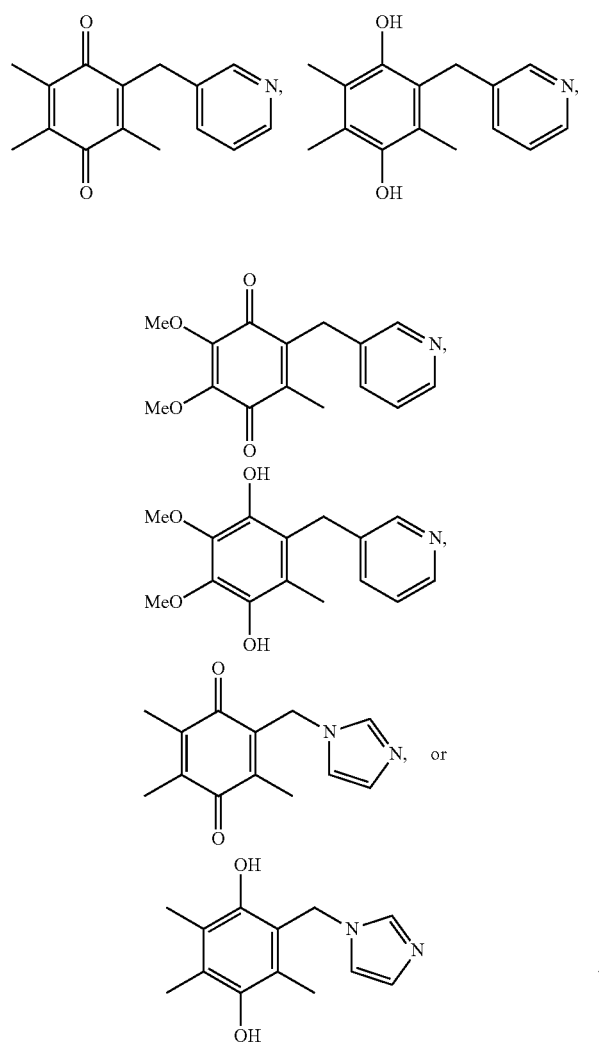

or a stereoisomer, mixture of stereoisomers, solvate, hydrate, pharmaceutically acceptable salt or prodrug ester thereof. In some embodiments, including any of the foregoing embodiments, the compound is a compound of Formula I, or a stereoisomer, mixture of stereoisomers, solvate, hydrate, or pharmaceutically acceptable salt thereof. In some embodiments, including any of the foregoing embodiments, the compound is a compound of Formula II, or a stereoisomer, mixture of stereoisomers, solvate, hydrate, pharmaceutically acceptable salt or prodrug ester thereof. In some embodiments, the compound is selected from the group consisting of:

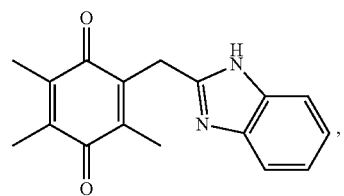

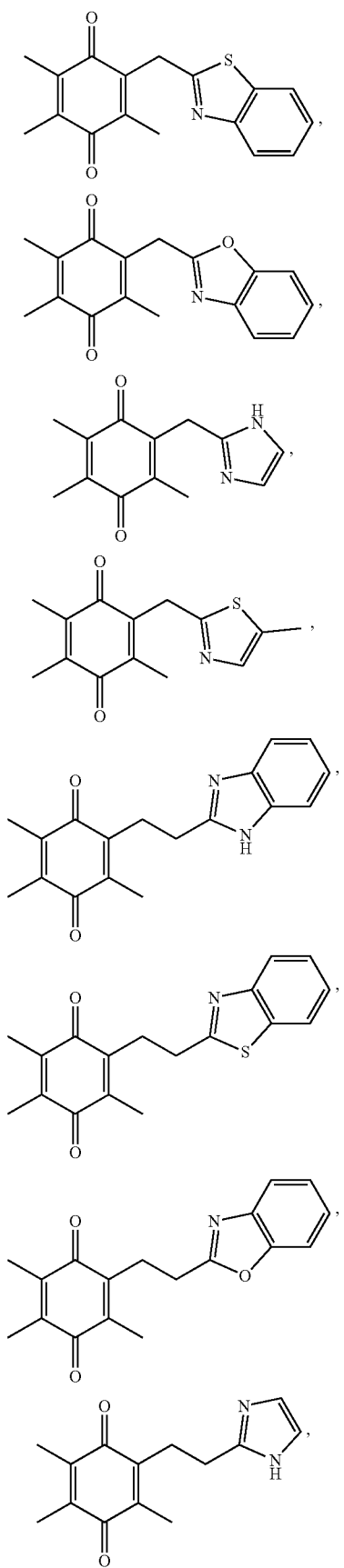

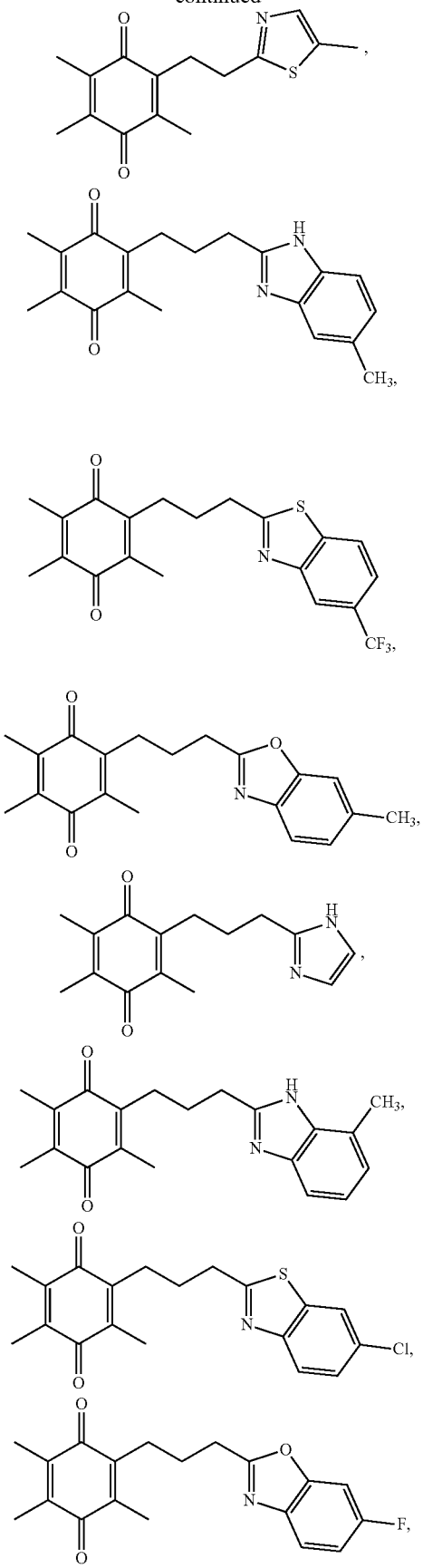
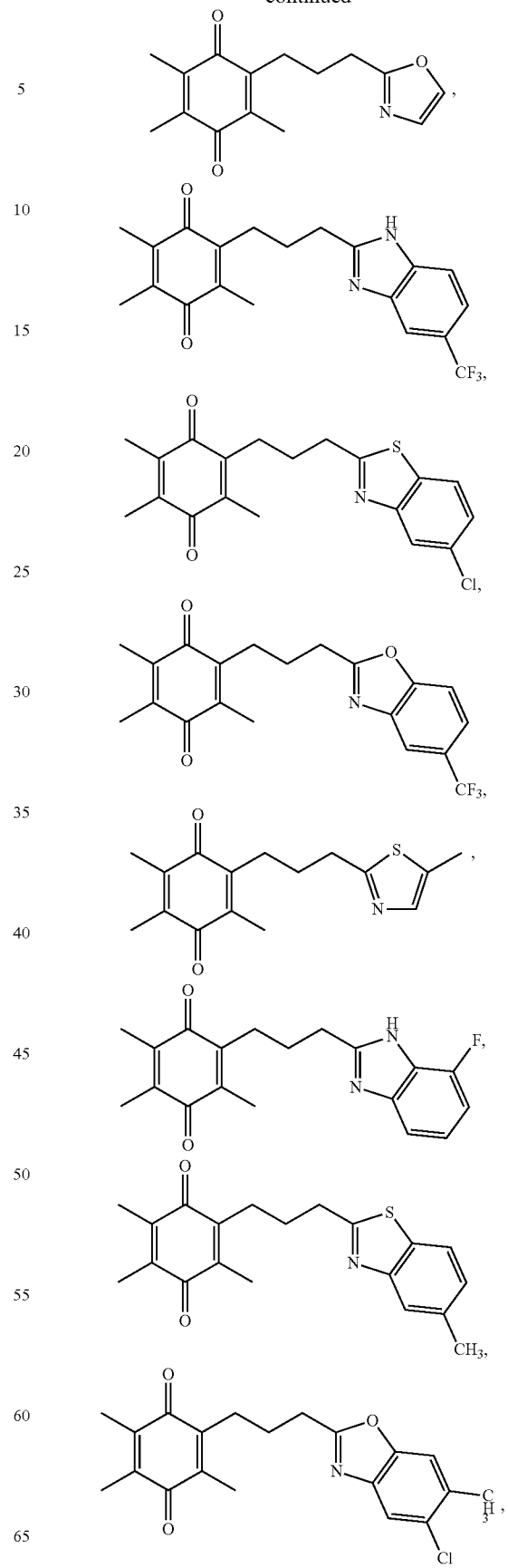

51
-continued
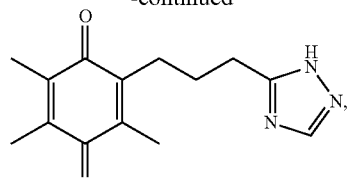
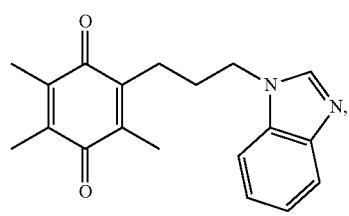
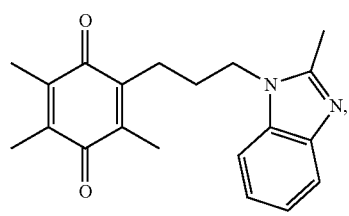
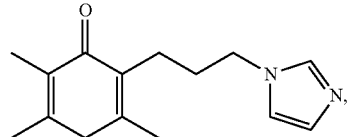
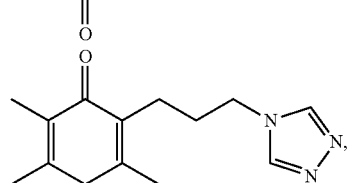
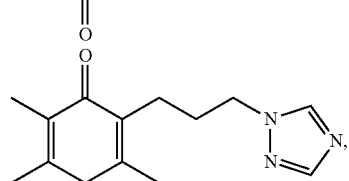
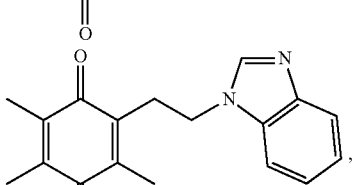
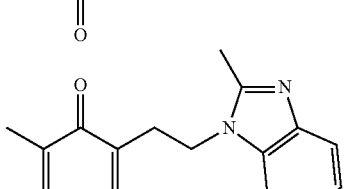
52
-continued
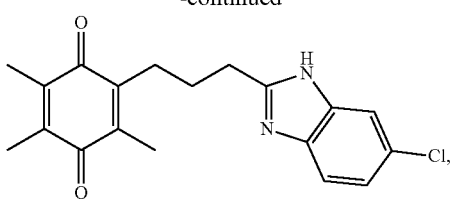

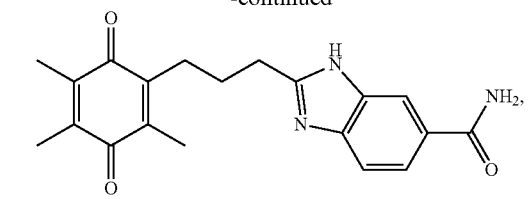
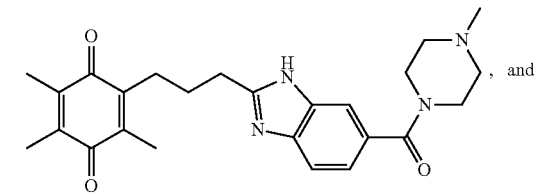, and
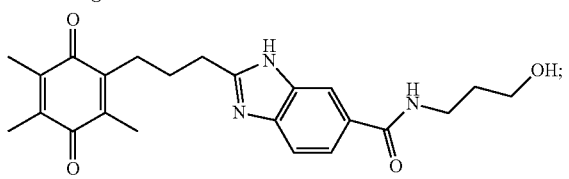
or a stereoisomer, mixture of stereoisomers, solvate, hydrate, pharmaceutically acceptable salt, or prodrug ester thereof. In some embodiments, the compound is selected from the group consisting of:
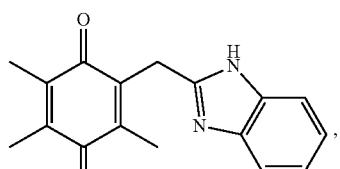
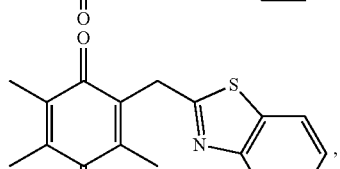
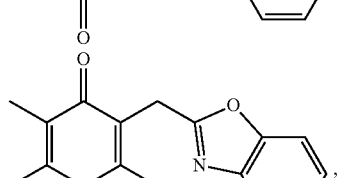
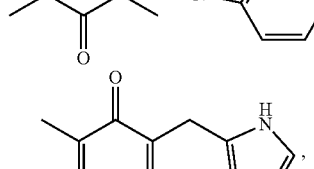
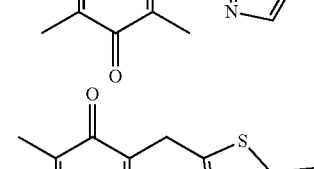
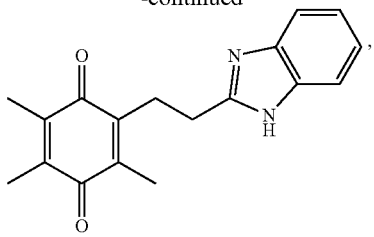
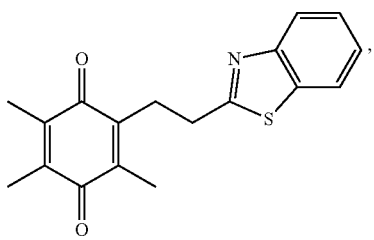
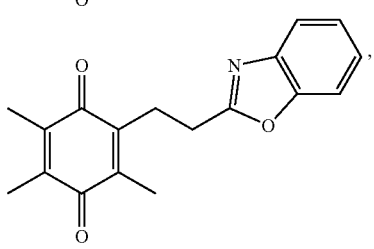
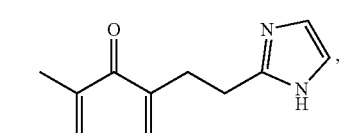
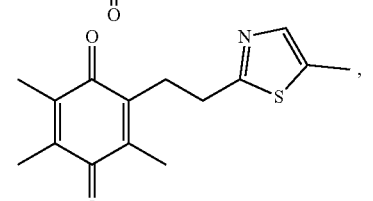
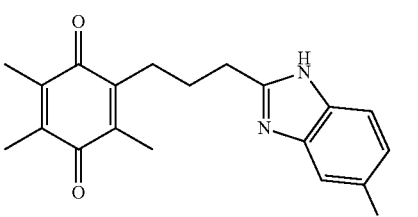
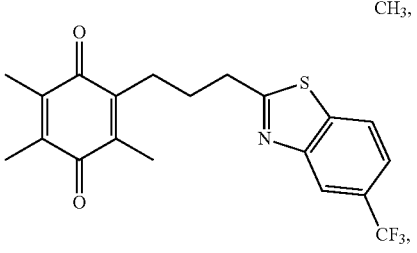

-continued
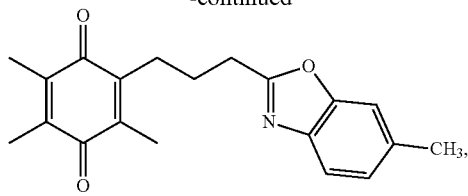
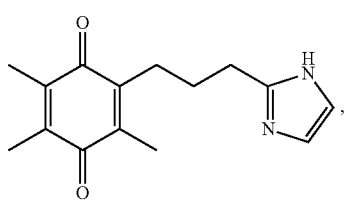
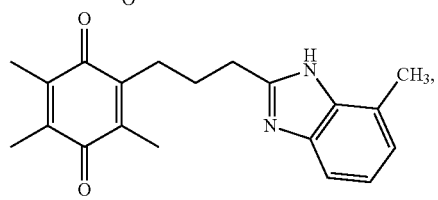
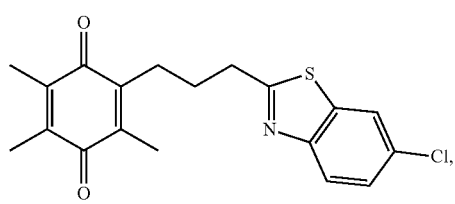
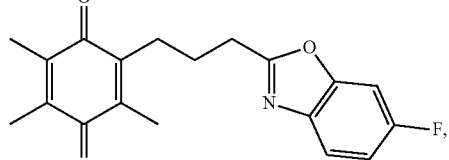
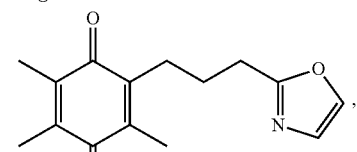
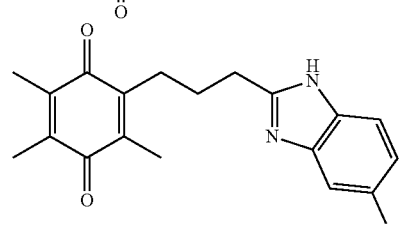
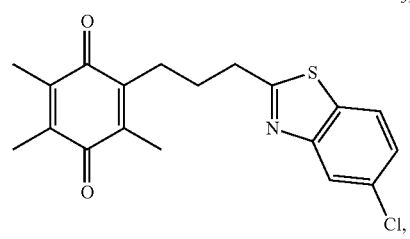
-continued
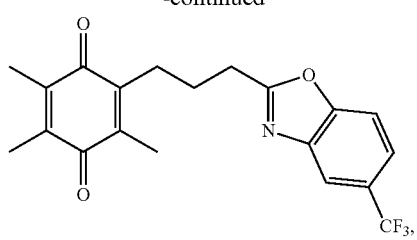
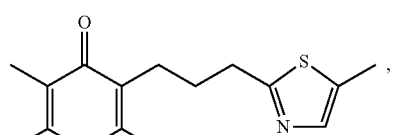
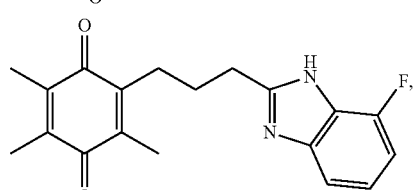
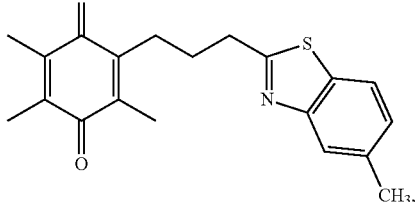
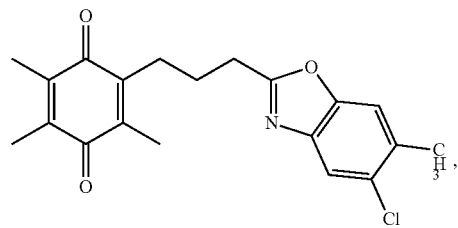
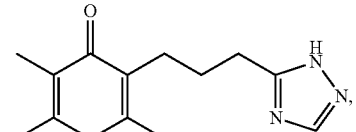
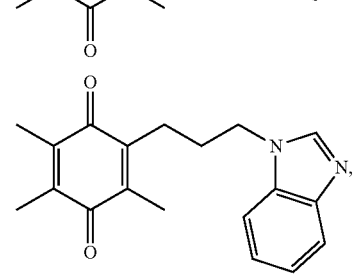
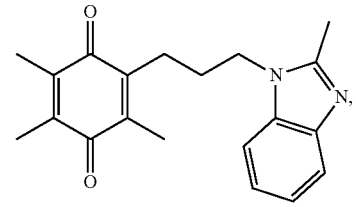

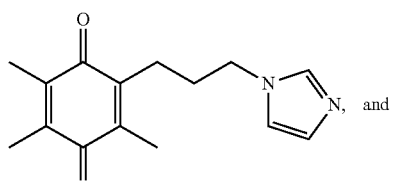, and
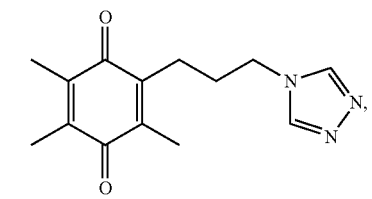
or a stereoisomer, mixture of stereoisomers, solvate, hydrate, pharmaceutically acceptable salt, or prodrug ester thereof. In some embodiments, the compound is selected from the group consisting of:
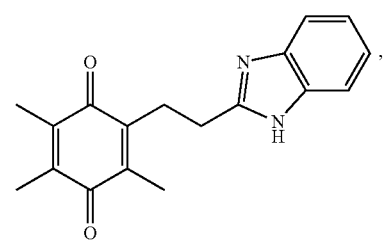,
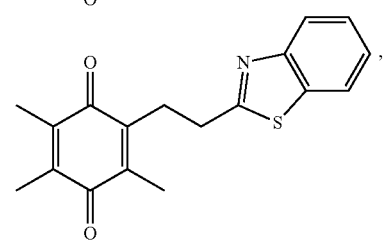,
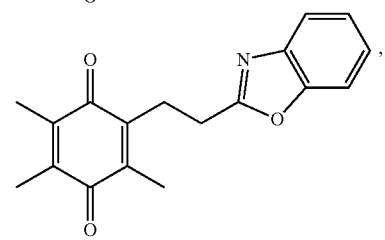,
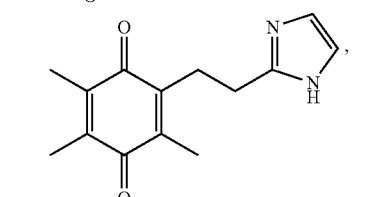,
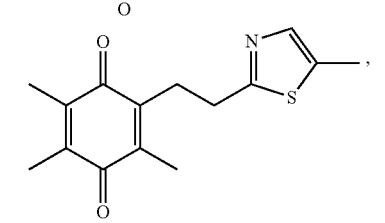,
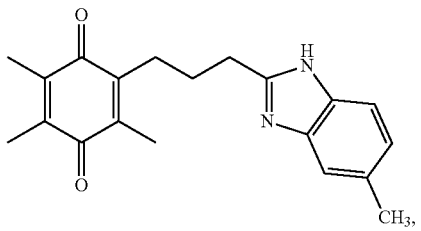,
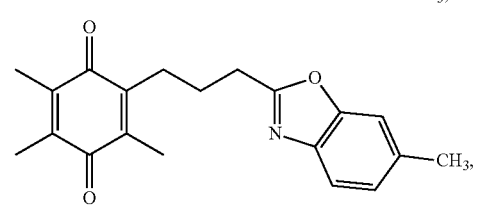,
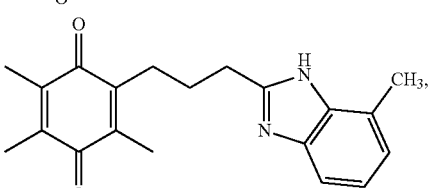,
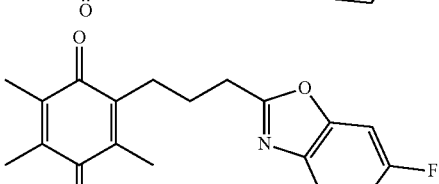,
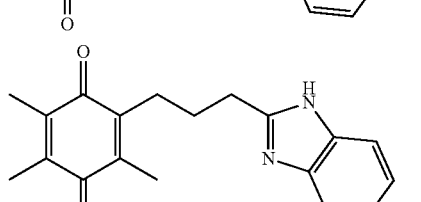,
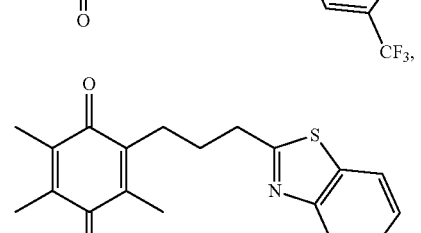,
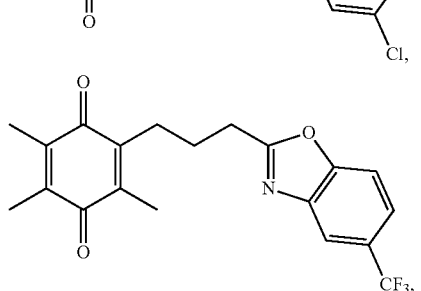,
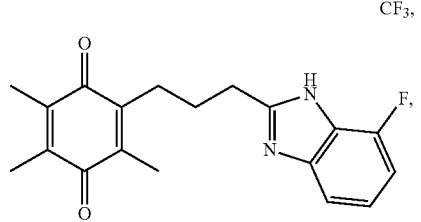,

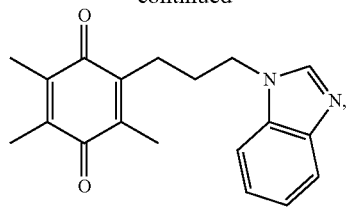
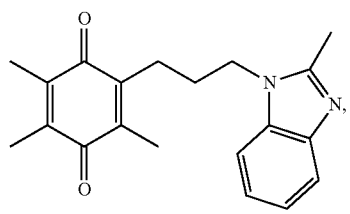
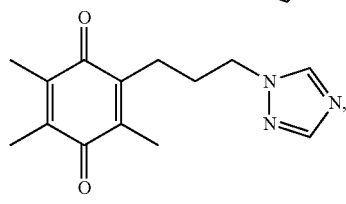
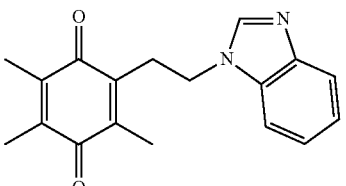
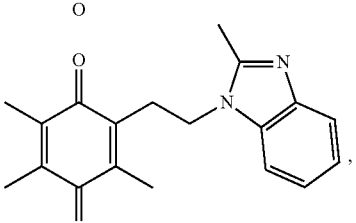
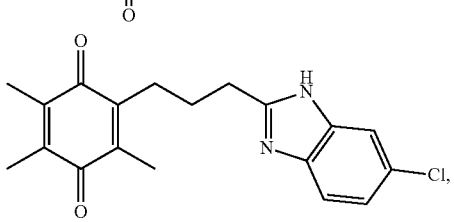
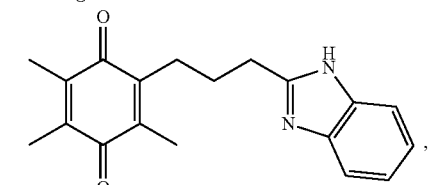
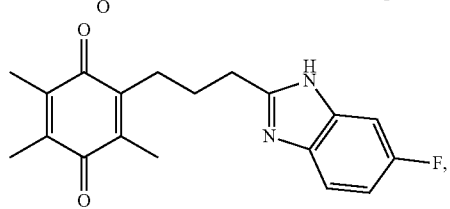
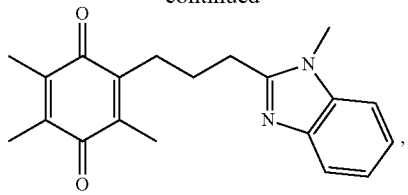
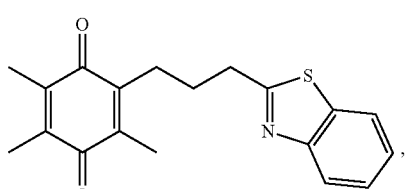
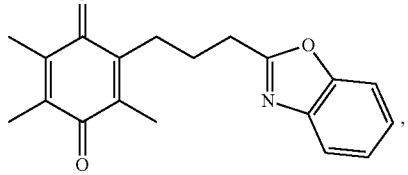
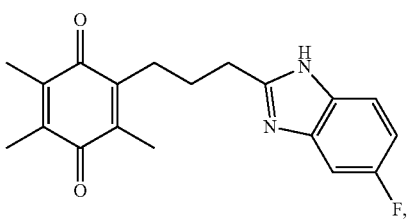
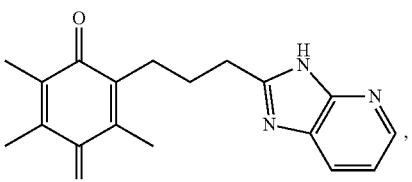
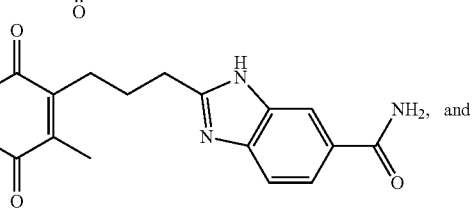
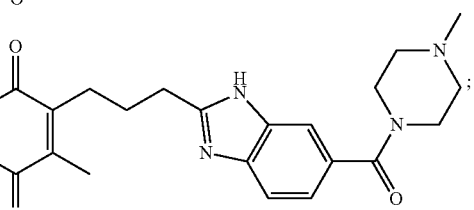
or a stereoisomer, mixture of stereoisomers, solvate, hydrate, pharmaceutically acceptable salt, or prodrug ester thereof. In some embodiments, including any of the foregoing embodiments, the compound is selected from the group consisting of:

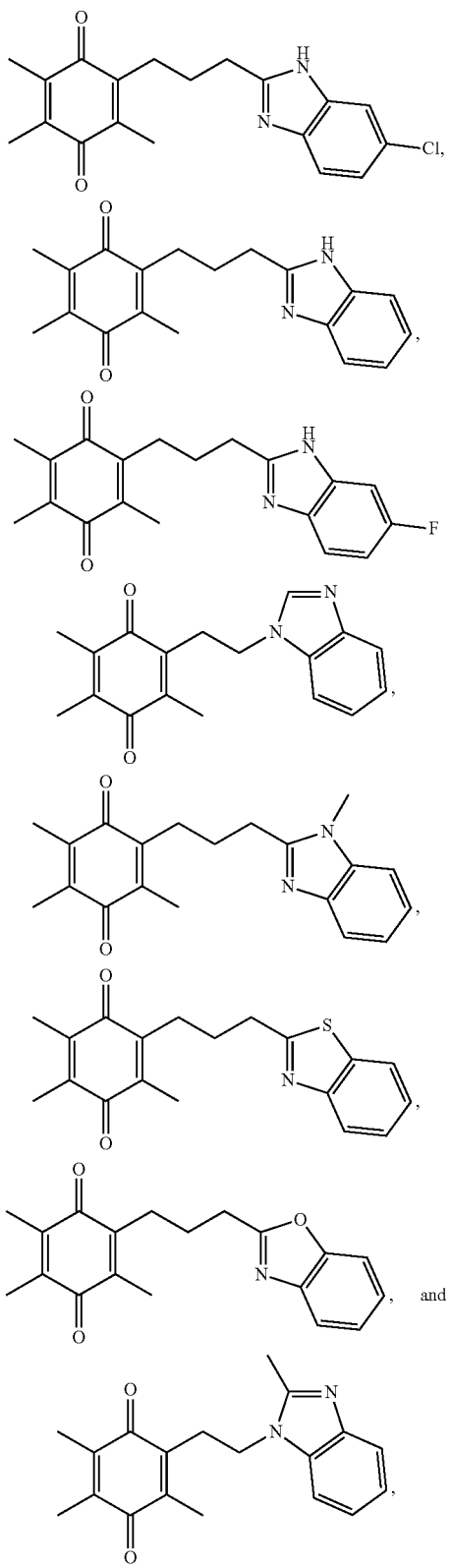

or a stereoisomer, mixture of stereoisomers, solvate, hydrate, pharmaceutically acceptable salt, or prodrug ester thereof. In some embodiments, including any of the foregoing embodiments, the compound is an ester prodrug:

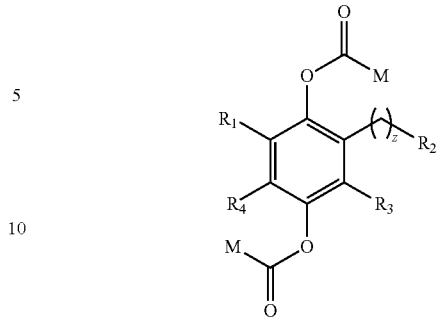

wherein M is $C_1$-$C_6$ alkyl, $C_6$-$C_{20}$ aryl, —O—$C_1$-$C_6$ alkyl, —$NH_2$, —N(H)($C_1$-$C_6$ alkyl), or —N($C_1$-$C_6$ alkyl)($C_1$-$C_6$ alkyl). In some embodiments, including any of the foregoing embodiments, the compound is a compound of Formula I or II, or a stereoisomer, mixture of stereoisomers, solvate, hydrate, or pharmaceutically acceptable salt thereof. In some embodiments, including any of the foregoing embodiments, the compound is a compound of Formula I or II, or a stereoisomer, mixture of stereoisomers, or pharmaceutically acceptable salt thereof. In some embodiments, including any of the foregoing embodiments, the compound is a compound of Formula I or II, or a stereoisomer or mixture of stereoisomers thereof. In some embodiments, including any of the foregoing embodiments, the compound is a compound of Formula I or II, or a pharmaceutically acceptable salt thereof. In some embodiments, including any of the foregoing embodiments, the compound has an $EC_{50}$ of less than about 1 μM, as measured by an assay described in any one of Examples 1-6. In some embodiments, including any of the foregoing embodiments, the compound has an $EC_{50}$ of less than about 500 nM, as measured by an assay described in any one of Examples 1-6. In some embodiments, including any of the foregoing embodiments, the compound has an $EC_{50}$ of less than about 250 nM, as measured by an assay described in any one of Examples 1-6. The method can use any individual compound of the invention as described herein, or a combination of compounds. In some embodiments, including any of the foregoing embodiments, the compound is administered as a pharmaceutical formulation comprising the compound and a pharmaceutically acceptable excipient. In some embodiments, including any of the foregoing embodiments, the pharmaceutical formulation comprises an active agent consisting essentially of the compound. In some embodiments, including any of the foregoing embodiments, the method is a method of treating or suppressing an oxidative stress disorder. In some embodiments, including any of the foregoing embodiments, the method is a method of treating an oxidative stress disorder. In some embodiments, including any of the foregoing embodiments, the method is a method of suppressing an oxidative stress disorder. In some embodiments, including any of the foregoing embodiments, the oxidative stress disorder is selected from the group consisting of: a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrongenase Deficiency (LCAD); LCHAD; Leigh Disease; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrongenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrongenase Deficiency (VLCAD); a myopathy; cardiomyopathy; encephalomyopathy; a neurodegenerative disease; Parkinson's disease; Alzheimer's disease; amyotrophic lateral sclerosis (ALS); a motor neuron disease; a neurological disease; epilepsy; an age-associated disease; macular degeneration; diabetes; metabolic syndrome; cancer; brain cancer; a genetic disease; Huntington's Disease; a mood disorder; schizophrenia; bipolar disorder; a pervasive developmental disorder; autistic disorder; Asperger's syndrome; childhood disintegrative disorder (CDD); Rett's disorder; PDD-not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobionopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multisystem atrophy; Adrenoleukodystrophy; and Adrenomyeloneuropathy. In some embodiments, including any of the foregoing embodiments, the oxidative stress disorder is a mitochondrial disorder. In some embodiments, including any of the foregoing embodiments, the oxidative stress disorder is an inherited mitochondrial disease. In some embodiments, including any of the foregoing embodiments, the oxidative stress disorder is Friedreich's Ataxia (FA). In some embodiments, including any of the foregoing embodiments, the oxidative stress disorder is Kearns-Sayre Syndrome (KSS). In some embodiments, including any of the foregoing embodiments, the oxidative stress disorder is Leigh Disease or Leigh-like Syndrome. In some embodiments, including any of the foregoing embodiments, the oxidative stress disorder is Leber's Hereditary Optic Neuropathy (LHON). In some embodiments, including any of the foregoing embodiments, the oxidative stress disorder is Mitochondrial Myopathy, Encephalopathy, Lactacidosis, Stroke (MELAS). In some embodiments, including any of the foregoing embodiments, the oxidative stress disorder is Myoclonic Epilepsy with Ragged Red Fibers (MERRF). In some embodiments, including any of the foregoing embodiments, the oxidative stress disorder is Parkinson's disease. In some embodiments, including any of the foregoing embodiments, the oxidative stress disorder is Alzheimer's disease. In some embodiments, including any of the foregoing embodiments, the oxidative stress disorder is amyotrophic lateral sclerosis (ALS). In some embodiments, including any of the foregoing embodiments, the oxidative stress disorder is epilepsy. In some embodiments, including any of the foregoing embodiments, the oxidative stress disorder is macular degeneration. In some embodiments, including any of the foregoing embodiments, the oxidative stress disorder is brain cancer. In some embodiments, including any of the foregoing embodiments, the oxidative stress disorder is Huntington's Disease. In some embodiments, including any of the foregoing embodiments, the oxidative stress disorder is autistic disorder. In some embodiments, including any of the foregoing embodiments, the oxidative stress disorder is Rett's disorder. In some embodiments, including any of the foregoing embodiments, the oxidative stress disorder is stroke. In some embodiments, including any of the foregoing embodiments, the oxidative stress disorder is Maternally inherited diabetes and deafness (MIDD). In some embodiments, including any of the foregoing embodiments, the oxidative stress disorder is chronic fatigue. In some embodiments, including any of the foregoing embodiments, the oxidative stress disorder is contrast-induced kidney damage. In some embodiments, including any of the foregoing embodiments, the oxidative stress disorder is contrast-induced retinopathy damage. In some embodiments, including any of the foregoing embodiments, the oxidative stress disorder is cobalamin c defect. In some embodiments, including any of the foregoing embodiments, the method is a method for modulating one or more energy biomarkers, normalizing one or more energy biomarkers, or enhancing one or more energy biomarkers, wherein the one or more energy biomarkers are selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H$^+$) levels; NADPH (NADPH+H$^+$) levels; NAD levels; NADP levels; ATP levels; reduced coenzyme Q ($CoQ^{red}$) levels; oxidized coenzyme Q ($CoQ^{ox}$) levels; total coenzyme Q ($CoQ^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In some embodiments, including any of the foregoing embodiments, the levels are modulated to a value within about 2 standard deviations of the value in a healthy subject. In some embodiments, including any of the foregoing embodiments, the levels are modulated to a value within about 1 standard deviation of the value in a healthy subject. In some embodiments, including any of the foregoing embodiments, the levels in a subject are changed by at least about 10% above or below the level in the subject prior to modulation. In some embodiments, including any of the foregoing embodiments, the levels are changed by at least about 20% above or below the level in the subject prior to modulation. In some embodiments, including any of the foregoing embodiments, the levels are changed by at least about 30% above or below the level in the subject prior to modulation. In some embodiments, including any of the foregoing embodiments, the levels are changed by at least about 40% above or below the level in the subject prior to modulation. In some embodiments, including any of the foregoing embodiments, the levels are changed by at least about 50% above or below the level in the subject prior to modulation. In some embodiments, including any of the foregoing embodiments, the levels are changed by at least about 75% above or below the level in the subject prior to modulation. In some embodiments, including any of the foregoing embodiments, the levels are changed by at least about 100% above or at least about 90% below the level in the subject prior to modulation. In some embodiments, including any of the foregoing embodiments, the subject or subjects in which a method of treating or suppressing an oxidative stress disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; subjects requiring organ visualization via contrast solution; or other subjects with acute, chronic, or ongoing energy demands who can benefit from enhancement of energy biomarkers.

In another aspect of the invention is the use of a compound as described herein, including any of the foregoing embodiments, for treating or suppressing an oxidative stress disorder. In another aspect of the invention is the use of a compound as described herein, including any of the foregoing embodiments, in the manufacture of a medicament for use in treating or suppressing an oxidative stress disorder.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

DETAILED DESCRIPTION

The invention embraces compounds useful in treating or suppressing diseases, developmental delays and symptoms related to oxidative stress such as mitochondrial disorders, impaired energy processing disorders, neurodegenerative diseases and diseases of aging, and methods of using such compounds for treating or suppressing an oxidative stress disorder, or for modulating, normalizing, or enhancing one or more (e.g. one, two, three, or more) energy biomarkers.

The abbreviations used herein have their conventional meaning within the chemical and biological arts, unless otherwise specified.

Reference to "about" a value or parameter herein includes (and describes) variations that are directed to that value or parameter per se. For example, description referring to "about X" includes description of "X".

The terms "a" or "an," as used in herein means one or more, unless context clearly dictates otherwise.

By "subject," "individual," or "patient" is meant an individual organism, preferably a vertebrate, more preferably a mammal, most preferably a human.

"Treating" a disorder with the compounds and methods discussed herein is defined as administering one or more of the compounds discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder. "Suppression" of a disorder with the compounds and methods discussed herein is defined as administering one or more of the compounds discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. Because some of the disorders are inherited, genetic screening can be used to identify patients at risk of the disorder. The compounds and methods of the invention can then be administered to asymptomatic patients at risk of developing the clinical symptoms of the disorder, in order to suppress the appearance of any adverse symptoms.

"Therapeutic use" of the compounds discussed herein is defined as using one or more of the compounds discussed herein to treat or suppress a disorder, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disorder or one or more symptoms of a disorder, or to retard the progression of a disorder or of one or more symptoms of a disorder, or to reduce the severity of a disorder or of one or more symptoms of a disorder, or to suppress the clinical manifestation of a disorder, or to suppress the manifestation of adverse symptoms of a disorder. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as e.g. a mitochondrial disorder, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes, if chemically possible, all stereoisomers of the compounds, including diastereomers and enantiomers. The invention also includes mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Prodrug ester forms include, for example, the following:

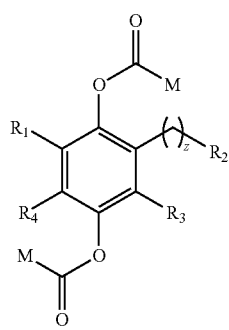

wherein M is $C_1$-$C_6$ alkyl, $C_6$-$C_{20}$ aryl, —O—$C_1$-$C_6$ alkyl, —$NH_2$, —N(H)($C_1$-$C_6$ alkyl), —N($C_1$-$C_6$ alkyl)($C_1$-$C_6$ alkyl). Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The description of compounds herein also includes all isotopologues, for example, partially deuterated or perdeuterated analogs of all compounds herein.

Metabolites of the compounds are also embraced by the invention.

"($C_1$-$C_6$) alkyl" is intended to embrace a saturated linear, branched, or cyclic hydrocarbon, or any combination thereof, of 1 to 6 carbon atoms. Non-limiting examples of "($C_1$-$C_6$) alkyl" include methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl, cyclopentyl, hexyl, and cyclohexyl. The point of attachment of the ($C_1$-$C_6$) alkyl group to the remainder of the molecule can be at any chemically possible location on the ($C_1$-$C_6$) alkyl group.

"Halogen" or "halo" designates fluoro, chloro, bromo, and iodo.

The terms "heteroaryl", is intended to encompass a monovalent aromatic, carbocyclic radical of 5-10 ring atoms having one ring or two condensed (fused) rings incorporating one, two, three or four heteroatoms within the ring(s) (chosen from nitrogen, oxygen, and/or sulfur). The attachment point of the heteroaryl group to the rest of the molecule may be either through a C or N in the ring(s). Non-limiting examples of heteroaryl include pyridine, pyrazine, imidazole, thiazole, isothiazole, pyrazine, triazine, triazole, pyrimidine, pyridazine, pyrazole, thiophene, pyrrole, furan, oxazole, indole, quinoline, quinazoline, benzoimidazole, benzothiophene, benzofuran, benzoxazole, benzothiazole, benzotriazole, isoindole, isoquinoline, indazole, cinnoline, quinazoline, quinoxaline, phthalazine, benzotriazole, benzisoxazole, benzothiazole, benzoisothiazole, and the like.

By "respiratory chain disorder" is meant a disorder which results in the decreased utilization of oxygen by a mitochondrion, cell, tissue, or individual, due to a defect or disorder in a protein or other component contained in the mitochondrial respiratory chain. By "protein or other component contained in the mitochondrial respiratory chain" is meant the components (including, but not limited to, proteins, tetrapyrroles, and cytochromes) comprising mitochondrial complex I, II, III, IV, and/or V. "Respiratory chain protein" refers to the protein components of those complexes, and "respiratory chain protein disorder" is meant a disorder which results in the decreased utilization of oxygen by a mitochondrion, cell, tissue, or individual, due to a defect or disorder in a protein contained in the mitochondrial respiratory chain.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "Friedreich's ataxia" is intended to embrace other related ataxias, and is also sometimes referred to as hereditary ataxia, familial ataxia, or Friedreich's tabes.

The term "ataxia" is an aspecific clinical manifestation implying dysfunction of parts of the nervous system that coordinate movement, such as the cerebellum. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias. Ataxias are also often associated with hearing impairments.

There are three types of ataxia, cerebellar ataxia, including vestibulo-cerebellar dysfunction, spino-cerebellar dysfunction, and cerebro-cerebellar dysfunction; sensory ataxia; and vestibular ataxia. Examples of the diseases which are classifiable into spino-cerebellar ataxia or multiple system atrophy are hereditary olivo-ponto-cerebellar atrophy, hereditary cerebellar cortical atrophy, Friedreich's ataxia, Machado-Joseph diseases, Ramsay Hunt syndrome, hereditary dentatorubral-pallidoluysian atrophy, hereditary spastic paraplegia, Shy-Drager syndrome, cortical cerebellar atrophy, striato-nigral degeneration, Marinesco-Sjogren syndrome, alcoholic cortical cerebellar atrophy, paraneoplastic cerebellar atrophy associated with malignant tumor, toxic cerebellar atrophy caused by toxic substances, Vitamine E deficiency due to mutation of a Tocopherol transfer protein (aTTP) or lipid absorption disorder such as Abetalipoproteinemia, cerebellar atrophy associated with endocrine disturbance and the like.

Examples of ataxia symptoms are motor ataxia, trunk ataxia, limb ataxia and the like, autonomic disturbance such as orthostatic hypotension, dysuria, hypohidrosis, sleep apnea, orthostatic syncope and the like, stiffness of lower extremity, ocular nystagmus, oculomotor nerve disorder, pyramidal tract dysfunction, extrapyramidal symptoms (postural adjustment dysfunction, muscular rigidity, akinesia, tremors), dysphagia, lingual atrophy, posterior funiculus symptom, muscle atrophy, muscle weakness, deep hyperreflexia, sensory disturbance, scoliosis, kyphoscoliosis, foot deformities, anarthria, dementia, manic state, decreased motivation for rehabilitation and the like.

Diseases Amenable to Treatment or Suppression with Compounds and Methods of the Invention A variety of disorders/diseases are believed to be caused or aggravated by oxidative stress affecting normal electron flow in the cells, such as mitochondrial disorders, impaired energy processing disorders, neurodegenerative diseases and diseases of aging, and can be treated or suppressed using the compounds and methods of the invention.

Non-limiting examples of oxidative stress disorders include, for example, mitochondrial disorders (including inherited mitochondrial diseases) such as Alpers Disease, Barth syndrome, Beta-oxidation Defects, Carnitine-Acyl-Carnitine Deficiency, Carnitine Deficiency, Creatine Deficiency Syndromes, Co-Enzyme Q10 Deficiency, Complex I Deficiency, Complex II Deficiency, Complex III Deficiency, Complex IV Deficiency, Complex V Deficiency, COX Deficiency, chronic progressive external ophthalmoplegia (CPEO), CPT I Deficiency, CPT II Deficiency, Friedreich's Ataxia (FA), Glutaric Aciduria Type II, Kearns-Sayre Syndrome (KSS), Lactic Acidosis, Long-Chain Acyl-CoA Dehydrongenase Deficiency (LCAD), LCHAD, Leigh Disease or Syndrome, Leigh-like Syndrome, Leber's Hereditary Optic Neuropathy (LHON, also referred to as Leber's Disease, Leber's Optic Atrophy (LOA), or Leber's Optic Neuropathy (LON)), Lethal Infantile Cardiomyopathy (LIC), Luft Disease, Multiple Acyl-CoA Dehydrogenase Deficiency (MAD), Medium-Chain Acyl-CoA Dehydrongenase Deficiency (MCAD), Mitochondrial Myopathy, Encephalopathy, Lactacidosis, Stroke (MELAS), Myoclonic Epilepsy with Ragged Red Fibers (MERRF), Mitochondrial Recessive Ataxia Syndrome (MIRAS), Mitochondrial Cytopathy, Mitochondrial DNA Depletion, Mitochondrial Encephalopathy, Mitochondrial Myopathy, Myoneurogastointestinal Disorder and Encephalopathy (MNGIE), Neuropathy, Ataxia, and Retinitis Pigmentosa (NARP), Pearson Syndrome, Pyruvate Carboxylase Deficiency, Pyruvate Dehydrogenase Deficiency, POLG Mutations, Respiratory Chain Disorder, Short-Chain Acyl-CoA Dehydrogenase Deficiency (SCAD), SCHAD, Very Long-Chain Acyl-CoA Dehydrongenase Deficiency (VLCAD); myopathies such as cardiomyopathy and encephalomyopathy; neurodegenerative diseases such as Parkinson's disease, Alzheimer's disease, and amyotrophic lateral sclerosis (ALS, also known as Lou Gehrig's disease); motor neuron diseases; neurological diseases such as epilepsy; age-associated diseases, particularly diseases for which CoQ10 has been proposed for treatment, such as macular degeneration, diabetes, metabolic syndrome, and cancer (e.g. brain cancer); genetic diseases such as Huntington's Disease (which is also a neurological disease); mood disorders such as schizophrenia and bipolar disorder; pervasive developmental disorders such as autistic disorder, Asperger's syndrome, childhood disintegrative disorder (CDD), Rett's disorder, and PDD-not otherwise specified (PDD-NOS); cerebrovascular accidents such as stroke; vision impairments such as those caused by neurodegenerative diseases of the eye such as optic neuropathy, Leber's hereditary optic neuropathy, dominant inherited juvenile optic atrophy, optic neuropathy caused by toxic agents, glaucoma, age-related macular degeneration (both "dry" or non-exudative macular degeneration and "wet" or exudative macular degeneration), Stargardt's macular dystrophy, diabetic retinopathy, diabetic maculopathy, retinopathy of prematurity, or ischemic reperfusion-related retinal injury; disorders caused by energy impairment include diseases due to deprivation, poisoning or toxicity of oxygen, and qualitative or quantitative disruption in the transport of oxygen such as haemoglobionopathies, for example thalassemia or sickle cell anemia; other diseases in which mitochondrial dysfunction is implicated such as excitoxic, neuronal injury, such as that associated with seizures, stroke and ischemia; and other disorders including renal tubular acidosis; attention deficit/hyperactivity disorder (ADHD); neurodegenerative disorders resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; muscular dystrophies; leukodystrophies; Progressive Supranuclear Palsy; spinal muscular atrophy; hearing loss (e.g. noise induced hearing loss); traumatic brain injury; Juvenile Huntington's Disease; Multiple Sclerosis; NGLY1; Multisystem atrophy; Adrenoleukodystrophy; and Adrenomyeloneuropathy. It is to be understood that certain specific diseases or disorders may fall within more than one category; for example, Huntington's Disease is a genetic disease as well as a neurological disease. Furthermore, certain oxidative stress diseases and disorders may also be considered mitochondrial disorders.

For some disorders amenable to treatment with compounds and methods of the invention, the primary cause of the disorder is due to a defect in the respiratory chain or another defect preventing normal utilization of energy in mitochondria, cells, or tissue(s). Non-limiting examples of disorders falling in this category include inherited mitochondrial diseases, such as Myoclonic Epilepsy with Ragged Red Fibers (MERRF), Mitochondrial Myopathy, Encephalopathy, Lactacidosis, and Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), and Friedreich's Ataxia (FA). For some disorders amenable to treatment with compounds and methods of the invention, the primary cause of the disorder is not due to respiratory chain defects or other defects preventing normal utilization of energy in mitochondria, cells, or tissue(s); non-limiting examples of disorders falling in this category include stroke, cancer, and diabetes. However, these latter disorders are particularly aggravated by energy impairments, and are particularly amenable to treatment with compounds of the invention in order to ameliorate the condition. Pertinent examples of such disorders include ischemic stroke and hemorrhagic stroke, where the primary cause of the disorder is due to impaired blood supply to the brain. While an ischemic episode caused by a thrombosis or embolism, or a hemorrhagic episode caused by a ruptured blood vessel, is not primarily caused by a defect in the respiratory chain or another metabolic defect preventing normal utilization of energy, oxidative stress plays a role in the ischemic cascade due to oxygen reperfusion injury following hypoxia (this cascade occurs in heart attacks as well as in strokes). Accordingly, treatment with compounds and methods of the invention will mitigate the effects of the disease, disorder or condition. Modulating one or more energy biomarkers, normalizing one or more energy biomarkers, or enhancing one or more energy biomarkers can also prove beneficial in such disorders both as a therapeutic measure and a prophylactic measure. For example, for a patient scheduled to undergo non-emergency repair of an aneurysm, enhancing energy biomarkers before and during the pre-operative can improve the patient's prognosis should the aneurysm rupture before successful repair.

The term "oxidative stress disorder" or "oxidative stress disease" encompass both diseases caused by oxidative stress and diseases aggravated by oxidative stress. The terms "oxidative stress disorder" or "oxidative stress disease" encompass both diseases and disorders where the primary cause of the disease is due to a defect in the respiratory chain or another defect preventing normal utilization of energy in mitochondria, cells, or tissue(s), and also diseases and disorders where the primary cause of the disease is not due to a defect in the respiratory chain or another defect preventing normal utilization of energy in mitochondria, cells, or tissue(s). The former set of diseases can be referred to as "primary oxidative stress disorders," while the latter can be referred to as "secondary oxidative stress disorders." It should be noted that the distinction between "diseases caused by oxidative stress" and "diseases aggravated by oxidative stress" is not absolute; a disease may be both a disease caused by oxidative stress and a disease aggravated by oxidative stress. The boundary between "primary oxidative stress disorder" and a "secondary oxidative stress disorder" is more distinct, provided that there is only one primary cause of a disease or disorder and that primary cause is known.

Bearing in mind the somewhat fluid boundary between diseases caused by oxidative stress and diseases aggravated by oxidative stress, mitochondrial diseases or disorders and impaired energy processing diseases and disorders tend to fall into the category of diseases caused by oxidative stress, while neurodegenerative disorders and diseases of aging tend to fall into the category of diseases aggravated by oxidative stress. Mitochondrial diseases or disorders and impaired energy processing diseases and disorders are generally primary oxidative stress disorders, while neurodegenerative disorders and diseases of aging may be primary or secondary oxidative stress disorders.

Clinical Assessment of Oxidative Stress and Efficacy of Therapy

Several readily measurable clinical markers are used to assess the metabolic state of patients with oxidative stress disorders. These markers can also be used as indicators of the efficacy of a given therapy, as the level of a marker is moved from the pathological value to the healthy value. These clinical markers include, but are not limited to, energy biomarkers such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; total, reduced or oxidized glutathione levels, or reduced/oxidized glutathione ratio either in whole blood, plasma, lymphocytes, cerebrospinal fluid, or cerebral ventricular fluid; total, reduced or oxidized cysteine levels, or reduced/oxidized cysteine ratio either in whole blood, plasma, lymphocytes, cerebrospinal fluid, or cerebral ventricular fluid; phosphocreatine levels, NADH (NADH+H+) or NADPH (NADPH+H+) levels; NAD or NADP levels; ATP levels; anaerobic threshold; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from an oxidative stress disorder, such as Friedreich's ataxia, Leber's hereditary optic neuropathy, MELAS, KSS or CoQ10 deficiency, is improved to within two standard deviations of the average level in a healthy subject. In another embodiment of the invention, the level of one or more of these energy biomarkers in a patient suffering from a oxidative stress disorder, such as Friedreich's ataxia, Leber's hereditary optic neuropathy, MELAS, KSS or CoQ10 deficiency is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Lactate, a product of the anaerobic metabolism of glucose, is removed by reduction to pyruvate in an aerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+H+, NADPH+H+, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH (NADH+H+) or NADPH (NADPH+H+) can be measured by a variety of fluorescent, enzymatic, or electrochemical techniques, e.g., the electrochemical assay described in US 2005/0067303.

GSH, GSSG, Cys, and CySS levels: Briefly, plasma levels of GSH, GSSG, Cys, and CySS are used to calculate the in vivo $E_h$ values. Samples are collected using the procedure of Jones et al (2009 Free Radical Biology & Medicine 47(10) pp 1329-1338), and bromobimane is used to alkylate free thiols and HPLC and either electrochemical or MSMS to separate, detect, and quantify the molecules. As described in more detail in U.S. Provisional Patent Application No. 61/698,431 filed Sep. 7, 2012, and U.S. Provisional Patent Application 61/792,797 filed Mar. 15, 2013, we have developed a method for different experimental parameters to analyze the most common monothiols and disulfide (cystine, cysteine, reduced (GSH) and oxidized glutathione (GSSG)) present in human plasma, and using Bathophenanthroline disulfonic acid as the internal standard (IS). Complete separation of all the targets analytes and IS at 35.0 on a C18 RP column (250 mm×4.6 mm, 3 micron) was achieved using 0.2% TFA:Acetonitrile as a mobile phase pumped at the rate of 0.6 ml min-1 using electrochemical detector in DC mode at the detector potential of 1475 mV.

Oxygen consumption (vO2 or VO2), carbon dioxide output (vCO2 or VCO2), and respiratory quotient (VCO2/VO2): vO2 is usually measured either while resting (resting vO2) or at maximal exercise intensity (vO2 max). Optimally, both values will be measured. However, for severely disabled patients, measurement of vO2 max may be impractical. Measurement of both forms of vO2 is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt Cox), reduced cytochrome C levels (Cyt Cred), and the ratio of oxidized cytochrome C/reduced cytochrome C ratio (Cyt Cox)/(Cyt Cred), can be measured by in vivo near infrared spectroscopy. See, e.g., Rolfe, P., "In vivo near-infrared spectroscopy," Annu. Rev. Biomed. Eng. 2:715-54 (2000) and Strangman et al., "Non-invasive neuroimaging using near-infrared light" Biol. Psychiatry 52:679-93 (2002).

Exercise tolerance/Exercise intolerance: Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q (CoQred) levels, oxidized coenzyme Q (CoQox) levels, total coenzyme Q (CoQtot) levels, oxidized cytochrome C levels, reduced cytochrome C levels, oxidized cytochrome C/reduced cytochrome C ratio, GSH and cysteine reduced, oxidized, total levels and ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable Energy Biomarker | Physical Effect |
|---|---|---|---|
| Respiratory Chain | ↑ NADH | Δ lactate, Δ lactate:pyruvate ratio; and Δ acetoacetate:β-hydroxy butyrate ratio | Metabolic dyscrasia & fatigue |
| Respiratory Chain | ↓ H+ gradient | Δ ATP | Organ dependent dysfunction |
| Respiratory Chain | ↓ Electron flux | Δ VO2, RQ, BMR, ΔT, AT, pH | Metabolic dyscrasia & fatigue |
| Mitochondria & cytosol | ↓ ATP, ↓ VO2 | Δ Work, Δ HR (CO) | Exercise intolerance |
| Mitochondria & cytosol | ↓ ATP | Δ PCr | Exercise intolerance |
| Respiratory Chain | ↓ Cyt COx/Red | Δ λ~700-900 nm (Near Infrared Spectroscopy) | Exercise intolerance |
| Intermediary metabolism | ↓ Catabolism | Δ C14-Labeled substrates | Metabolic dyscrasia & fatigue |
| Respiratory Chain | ↓ Electron flux | Δ Mixed Venous VO2 | Metabolic dyscrasia & fatigue |
| Mitochondria & cytosol | ↑ Oxidative stress | Δ Tocopherol & Tocotrienols, CoQ10, docosahexaenoic acid | Uncertain |
| Mitochondria & cytosol | ↑ Oxidative stress | Δ Glutathionered | Uncertain |
| Mitochondria & cytosol | Nucleic acid oxidation | Δ 8-hydroxy 2-deoxy guanosine | Uncertain |
| Mitochondria & cytosol | Lipid oxidation | Δ Isoprostane(s), eicosanoids | Uncertain |
| Cell membranes | Lipid oxidation | Δ Ethane (breath) | Uncertain |
| Cell membranes | Lipid oxidation | Δ Malondialdehyde | Uncertain |

Treatment of a subject afflicted by an oxidative stress disorder in accordance with the methods of the invention may result in the inducement of a reduction or alleviation of symptoms in the subject, e.g., to halt the further progression of the disorder.

Partial or complete suppression of the oxidative stress disorder can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of oxidative stress disorders, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a oxidative stress disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in in vitro, in vivo, or ex vivo experiments to modulate one or more energy biomarkers in an experimental system. Such experimental systems can be cell samples, tissue samples, cell components, cell components, partial organs, whole organs, or organisms. Any one or more of the compounds of formula I or II can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least two compounds, and 4) selecting a compound or compounds for use in treatment, suppression, or modulation based on the amount of modulation determined in step 3.

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-$\beta$-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

In some embodiments of the invention, especially those embodiments where a formulation is used for injection or other parenteral administration including the routes listed herein, but also including embodiments used for oral, gastric, gastrointestinal, or enteric administration, the formulations and preparations used in the methods of the invention are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The invention also provides articles of manufacture and kits containing materials useful for treating or suppressing oxidative stress disorders. The invention also provides kits comprising any one or more of the compounds of formula I or II. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are a therapeutically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, NAC, and antioxidant compounds.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

Preparation of Compounds of the Invention

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, xylene, tetrahydrofuran ("THF"), chloroform, methylene chloride (or dichloromethane, ("DCM")), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

The compounds herein are synthesized by an appropriate combination of generally well-known synthetic methods. Techniques useful in synthesizing the compounds herein are both readily apparent and accessible to those of skill in the relevant art in light of the teachings described herein. The discussion below is offered to illustrate certain of the diverse methods available for use in assembling the compounds herein. However, the discussion is not intended to define the scope of reactions or reaction sequences that are useful in preparing the compounds herein.

A non-limiting, illustrative example of synthesis of intermediate compounds is as follows:

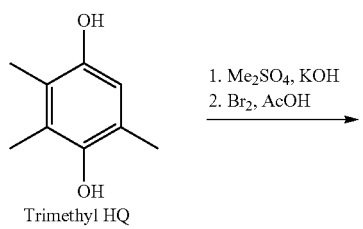

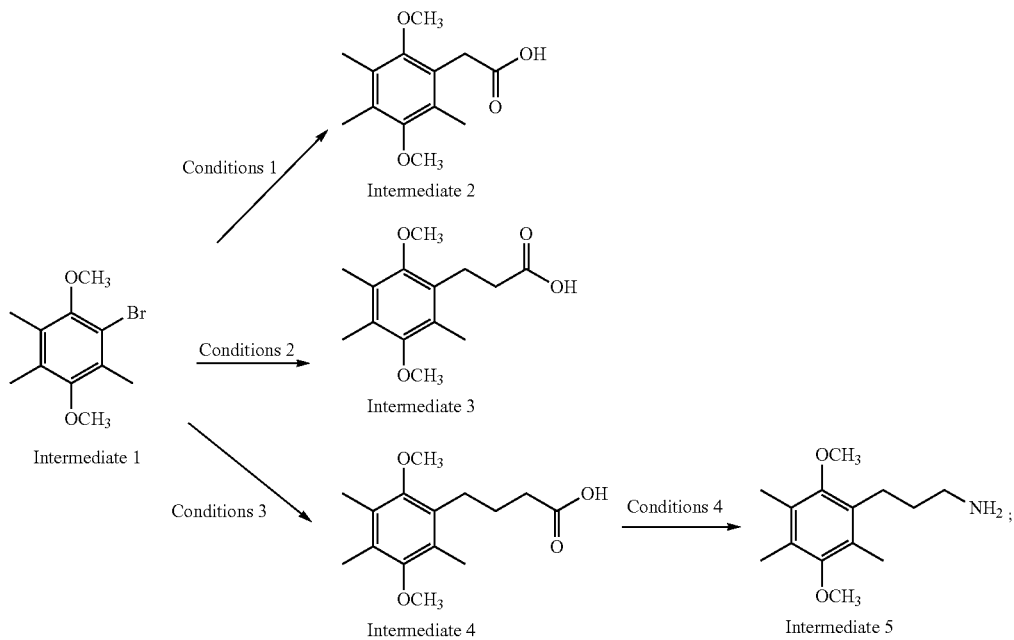
Conditions 1: nBuLi, diphenylparabanic acid; hydrazine, ethylene glycol, KOH, *JOC* (2012) 77, 632-39; Conditions 2: Heck reaction; KOH; Conditions 3: Mg, succinic anhydride; hydrazine, KOH, ethylene glycol. *Synthesis* (2005) 1789-9; Conditions 4: (PhO)$_2$P(O)N$_3$, BnOH; H$_2$, Pd(OH)$_2$, *JOC* (2007) 72, 775-81.
A non-limiting, illustrative example of synthesis of compounds of the invention from such intermediates is as follows:
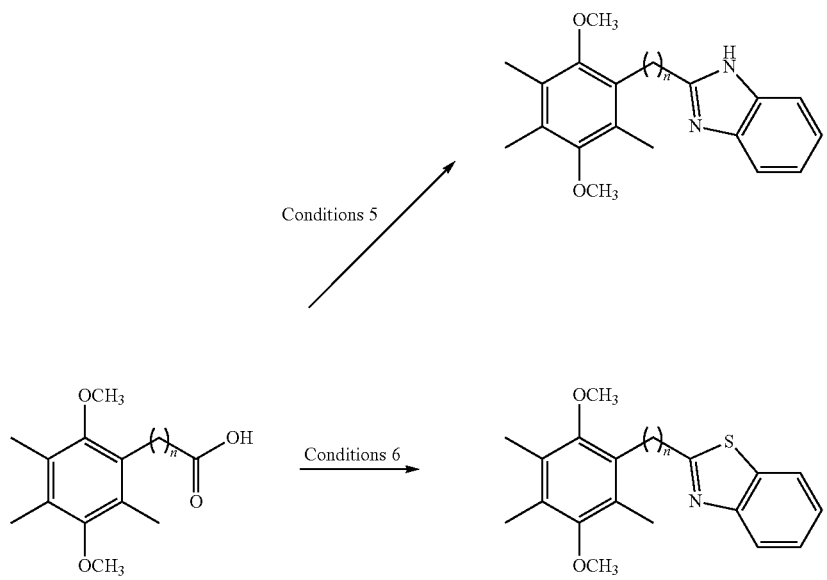

-continued
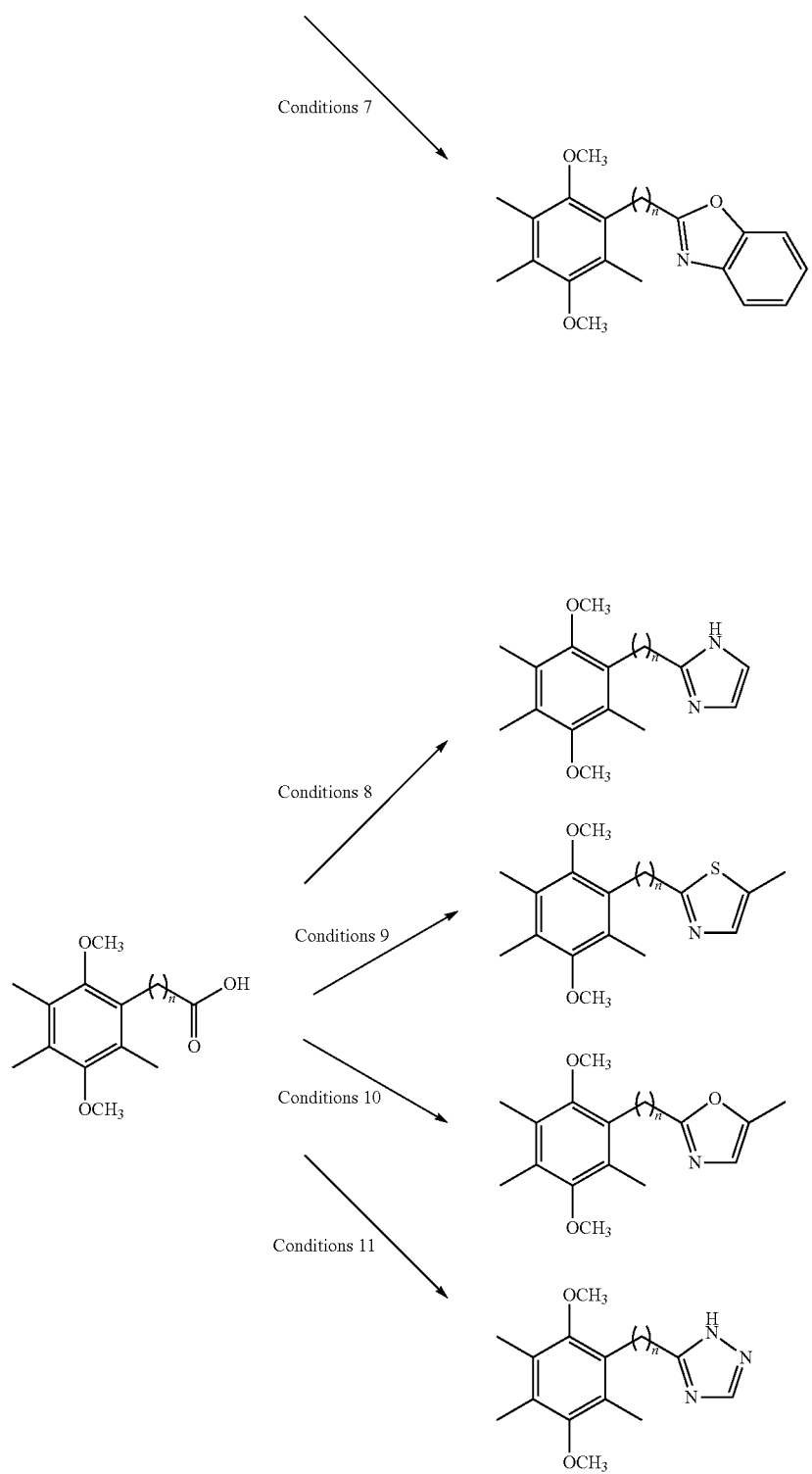

-continued

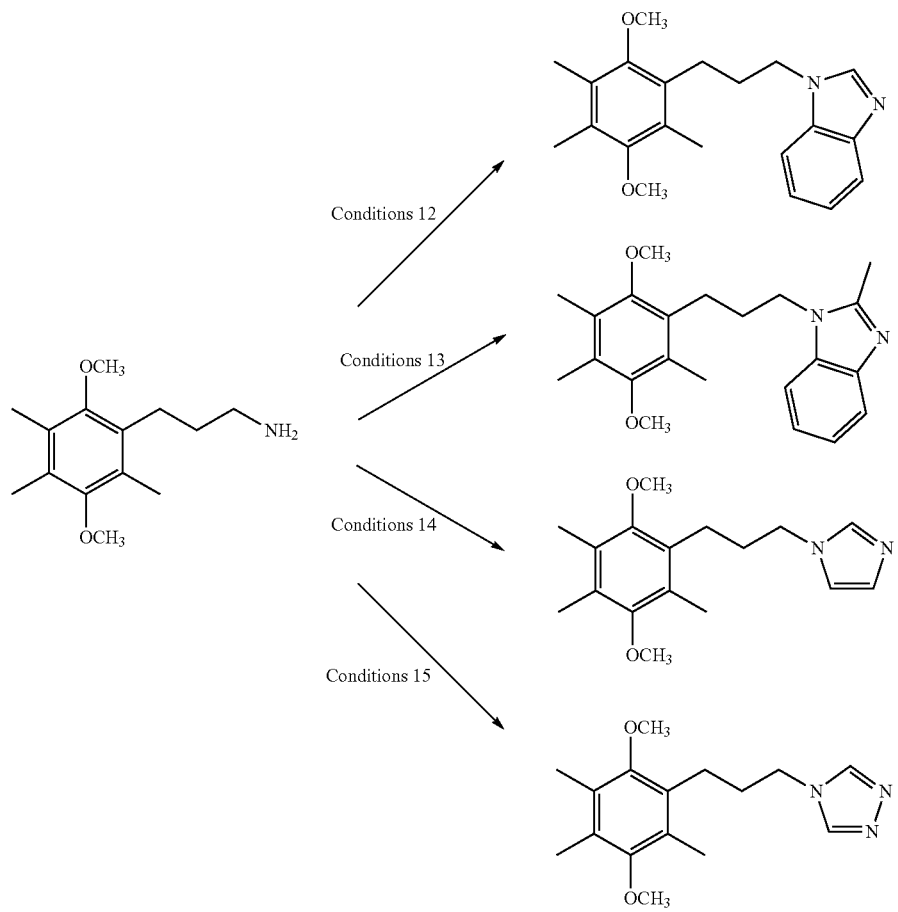

Conditions 5: SOCl2; dianiline, BF3—OEt2. *EJOC*(2009) 44, 1751-57; Conditions 6: SOCl2; thioniline, toluene, NaHCO3. *Synthesis* (2005) 2521-6; Conditions 7: boric acid, xylene. *Synthesis* (1982) 484-5; Conditions 8: SOCl2; C2H6N2, BF3—OEt2. *EJOC*(2009) 44, 1751-57; Conditions 9: amino-2-propanol, EDCI, HOBt, DMF; Dess-Martin oxidation; Lawesson's reagent, THF. *ACS Med Chem Lett* (2011) 53, 6355; Conditions 10: propargyl amine, EDCI, HOBt, DMF; AuCl3, MeCN. *Org Lett* (2008) 10, 4379-82; Conditions 11: EDCI, HOBt, NH4Cl; HC(OMe)2(NMe)2(NMe2); N2H4, AcOH. *EJOC* (2009) 9, 1445-52; Conditions 12: 1-fluoro-2-initrobenzene, K2CO3, DMSO; Pd/C, formic acid, EtOH; Conditions 13: 1-fluoro-2-nitrobenzene, K2CO3, DMSO; Pd/C, acetic acid, EtOH; Conditions 14: glyoxal, HCHO, NH4OAc, MeOH. *Tetrahedron* (2006) 62, 8199-8206; Conditions 15: SOCl2; hydrazine, DMF; refluxing benzene. *Synthesis* (2008) 149-54.

A non-limiting, illustrative example of conversion to the quinone form is as follows:

The reduced (hydroxy) form may readily be converted to the oxidized (quinone) form using methods known in the art. See e.g. air, silica Miller et al PCT Intl Appl 2006130775 7 Dec. 2006. The oxidized (quinone) form may readily be converted to the reduced hydroxy form using methods known in the art. See, e.g. Zn, AcOH Fuchs et al EJOC 6 (2009) 833-40.

A non-limiting, exemplary method for producing prodrug forms of the compounds of the invention is as follows:

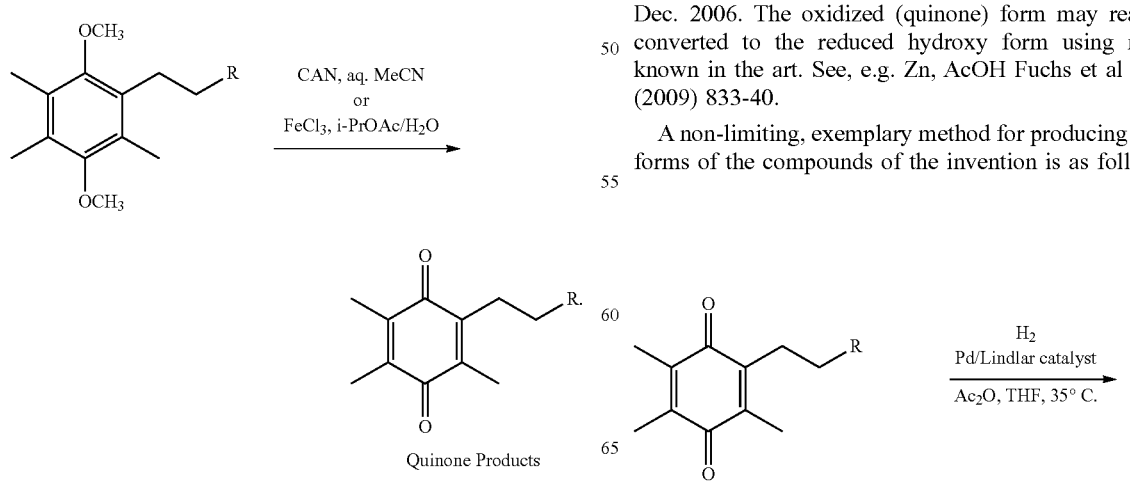

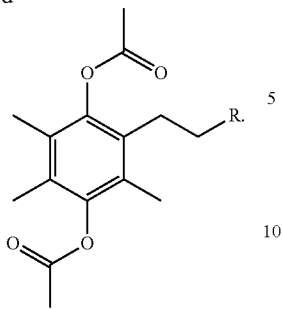

Other methods will be apparent to one skilled in the art.

Synthetic methods for other compounds of the invention will be apparent to one skilled in the art in view of the illustrative examples above.

EXAMPLES

Example A. Synthesis of Compounds 50 mg of the following compounds are synthesized at >95% peak purity by HPLC with 1H NMR analysis in accordance with the above described synthetic schemes. Compounds are purified by prep-HPLC (formic acid counterions only), and are delivered as lyophilized powders.

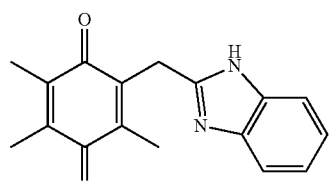

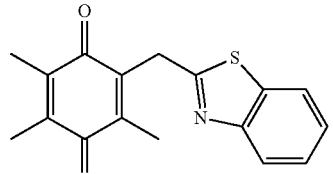

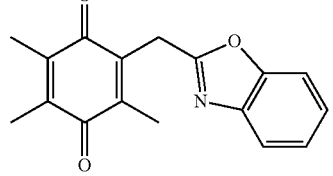

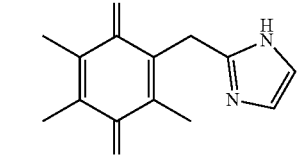

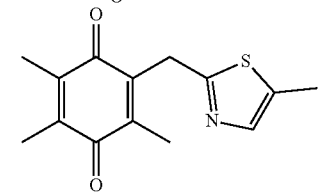

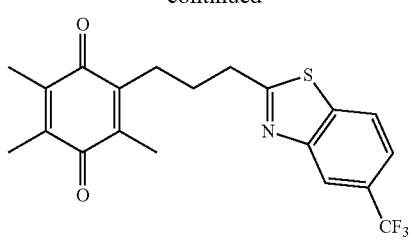

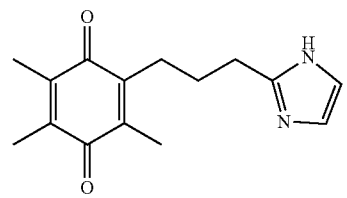

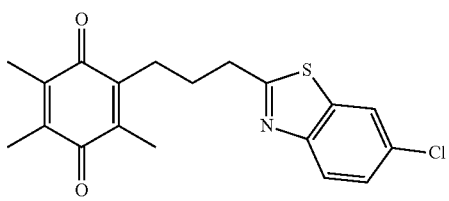

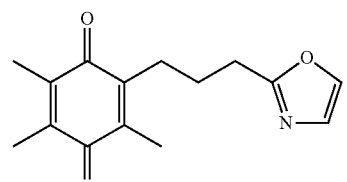

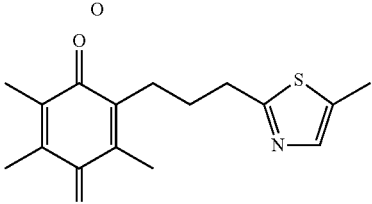

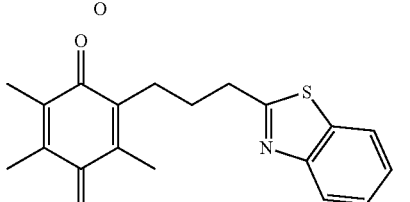

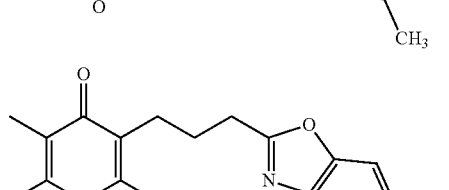

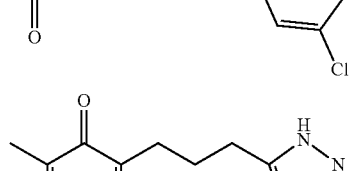

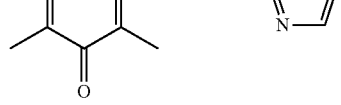

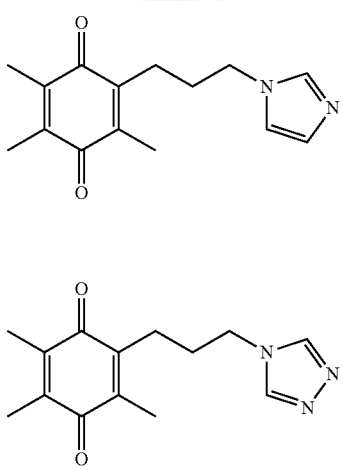

Example B. Synthesis of N-Linked Heteroaryl Compounds of the Invention

An exemplary synthesis of an N-linked heteroaryl compound of the invention is shown in the scheme below.

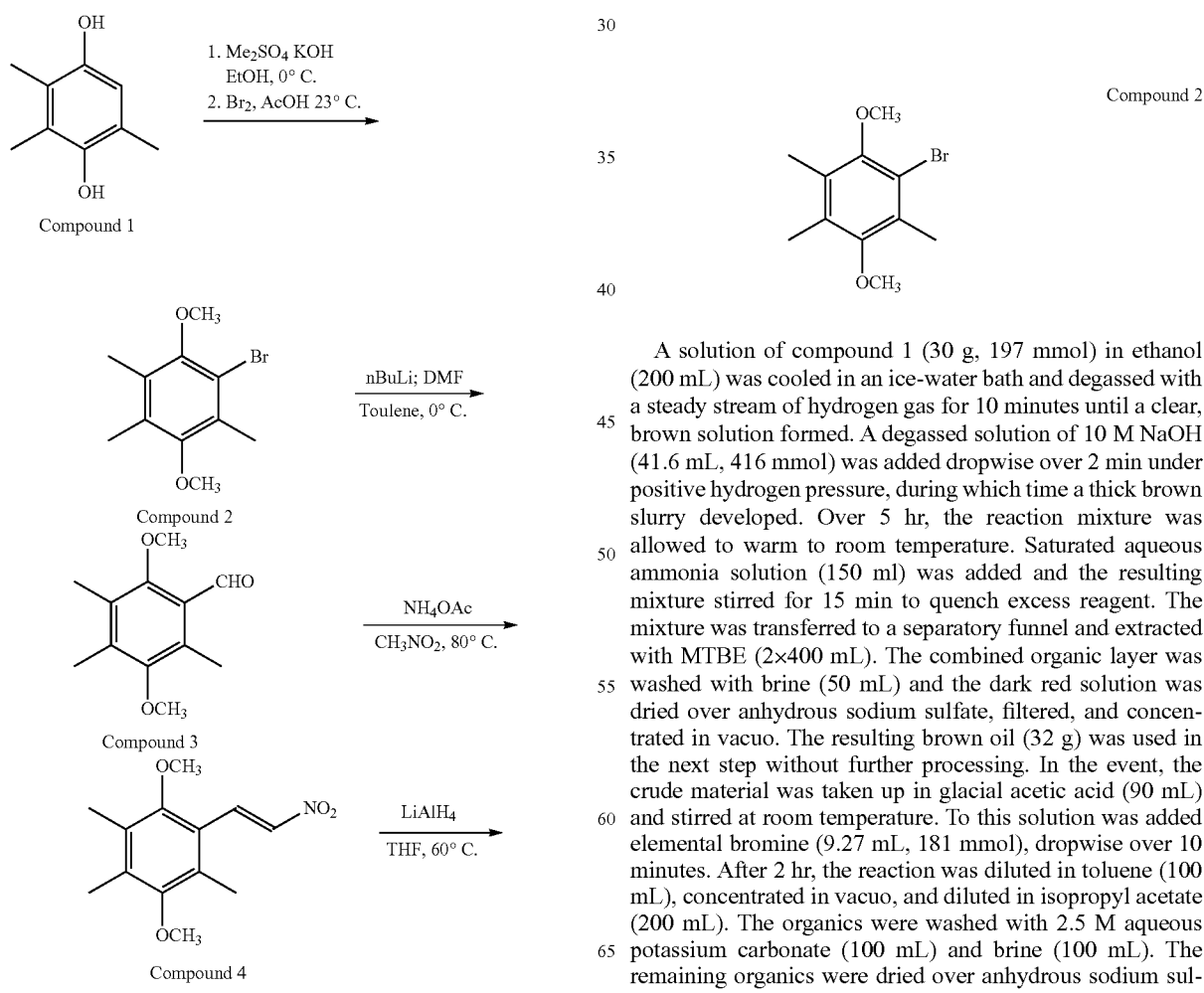

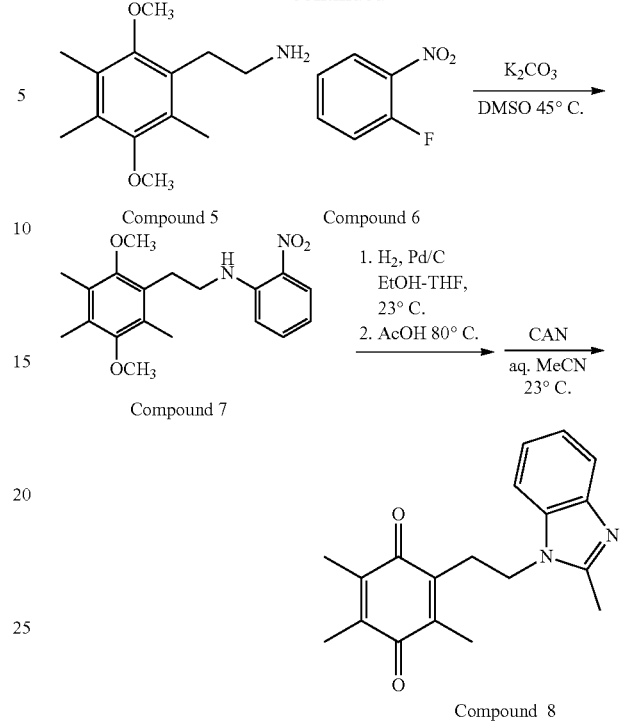

A solution of compound 1 (30 g, 197 mmol) in ethanol (200 mL) was cooled in an ice-water bath and degassed with a steady stream of hydrogen gas for 10 minutes until a clear, brown solution formed. A degassed solution of 10 M NaOH (41.6 mL, 416 mmol) was added dropwise over 2 min under positive hydrogen pressure, during which time a thick brown slurry developed. Over 5 hr, the reaction mixture was allowed to warm to room temperature. Saturated aqueous ammonia solution (150 ml) was added and the resulting mixture stirred for 15 min to quench excess reagent. The mixture was transferred to a separatory funnel and extracted with MTBE (2×400 mL). The combined organic layer was washed with brine (50 mL) and the dark red solution was dried over anhydrous sodium sulfate, filtered, and concentrated in vacuo. The resulting brown oil (32 g) was used in the next step without further processing. In the event, the crude material was taken up in glacial acetic acid (90 mL) and stirred at room temperature. To this solution was added elemental bromine (9.27 mL, 181 mmol), dropwise over 10 minutes. After 2 hr, the reaction was diluted in toluene (100 mL), concentrated in vacuo, and diluted in isopropyl acetate (200 mL). The organics were washed with 2.5 M aqueous potassium carbonate (100 mL) and brine (100 mL). The remaining organics were dried over anhydrous sodium sulfate, filtered, and concentrated in vacuo. The resulting solids were purified by stirring in 20% aqueous ethanol (150 mL), for 18 hrs. A pale orange/brown solid (26 g) was isolated by filtration, and structure (compound 2) confirmed by 1H NMR and HPLC-MS.

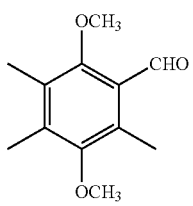

Compound 3

A solution of compound 2 (5 g, 19 mmol) in toluene (100 mL) was degassed with Ar for 15 min and cooled in an ice-water bath. To this solution was added a 1.6 M solution of n-butyllithium in hexanes (16 mL) over 30 seconds. After 30 min, DMF (7.1 mL, 90 mmol) was added and the mixture was allowed to warm to room temperature. The reaction mixture was diluted in ethyl acetate (100 mL), washed with water (50 mL) and brine (50 mL). The organics were dried over anhydrous sodium sulfate, filtered, and concentrated in vacuo to produce 4.5 g of orange/brown crystals judged to be compound 3 by 1H NMR and HPLC-MS.

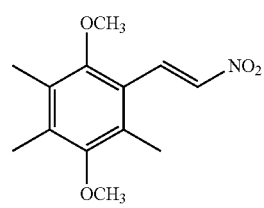

Compound 4

To a solution of crude compound 3 (4.5 g) in 100 mL nitromethane was added ammonium acetate (2.5 g, 30.1 mmol). The reaction mixture was stirred at 80° C. for 90 min. After the reaction was judged to be complete, the solvent was concentrated to 20% initial volume, diluted with ethyl acetate (100 mL), washed with water (50 mL) and brine (50 mL), dried over anhydrous sodium sulfate, filtered, and concentrated in vacuo to produce 5.4 g pale orange/yellow solid. The crude solid was purified by stirring in a minimal volume of cyclohexane. After 16 hr, orange solids (3.2 g) were collected and judged to be nitrostyrene 4 by 1H NMR and HPLC.

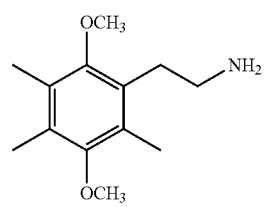

Compound 5

To a suspension of lithium aluminum hydride (3.0 g, 76 mmol) in THF (25 mL) cooled in an ice-water bath was added a solution of compound 4 (3.2 g) in THF (25 mL) dropwise over 15 minutes. The reaction mixture was then warmed to 60° C. for 3 hrs. The excess reagents were quenched by pouring the grey mixture onto 30 mL 6M aqueous sodium hydroxide. The resulting slurry was stirred for 30 minutes and filtered to produce a pale yellow biphasic solution. The mixture was transferred to a separatory funnel, washed with isopropyl acetate (2×100 mL) and the combined organics were dried over anhydrous sodium sulfate, filtered, and concentrated in vacuo to produce 3.0 g yellow oil. This material solidified overnight and was recrystallized from heptane to produce 3.0 g of a waxy, yellow low melting solid (compound 5) which was characterized by 1H NMR and HPLC-MS.

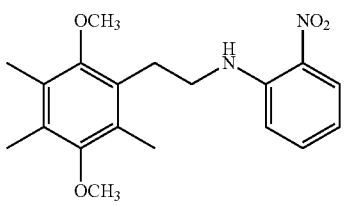

Compound 7

To a solution of compound 5 (200 mg, 89 µmol) in DMSO (4.5 mL) was added 1-fluoro-2-nitrobenzene (compound 6, 122 µL, 1.16 mmol), and potassium carbonate (271 mg, 1.96 mmol). The reaction mixture was warmed to 45° C. and stirred for 18 hrs. The resulting mixture was diluted with water (5 mL), extracted twice with MTBE (5 mL) and the combined organics were dried over anhydrous sodium sulfate, filtered, and concentrated in vacuo. The crude material (191 mg) was characterized by 1H NMR and HPLC-MS.

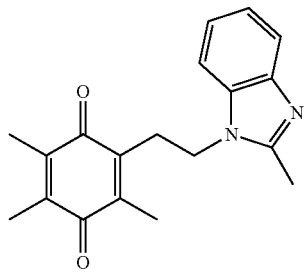

Compound 8

A solution of compound 7 (191 mg) in ethanol (2.75 mL) and THF (1 mL) was treated with 5% Pd/C (58 mg) and stirred under hydrogen gas (1 atm) for 4 hrs. After complete conversion of the starting material was determined by HPLC, acetic acid (100 µL) was added and the mixture was warmed to 80° C. and stirred for 18 hrs. The reaction was terminated by filtration and concentrated in vacuo. Conversion to the quinone product was accomplished by treatment of a solution of the crude product in acetonitrile (3 mL) with a solution of CAN (450 mg) in water (1 mL). After 30 minutes, the reaction mixture was transferred to a separatory funnel and diluted with ethyl acetate (50 mL). The organics were washed with brine (25 mL), dried over anhydrous sodium sulfate, filtered, and concentrated in vacuo. Purification was achieved using column chromatography and the product was characterized by 1H NMR and HPLC-MS.

The following N-linked heteroaryl compounds were made by a similar process:

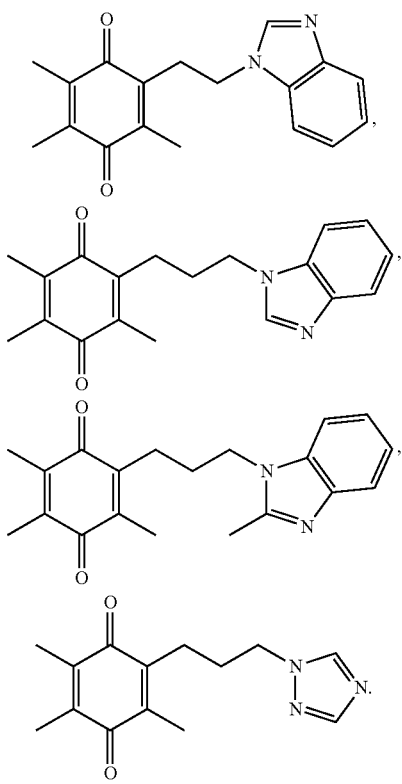

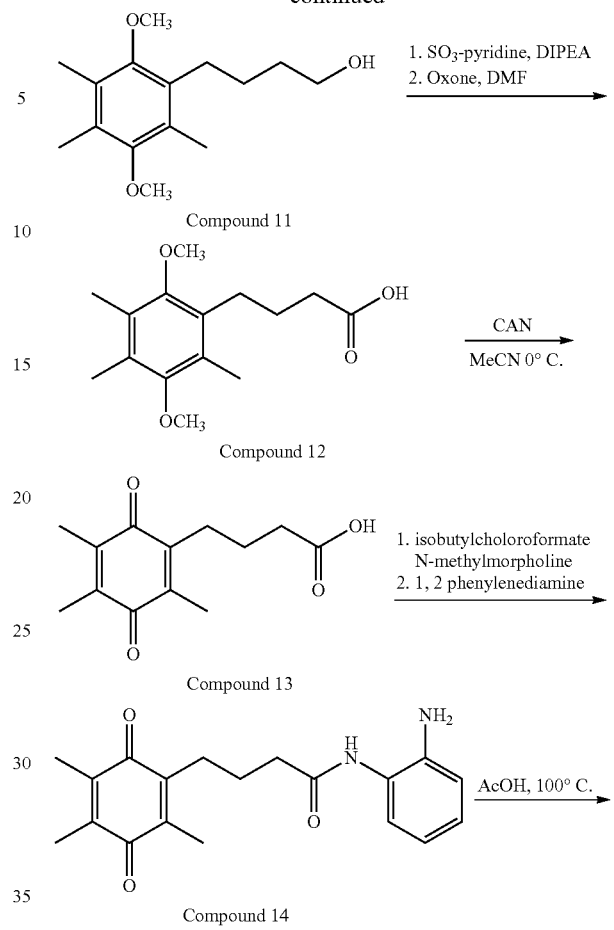

Example C. Synthesis of C-Linked Heteroaryl Compounds of the Invention

An exemplary synthesis of a C-linked heteroaryl compound of the invention is shown in the scheme below.

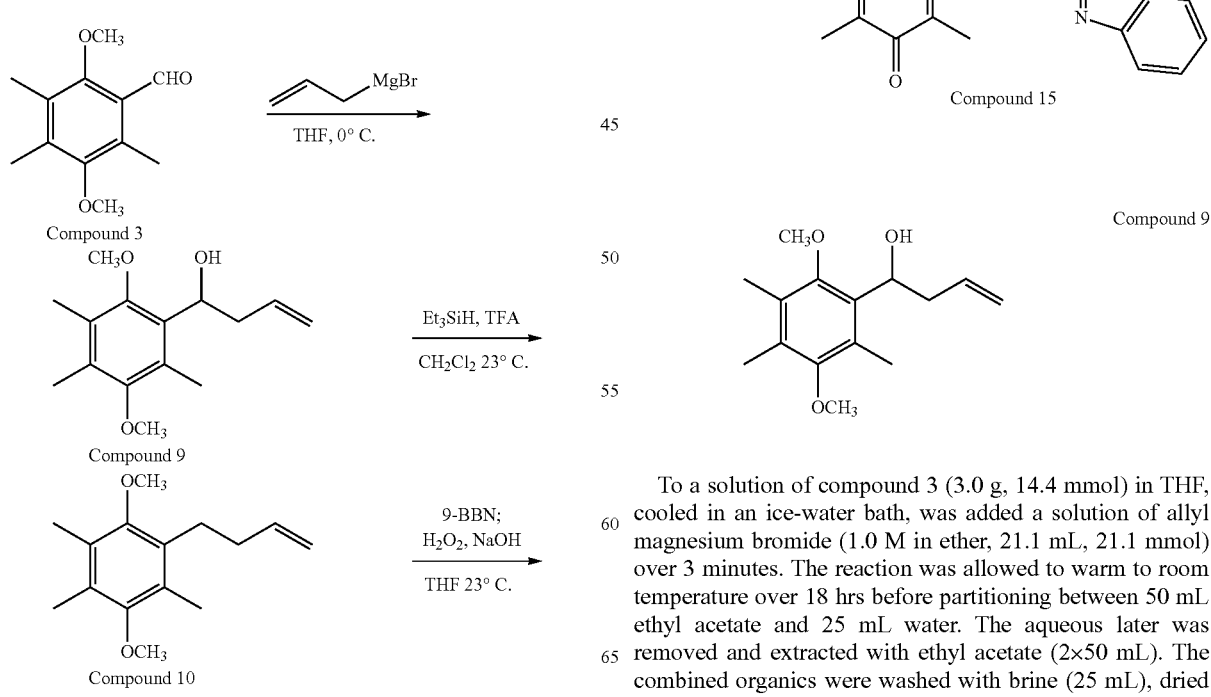

To a solution of compound 3 (3.0 g, 14.4 mmol) in THF, cooled in an ice-water bath, was added a solution of allyl magnesium bromide (1.0 M in ether, 21.1 mL, 21.1 mmol) over 3 minutes. The reaction was allowed to warm to room temperature over 18 hrs before partitioning between 50 mL ethyl acetate and 25 mL water. The aqueous later was removed and extracted with ethyl acetate (2×50 mL). The combined organics were washed with brine (25 mL), dried over anhydrous sodium sulfate, filtered, and concentrated in vacuo. Purification by column chromatography afforded the product, which was characterized by HPLC-MS and 1H NMR.

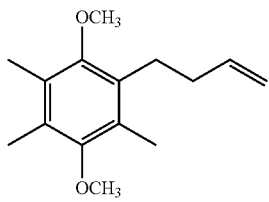

Compound 10

A solution of compound 9 (2.5 g, 10.1 mmol) in dichloromethane (10 mL) was treated with triethylsilane (8.0 mL, 50.3 mmol) and cooled in an ice-water bath. To the resulting solution was added TFA (5.2 mL, 70.4 mmol). An exotherm was observed and the reaction was allowed to warm to room temperature over 3 hours. The reaction mixture was then concentrated in vacuo and the material was used without further purification.

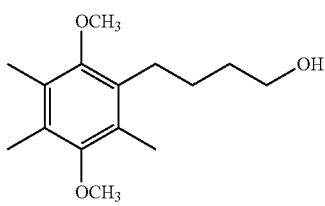

Compound 11

A solution of compound 10 (1.1 g, 4.7 mmol) in THF (10 mL) was treated with 9-BBN (630 mg, 5.16 mmol) and stirred for 4 hours at room temperature. After the initial reaction was judged to be complete by HPLC, the mixture was cooled in an ice-water bath and treated with aqueous sodium hydroxide (2.5 N, 15 mL) and hydrogen peroxide, (35% solution in water, 10 mL). The mixture was then allowed to warm to room temperature over 30 minutes. The reaction mixture was then transferred to a separatory funnel and extracted with isopropyl acetate (4×50 mL). The combined organics were then washed with brine (25 mL), dried over anhydrous sodium sulfate, filtered, and concentrated in vacuo to provide a colorless oil which was purified by column chromatography and characterized by HPLC-MS and 1H NMR.

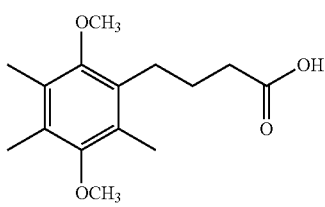

Compound 12

Compound 11 (10 g, 39.6 mmol) was dissolved in dichloromethane (50 mL) and cooled in an ice-water bath. To the resulting solution was added DIPEA (24 mL, 139 mmol). In a separate flask, sulfur trioxide-pyridine complex (12.6 g, 79.3 mmol), DMSO (14 mL) and pyridine (6.4 mL, 79.3 mmol) were added in sequence to form a slurry. The resulting slurry was added to the reaction mixture sequentially over 5 min. After 30 min, the reaction was transferred to an Erlenmeyer flask containing 50 g ice and 50 mL water and stirred for 10 min. The pH was slowly brought to 3.5 by addition of sulfuric acid. The mixture was extracted with dichloromethane (2×50 mL) which were dried over anhydrous sodium sulfate, filtered, and concentrated in vacuo to provide an oil. The crude material was taken up in DMF (80 mL) and treated with oxone (25.6 g, 41.6 mmol). After stirring overnight, the product was precipitated out of solution by addition of 100 mL water. The collected solid was further purified by recrystallization from water (8.1 g). The product was characterized by HPLC-MS and 1H NMR.

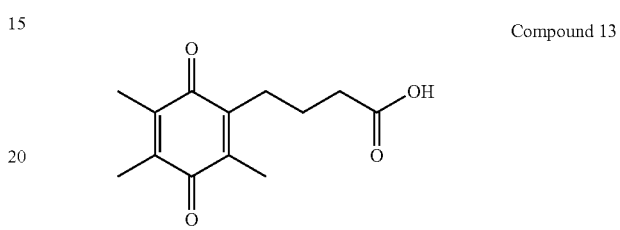

Compound 13

A solution of compound 12 (8.1 g, 30.7 mmol) in acetonitrile (150 mL) was cooled in an ice-water bath. To the solution was added a 1 M aqueous solution of CAN (62.9 mL, 62.9 mmol) in 5 mL portions. After TLC analysis indicated reaction was complete, the mixture was partitioned between 80 mL of isopropyl acetate and 40 mL of brine. The organics were removed, dried over anhydrous sodium sulfate, filtered, and concentrated in vacuo to provide a yellow oil which was used without further purification.

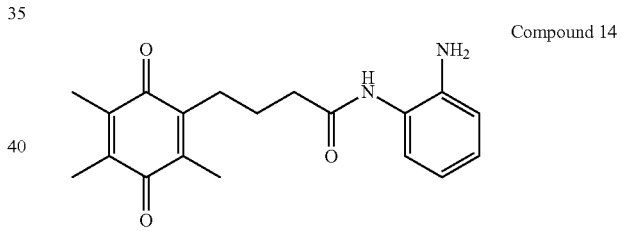

Compound 14

To a solution of compound 13 (4.25 g, 18.0 mmol) in isopropyl acetate (90 mL) was added isobutylchloroformate (2.5 mL, 18.9 mmol) followed by N-methyl morpholine (2.18 mL, 19.8 mmol). After 2 hrs, the reaction was split into 9 aliquots and treated with various amines (in this case, 1,2-phenylenediamine, 1.1 equivalents) and stirred for 18 hrs at room temperature. The reaction was worked up by washing with 2.5 N aqueous HCl (2.5 mL) and water (2.5 mL). Organics were dried over anhydrous sodium sulfate, filtered, and concentrated in vacuo to provide a yellow oil which was used without further purification.

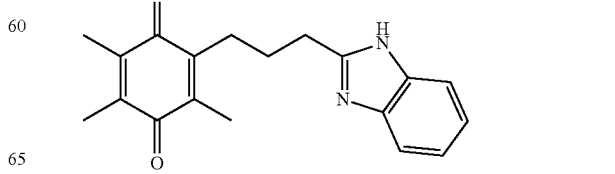

Compound 15

Compound 14 (160 mg) was dissolved in acetic acid (1 mL) and heated to 100° C. for 30 min. The crude product was recovered by cooling the reaction mixture to room temperature, diluting in water (1 mL) and extraction with 1 mL isopropyl acetate. Organics were dried over anhydrous sodium sulfate, filtered, and concentrated in vacuo to provide a yellow oil which was purified by column chromatography. The product was characterized by HPLC-MS and 1H NMR.

The following C-linked heteroaryl compounds were made by a similar process:

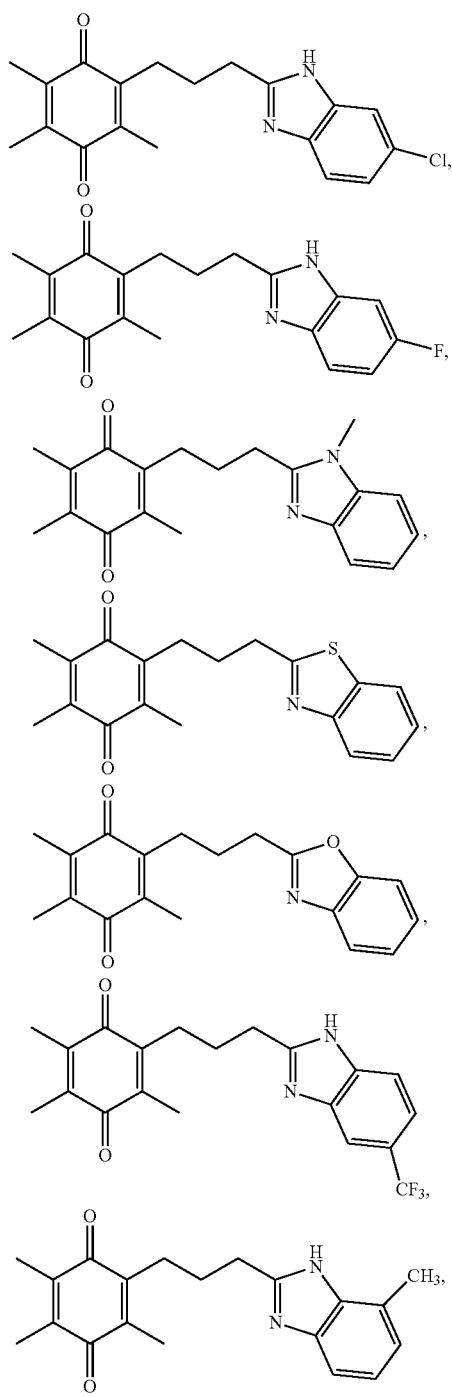

-continued

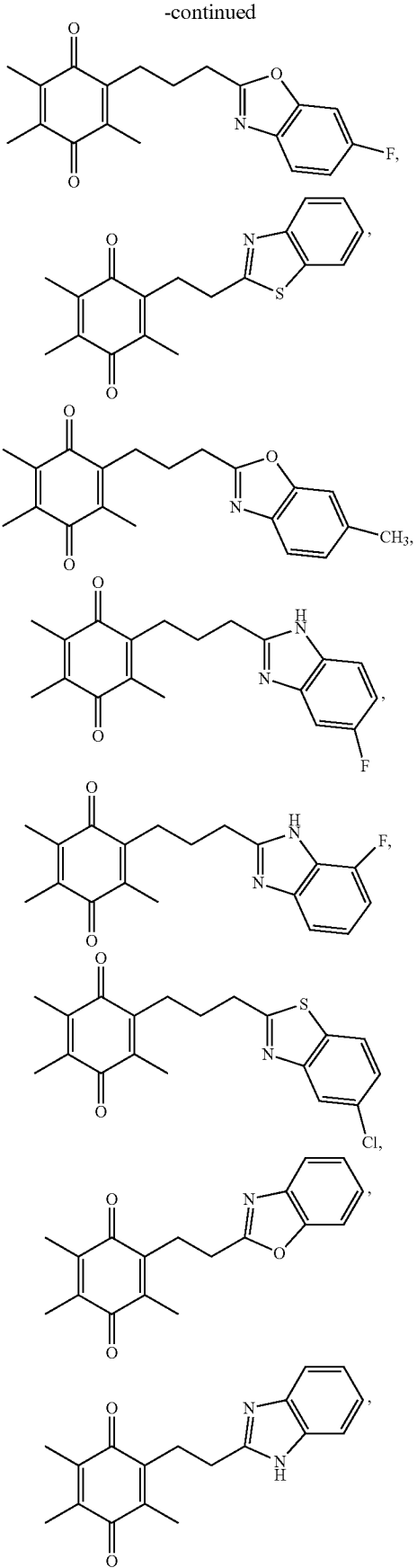

-continued

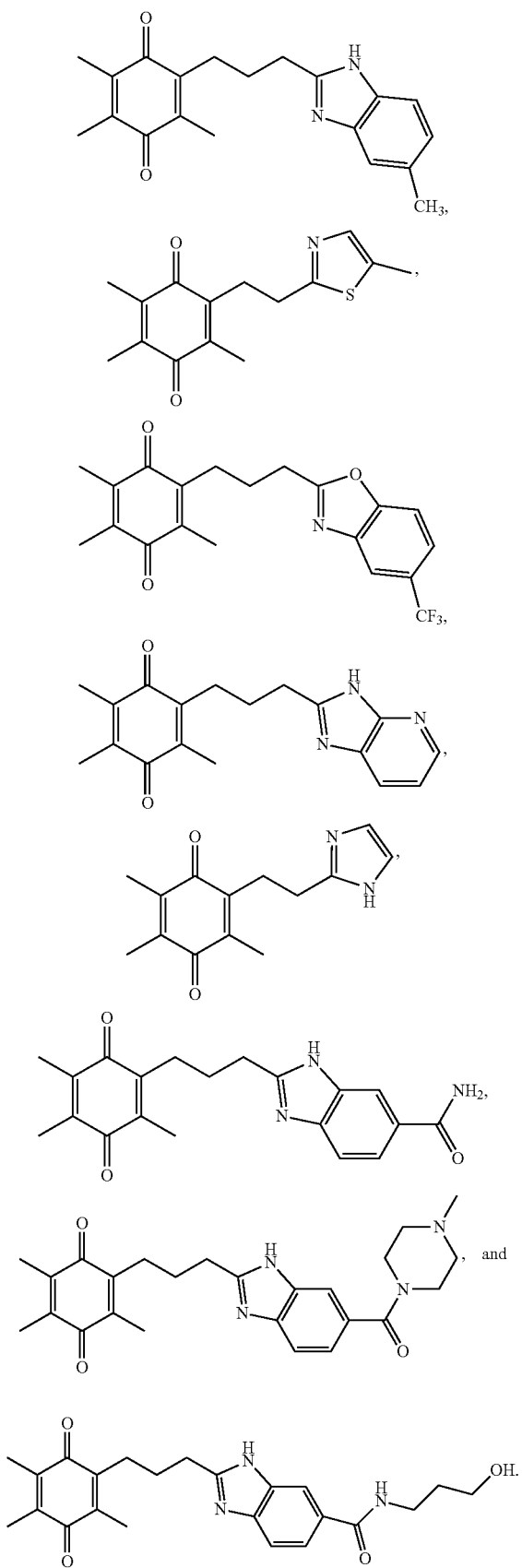

Example 1. Screening Compounds of the Invention in Human Dermal Fibroblasts from Friedreich's Ataxia Patients An initial screen was performed to identify compounds effective for the amelioration of redox disorders. Test samples, 4 reference compounds (idebenone, decylubiquinone, Trolox and alpha-tocopherol), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24): 3055 (2002)). This specific BSO-mediated cell death can be prevented by administration of antioxidants or molecules involved in the antioxidant pathway, such as alpha-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-alpha-tocopherol, decylubiquinone, and insulin from bovine pancreas were purchased from Sigma. Trolox (6-Hydroxy-2,5,7,8-tetramethylchromane-2-carboxylic acid) was obtained from Fluka. Idebenone was obtained from Chemo Iberica. Calcein AM was purchased from Anaspec. Cell culture medium was made by combining 125 ml M199 EBS, 50 ml Fetal Calf Serum, 100 U/ml penicillin, 100 microgram/ml streptomycin, 2 mM glutamine, 10 microgram/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium (Invitrogen, Carlsbad, Ca.) with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (idebenone, decylubiquinone, alpha-tocopherol and Trolox) were dissolved in DMSO.

Test samples were screened according to the following protocol:

A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 microliters medium with 3,000 cells/well. The remaining cells were distributed in 10 cm cell culture plates (500,000 cells/plate) for propagation. The plates were incubated overnight at 37° C. in a atmosphere with 95% humidity and 5% CO2 to allow attachment of the cells to the culture plate.

10% DMSO (242.5 microliters) was added to a well of the microtiter plate. The test compounds were unfrozen, and 7.5 microliters of a 5 mM stock solution was dissolved in the well containing 242.5 microliters of 10% DMSO, resulting in a 150 micromolar master solution. Serial dilutions from the master solution were made. The period between the single dilution steps was kept as short as possible (generally less than 30 seconds). At least 4 hours after attachment into MTP, cells were then treated with the various compound dilutions.

Plates were kept overnight in the cell culture incubator. The next day, 10 microliters of a 10 mM BSO solution were added to the wells, resulting in a 1 mM final BSO concentration. Forty-eight hours later, three plates were examined under a phase-contrast microscope to verify that the cells in the negative control (wells E1-H1) were clearly dead. The medium from all plates was discarded, and the remaining liquid was removed by gently tapping the plate inversed onto a paper towel. The plates were washed twice with 100 uL of PBS containing Calcium and Magnesium.

100 microliters of PBS+Ca+Mg containing 1.2 microM Calcein AM were then added to each well. The plates were incubated for 30 minutes at 37 C. After that time fluorescence (excitation/emission wavelengths of 485 nm and 525 nm, respectively) was read on a Gemini fluorescence reader.

Data was imported into Microsoft Excel (EXCEL is a registered trademark of Microsoft Corporation for a spreadsheet program) and ExcelFit was used to calculate the EC50 concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO— and compound-treated cells was calculated as relative to this value.

The following table summarizes the EC50 for the four control compounds.

| Compound | EC50 [µM] | | | | |
|---|---|---|---|---|---|
| | Value 1 | Value 2 | Value 3 | Average | Stdev |
| decylubiquinone | 0.05 | 0.035 | 0.03 | 0.038 | 0.010 |
| alpha-tocopherol | 0.4 | 0.15 | 0.35 | 0.30 | 0.13 |
| Idebenone | 1.5 | 1 | 1 | 1.2 | 0.3 |
| Trolox | 9 | 9 | 8 | 8.7 | 0.6 |

The following table summarizes the EC50 for certain compounds of the invention.

| Compound | Ec50 [micromolar] | |
|---|---|---|
| | Average | Stdev |
| 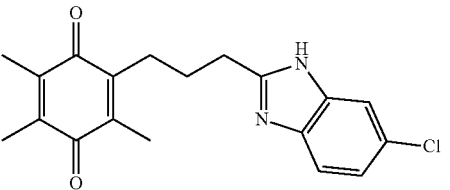 [SMILES: CC1=C(C)C(=O)C(CCCc2nc3ccc(Cl)cc3[nH]2)=C(C)C1=O] | 0.006 | 0.002 |
| 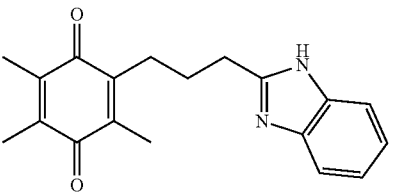 [SMILES: CC1=C(C)C(=O)C(CCCc2nc3ccccc3[nH]2)=C(C)C1=O] | 0.014 | N/A |
| 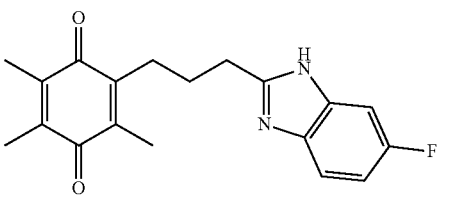 [SMILES: CC1=C(C)C(=O)C(CCCc2nc3ccc(F)cc3[nH]2)=C(C)C1=O] | 0.029 | 0.005 |
| 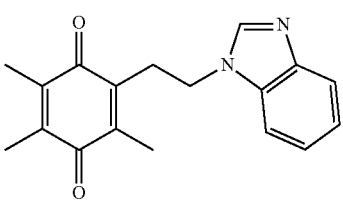 [SMILES: CC1=C(C)C(=O)C(CCn2cnc3ccccc32)=C(C)C1=O] | 0.028 | 0.010 |

-continued

| Compound | Ec50 [micromolar] Average | Stdev |
|---|---|---|
| (trimethyl-benzoquinone-propyl-1-methylbenzimidazole) | 0.025 | 0.004 |
| (trimethyl-benzoquinone-propyl-benzothiazole) | 0.006 | 0.0006 |
| (trimethyl-benzoquinone-propyl-benzoxazole) | 0.020 | 0.031 |
| (trimethyl-benzoquinone-ethyl-2-methylbenzimidazole) | 0.049 | 0.003 |
| (trimethyl-benzoquinone-propyl-benzimidazole) | 0.021 | 0.003 |
| (trimethyl-benzoquinone-propyl-2-methylbenzimidazole) | 0.026 | 0.006 |
| (trimethyl-benzoquinone-propyl-triazole) | 0.426 | 0.046 |

-continued
| Compound | Ec50 [micromolar] | |
|---|---|---|
| | Average | Stdev |
| 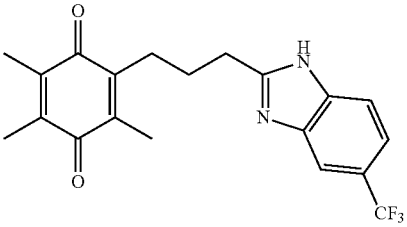 [SMILES: CC1=C(C)C(=O)C(CCCc2nc3cc(C(F)(F)F)ccc3[nH]2)=C(C)C1=O] | 0.008 | 0.002 |
| 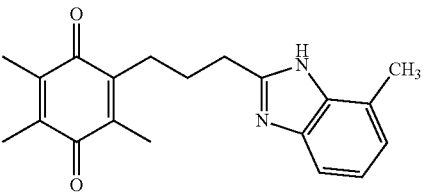 | 0.007 | 0.0003 |
| 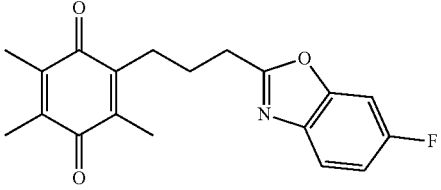 [SMILES: CC1=C(C)C(=O)C(CCCc2nc3ccc(F)cc3o2)=C(C)C1=O] | 0.010 | 0.0003 |
| 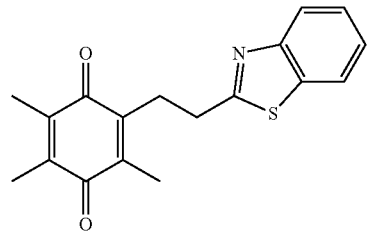 [SMILES: CC1=C(C)C(=O)C(CCc2nc3ccccc3s2)=C(C)C1=O] | 0.006 | 0.0006 |
| 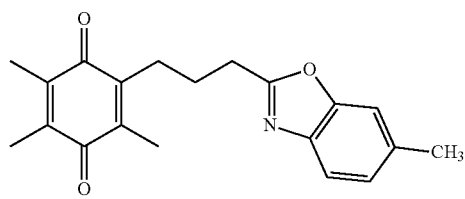 | 0.007 | 0.002 |
| 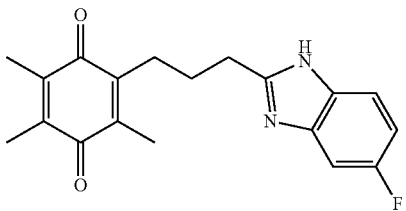 [SMILES: CC1=C(C)C(=O)C(CCCc2nc3cc(F)ccc3[nH]2)=C(C)C1=O] | 0.009 | 0.001 |
| 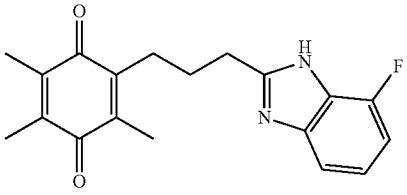 [SMILES: CC1=C(C)C(=O)C(CCCc2nc3cccc(F)c3[nH]2)=C(C)C1=O] | 0.018 | 0.004 |

-continued

| Compound | Ec50 [micromolar] | |
|---|---|---|
| | Average | Stdev |
| (structure: trimethylbenzoquinone-propyl-benzothiazole-Cl) | 0.028 | 0.001 |
| (structure: trimethylbenzoquinone-ethyl-benzoxazole) | 0.018 | 0.004 |
| (structure: trimethylbenzoquinone-ethyl-benzimidazole) | 0.020 | 0.006 |
| (structure: trimethylbenzoquinone-propyl-benzimidazole-CH₃) | 0.021 | 0.002 |
| (structure: trimethylbenzoquinone-ethyl-methylthiazole) | 0.027 | 0.006 |
| (structure: trimethylbenzoquinone-propyl-benzoxazole-CF₃) | 0.027 | 0.001 |

-continued

| Compound | Ec50 [micromolar] | |
| --- | --- | --- |
| | Average | Stdev |
| 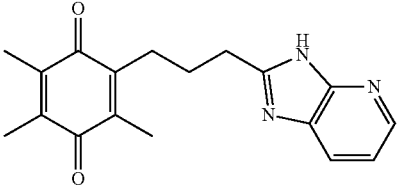 [SMILES: CC1=C(C)C(=O)C(CCCc2nc3cccnc3[nH]2)=C(C)C1=O] | 0.113 | 0.003 |
| 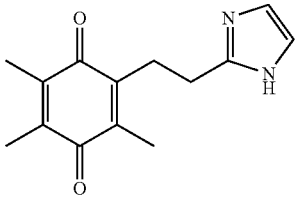 [SMILES: CC1=C(C)C(=O)C(CCc2ncc[nH]2)=C(C)C1=O] | 0.225 | 0.012 |
| 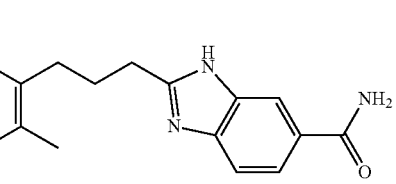 | 0.080 | 0.003 |
| 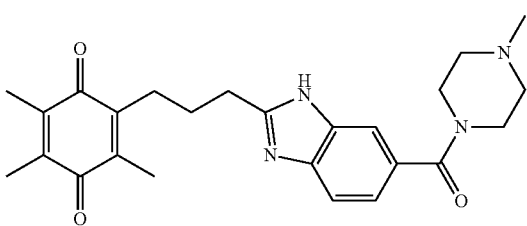 | 0.092 | 0.002 |
| 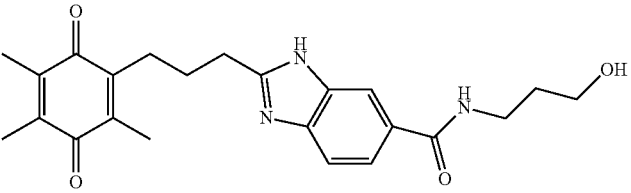 [SMILES: CC1=C(C)C(=O)C(CCCc2nc3ccc(C(=O)NCCCO)cc3[nH]2)=C(C)C1=O] | >0.200 | N/A |

Example 2. Screening Compounds of the Invention in Fibroblasts from Huntington's Patients Compounds of the invention are tested using a screen similar to the one described in Example 1, but substituting FRDA cells with Huntington's cells obtained from the Coriell Cell Repositories (Camden, N.J.; repository number GM 04281). The compounds are tested for their ability to rescue human dermal fibroblasts from Huntington's patients from oxidative stress.

Example 3. Screening Compounds of the Invention in Fibroblasts from Leber's Hereditary Optic Neuropathy Patients Compounds of the invention are tested using a screen similar to the one described in Example 1, but substituting FRDA cells with Leber's Hereditary Optic Neuropathy (LHON) cells obtained from the Coriell Cell Repositories (Camden, N.J.; repository number GM03858). The compounds are tested for their ability to rescue human dermal fibroblasts from LHON patients from oxidative stress.

Example 4. Screening Compounds of the Invention in Fibroblasts from Parkinson's Disease Patients Compounds of the invention are tested using a screen similar to the one described in Example 1, but substituting FRDA cells with Parkinson's Disease (PD) cells obtained from the Coriell Cell Repositories (Camden, N.J.; repository number AG20439). The compounds are tested for their ability to rescue human dermal fibroblasts from Parkinson's Disease patients from oxidative stress.

Example 5. Screening Compounds of the Invention in Fibroblasts from CoQ10 Deficient Patients Compounds of the invention are tested using a screen similar to the one described in Example 1, but substituting FRDA cells with cells obtained from CoQ10 deficient patients harboring a CoQ2 mutation. The compounds are tested for their ability to rescue human dermal fibroblasts from CoQ10 deficient patients from oxidative stress.

Example 6. Screening Compounds of the Invention in Fibroblasts from Patients

Compounds of the invention are tested using a screen similar to the one described in Example 1, but substituting FRDA cells with cells obtained from patients having an oxidative stress disorder described herein (e.g. MERRF, MELAS, Leigh Disease, KSS, Alzheimer's disease, ALS, a pervasive development disorder (such as autism, Rett's), stroke). The compounds are tested for their ability to rescue human dermal fibroblasts from these patients from oxidative stress.

Example 7. Administration of Compounds of the Invention

A compound of the invention is presented in a capsule containing 300 mg of compound in a pharmaceutically acceptable carrier. A capsule is taken orally, once a day, preferably during breakfast or lunch. In case of very young children, the capsule is broken and its contents mixed with food.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula I or Formula II:

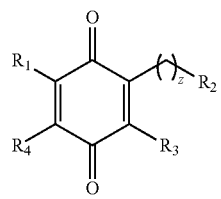

Formula I wherein:
$R_1$, $R_3$ and $R_4$ are independently $C_1$-$C_6$ alkyl or O—$C_1$-$C_6$ alkyl;
$R_2$ is heteroaryl selected from the group consisting of benzoimidazole, benzothiazole, and benzoxazole, optionally substituted with one or two substituents independently selected from the group consisting of halo, —$CH_3$, —$CF_3$, —$OCH_3$, and —C(O)—N($R_5$)($R_6$), wherein the substituents are independently linked to the heteroaryl by either a —C— or —N— within the heteroaryl; where the attachment point of the heteroaryl group to the rest of the molecule is either through a C or N in the rings;
$R_5$ and $R_6$ are independently selected from the group consisting of —H, —$C_1$-$C_6$ alkyl, and —$C_1$-$C_6$ alkyl-hydroxy, or wherein $R_5$ and $R_6$ together with the N to which they are attached form a saturated or unsaturated 3-8 membered ring, optionally incorporating one, two, or three additional heteroatoms each independently selected from the group consisting of N, O, and S, and wherein the ring is optionally substituted with —$C_1$-$C_6$ alkyl; and
z is 3;
or a stereoisomer, mixture of stereoisomers, solvate, hydrate, pharmaceutically acceptable salt or prodrug ester thereof.

2. The compound of claim 1, wherein:
$R_2$ is heteroaryl optionally substituted with one or two substituents independently selected from the group consisting of halo, —$CH_3$, —$CF_3$, and —$OCH_3$, wherein the substituents are independently linked to the heteroaryl by either a —C— or —N— within the heteroaryl.

3. The compound of claim 1, wherein $R_1$, $R_3$ and $R_4$ are independently $C_1$-$C_4$ alkyl.

4. The compound of claim 1, wherein $R_1$, $R_3$ and $R_4$ are independently $C_1$-$C_2$ alkyl.

5. The compound of claim 1, wherein $R_1$, $R_3$ and $R_4$ are —$CH_3$.

6. The compound of claim 1, wherein $R_1$ and $R_4$ are independently —O—$C_1$-$C_2$ alkyl, and $R_3$ is $C_1$-$C_4$ alkyl.

7. The compound of claim 1, wherein $R_1$ and $R_4$ are —$OCH_3$, and $R_3$ is —$CH_3$.

8. The compound of claim 1, wherein the compound is a compound of Formula I, or a stereoisomer, mixture of stereoisomers, solvate, hydrate, or pharmaceutically acceptable salt thereof.

9. The compound of claim 1, wherein the compound is selected from the group consisting of:

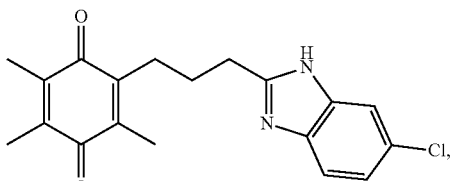

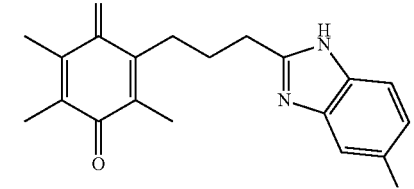

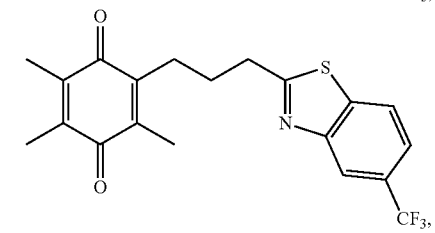

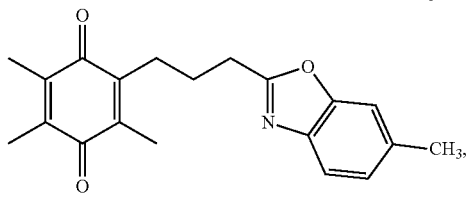

117
-continued
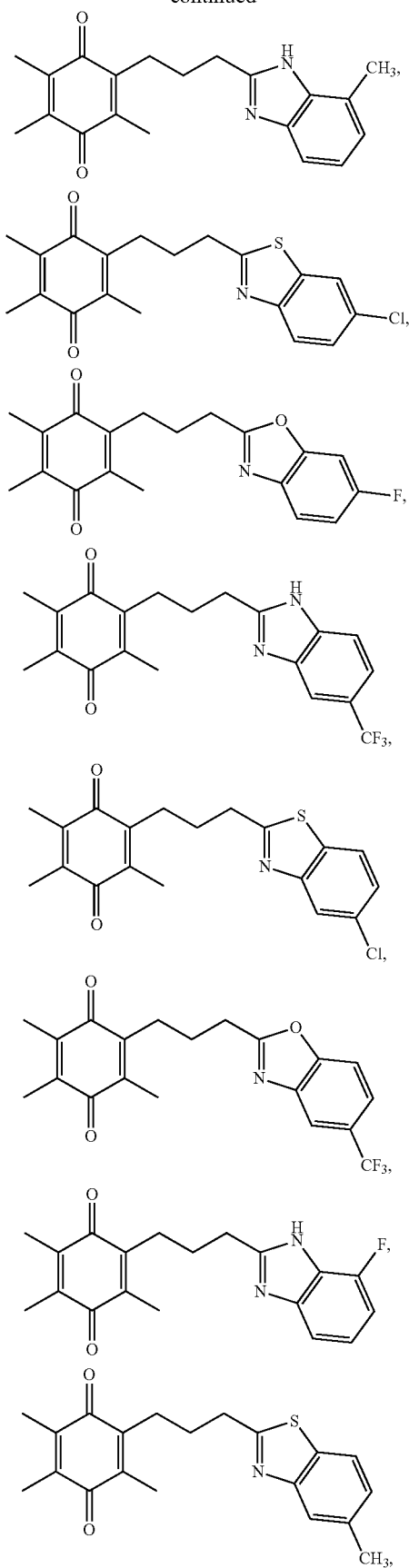
118
-continued
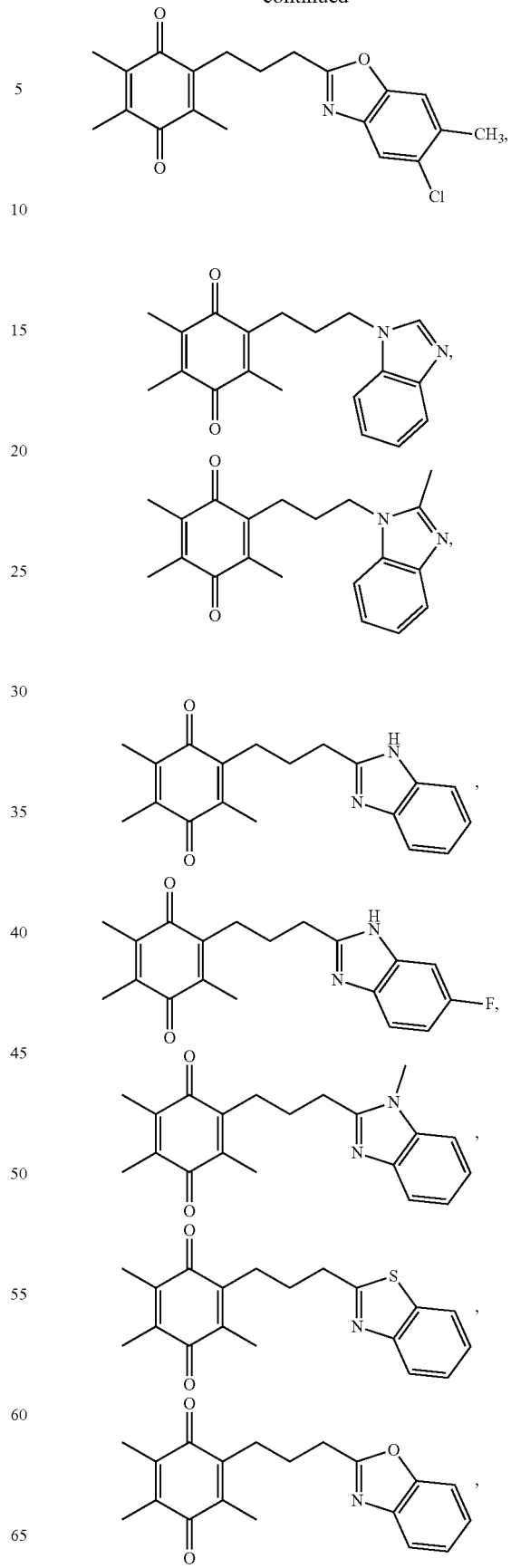

119
-continued
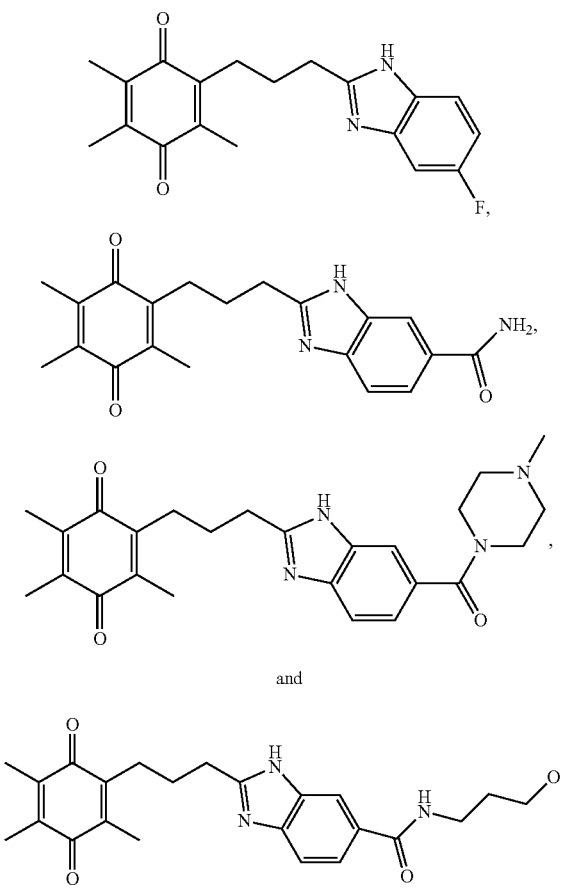
and
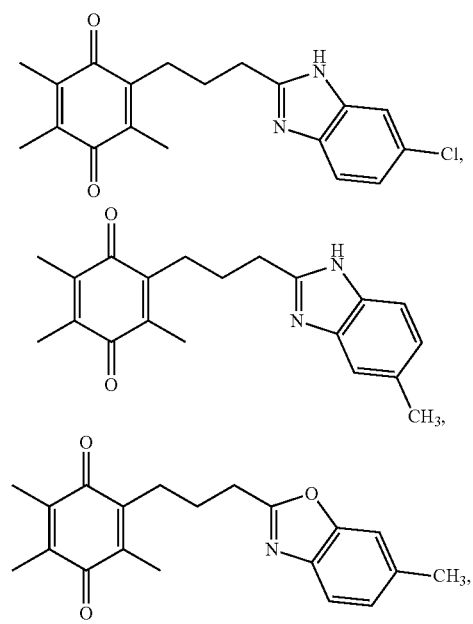
or a solvate, hydrate, pharmaceutically acceptable salt, or prodrug ester thereof.
10. The compound of claim 1, wherein the compound is selected from the group consisting of:
120
-continued
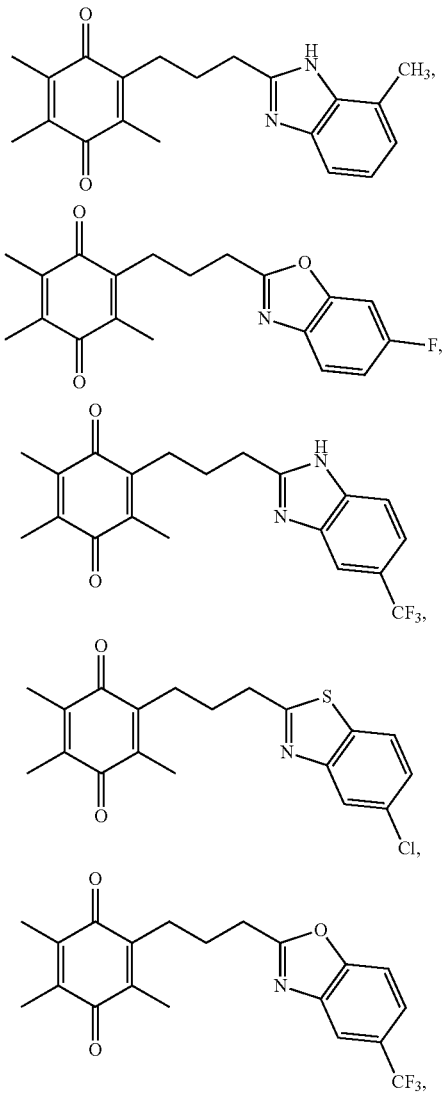

-continued

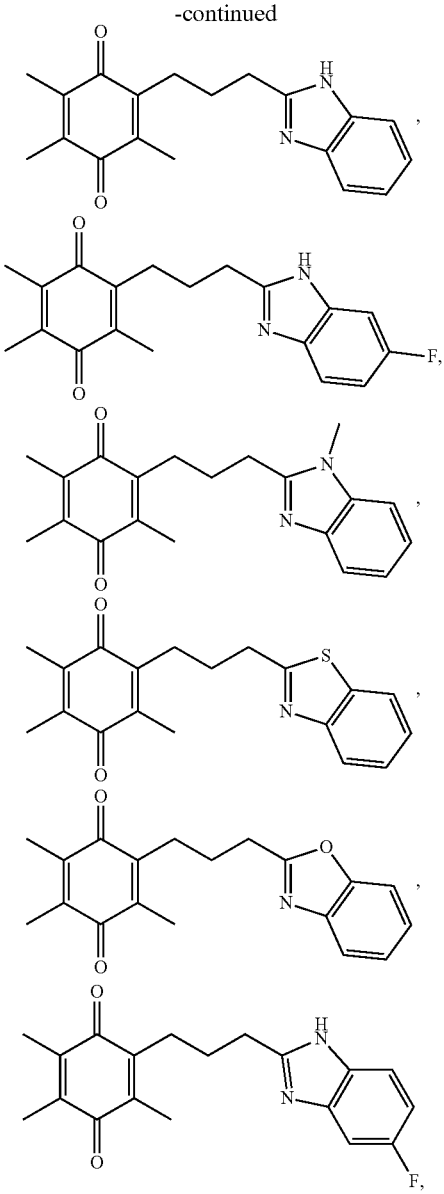

-continued

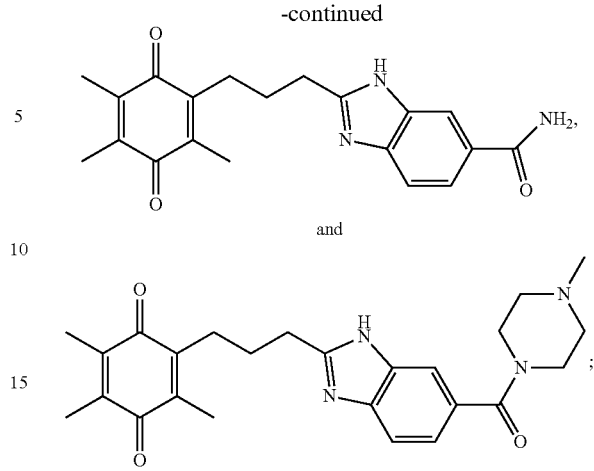

or a solvate, hydrate, pharmaceutically acceptable salt, or prodrug ester thereof.

11. A pharmaceutical formulation comprising a compound according to claim 1 and a pharmaceutically acceptable excipient.

12. The compound of claim 1, wherein $R_2$ is benzoimidazole optionally substituted with one or two substituents independently selected from the group consisting of halo, —$CH_3$, —$CF_3$, —$OCH_3$, and —C(O)—N($R_5$)($R_6$), wherein the substituents are independently linked to the benzoimidazole by either a —C— or —N— within the benzoimidazole.

13. The compound of claim 1, wherein $R_2$ is benzothiazole optionally substituted with one or two substituents independently selected from the group consisting of halo, —$CH_3$, —$CF_3$, —$OCH_3$, and —C(O)—N($R_5$)($R_6$), wherein the substituents are independently linked to the benzothiazole by either a —C— or —N— within the benzothiazole.

14. The compound of claim 1, wherein $R_2$ is benzoxazole optionally substituted with one or two substituents independently selected from the group consisting of halo, —$CH_3$, —$CF_3$, —$OCH_3$, and —C(O)—N($R_5$)($R_6$), wherein the substituents are independently linked to the benzoxazole by either a —C— or —N— within the benzoxazole.

* * * * *